United States Patent
Song et al.

(10) Patent No.: US 11,827,703 B2
(45) Date of Patent: *Nov. 28, 2023

(54) COMPOSITIONS AND METHODS RELATED TO ANTI-CD19 ANTIBODY DRUG CONJUGATES

(71) Applicants: LegoChem Biosciences, Inc., Yuseong-gu (KR); NovImmune, SA, Geneva (CH)

(72) Inventors: Ho Young Song, Deajeon (KR); Yun Hee Park, Deajeon (KR); Sung Min Kim, Daejeon (KR); Hyoung Rae Kim, Daejeon (KR); Ji Hye Oh, Daejeon (KR); Hyun Min Ryu, Daejeon (KR); Jeiwook Chae, Daejeon (KR); Yeong Soo Oh, Daejeon (KR); Yong Zu Kim, Daejeon (KR); Maureen Deehan, Zug (CH); Nicolas Fischer, Geneva (CH)

(73) Assignees: LegoChem Biosciences, Inc., Daejeon (KR); NovImmune, SA, Geneva (CH)

( * ) Notice: Subject to any disclaimer, the term of this patent is extended or adjusted under 35 U.S.C. 154(b) by 295 days.

This patent is subject to a terminal disclaimer.

(21) Appl. No.: 16/408,002

(22) Filed: May 9, 2019

(65) Prior Publication Data

US 2020/0095317 A1    Mar. 26, 2020

Related U.S. Application Data

(60) Provisional application No. 62/669,183, filed on May 9, 2018.

(51) Int. Cl.
| | | |
|---|---|---|
| *C07K 16/28* | (2006.01) | |
| *A61K 47/68* | (2017.01) | |
| *C07H 15/203* | (2006.01) | |
| *A61K 31/5517* | (2006.01) | |
| *A61K 31/7052* | (2006.01) | |
| *A61K 45/06* | (2006.01) | |

(52) U.S. Cl.
CPC ...... *C07K 16/2803* (2013.01); *A61K 31/5517* (2013.01); *A61K 31/7052* (2013.01); *A61K 47/6803* (2017.08); *C07H 15/203* (2013.01); *A61K 45/06* (2013.01); *C07K 2317/24* (2013.01); *C07K 2317/31* (2013.01); *C07K 2317/569* (2013.01); *C07K 2317/622* (2013.01)

(58) Field of Classification Search
CPC ............ C07K 16/2803; C07K 2317/24; C07K 2317/31; C07K 2317/569; C07K 2317/622; C07K 2317/33; A61K 31/5517; A61K 31/7052; A61K 47/6803; A61K 45/06; A61K 47/6867; A61K 47/6849; A61K 47/68; A61K 47/6851; A61K 47/6889; A61K 2039/505; C07H 15/203; Y02A 50/30; Y02P 20/55; A61P 35/00; A61P 37/00

See application file for complete search history.

(56) References Cited

U.S. PATENT DOCUMENTS

| | | | |
|---|---|---|---|
| 5,112,739 A | 5/1992 | Meneghini et al. | |
| 5,935,995 A | 8/1999 | Bosslet et al. | |
| 6,218,519 B1 | 4/2001 | Kenten et al. | |
| 6,759,509 B1 | 7/2004 | King et al. | |
| 8,039,273 B2 | 10/2011 | Jeffrey | |
| 8,568,728 B2 | 10/2013 | Jeffrey | |
| 9,919,057 B2 | 3/2018 | Kim et al. | |
| 9,993,568 B2 | 6/2018 | Kim et al. | |
| 10,118,965 B2 | 10/2018 | Kim et al. | |
| 10,183,997 B2 | 1/2019 | Kim et al. | |
| 10,383,949 B2 | 8/2019 | Kim et al. | |
| 10,980,890 B2 | 4/2021 | Kim et al. | |
| 11,167,040 B2 | 11/2021 | Kim et al. | |
| 11,173,214 B2 | 11/2021 | Kim et al. | |
| 11,413,353 B2 | 8/2022 | Kim et al. | |
| 2005/0238649 A1 | 10/2005 | Doronina et al. | |
| 2006/0088522 A1 | 4/2006 | Boghaert et al. | |
| 2008/0057063 A1* | 3/2008 | Rinkenberger ......... | A61P 11/00 530/391.1 |
| 2009/0299038 A1 | 12/2009 | Nakamura et al. | |

(Continued)

FOREIGN PATENT DOCUMENTS

| | | |
|---|---|---|
| CA | 2921707 A1 | 4/2015 |
| CN | 1185786 A | 6/1998 |

(Continued)

OTHER PUBLICATIONS

Rudikoff et al (Proc. Natl. Acad. Sci. USA, 79(6):1979-1983, Mar. 1982) (Year: 1982).*

(Continued)

*Primary Examiner* — Adam Weidner
*Assistant Examiner* — John J Skoko, III
(74) *Attorney, Agent, or Firm* — Foley Hoag LLP; David P. Halstead; Lucas P. Watkins

(57) ABSTRACT

The present disclosure relates to antibody-drug conjugates (ADCs) wherein one or more active agents are conjugated to an anti-CD19 antibody through a linker. The linker may comprise a unit that covalently links active agents to the antibody. The disclosure further relates to monoclonal antibodies and antigen binding fragments, variants, multimeric versions, or bispecifics thereof that specifically bind CD19, as well as methods of making and using these anti-CD19 antibodies and antigen-binding fragments thereof in a variety of therapeutic, diagnostic and prophylactic indications.

41 Claims, 17 Drawing Sheets
Specification includes a Sequence Listing.

(56) References Cited

U.S. PATENT DOCUMENTS

| | | |
|---|---|---|
| 2009/0326205 A1 | 12/2009 | Nakamura et al. |
| 2012/0030858 A1 | 2/2012 | Duffin |
| 2012/0058051 A1 | 3/2012 | Rader et al. |
| 2012/0107332 A1 | 5/2012 | Jeffrey |
| 2012/0308584 A1 | 12/2012 | Kim et al. |
| 2013/0251723 A1 | 9/2013 | Rohlff et al. |
| 2014/0031535 A1 | 1/2014 | Jeffrey |
| 2014/0032535 A1 | 1/2014 | Singla |
| 2014/0072558 A1 | 3/2014 | Park et al. |
| 2014/0088292 A1 | 3/2014 | Kim et al. |
| 2014/0161829 A1 | 6/2014 | Kim et al. |
| 2014/0187756 A1 | 7/2014 | Kim et al. |
| 2014/0286969 A1 | 9/2014 | Tschoepe et al. |
| 2015/0105541 A1 | 4/2015 | Kim et al. |
| 2016/0184451 A1 | 6/2016 | Kim et al. |
| 2016/0256561 A1 | 9/2016 | Howard et al. |
| 2016/0257709 A1 | 9/2016 | Kline et al. |
| 2017/0088614 A1* | 3/2017 | Kim .................. A61K 47/6803 |
| 2017/0088621 A1 | 3/2017 | Kim et al. |
| 2017/0095576 A1 | 4/2017 | Kim et al. |
| 2018/0142018 A1* | 5/2018 | Fischer .............. A61K 47/6849 |
| 2018/0193481 A1 | 7/2018 | Chang et al. |
| 2018/0265593 A1 | 9/2018 | Chen et al. |
| 2018/0369406 A1 | 12/2018 | Lannutti et al. |
| 2019/0151465 A1 | 5/2019 | Kim et al. |
| 2019/0381185 A1 | 12/2019 | Kim et al. |
| 2020/0069816 A1 | 3/2020 | Kim et al. |
| 2020/0095317 A1 | 3/2020 | Song et al. |
| 2020/0297865 A1 | 9/2020 | Kim et al. |
| 2021/0069342 A1 | 3/2021 | Park et al. |
| 2021/0214432 A1 | 7/2021 | Lim et al. |
| 2022/0218830 A1 | 7/2022 | Song et al. |
| 2022/0218840 A1 | 7/2022 | Kim et al. |
| 2022/0339291 A1 | 10/2022 | Park et al. |

FOREIGN PATENT DOCUMENTS

| | | |
|---|---|---|
| CN | 101287500 A | 10/2008 |
| CN | 101573384 A | 11/2009 |
| CN | 101835803 A | 9/2010 |
| CN | 103648530 A | 3/2014 |
| CN | 105358579 A | 2/2016 |
| CN | 107530423 A | 1/2018 |
| CN | 1107847596 A | 3/2018 |
| EP | 2913064 A1 | 9/2015 |
| EP | 3156424 A1 | 4/2017 |
| EP | 3604311 A1 | 2/2020 |
| KR | 10-2009-0088893 A | 8/2009 |
| KR | 10-2012-0113175 A | 10/2012 |
| KR | 2014/0035393 A | 3/2014 |
| KR | 10-2015-0137015 | 6/2016 |
| KR | 10-2014-0192328 | 7/2016 |
| KR | 10-2018-0110645 A | 10/2018 |
| KR | 10-2019-0018400 A | 2/2019 |
| KR | 10-2019-0028350 A | 3/2019 |
| KR | 10-2020-0084802 A | 7/2020 |
| RU | 2191021 C2 | 10/2002 |
| RU | 2651776 C2 | 4/2018 |
| TW | 201524520 A | 7/2015 |
| WO | WO-98/19705 A1 | 5/1998 |
| WO | WO-2004050089 A1 | 6/2004 |
| WO | WO-2007/011968 A2 | 1/2007 |
| WO | WO-2008/034120 A2 | 3/2008 |
| WO | WO-2009/016647 A1 | 2/2009 |
| WO | WO-2009/054863 A2 | 4/2009 |
| WO | WO-2011066418 A1 | 6/2011 |
| WO | WO-2011/145068 A1 | 11/2011 |
| WO | WO-2012/138102 A2 | 10/2012 |
| WO | WO-2012/153193 A2 | 11/2012 |
| WO | WO-2013055990 A1 | 4/2013 |
| WO | WO-2013103707 A1 | 7/2013 |
| WO | WO-2014/096368 A1 | 6/2014 |
| WO | WO-2014/194030 A2 | 12/2014 |
| WO | WO-2015/057699 A2 | 4/2015 |
| WO | WO-2015/095755 A1 | 6/2015 |
| WO | WO-2015/182984 A1 | 12/2015 |
| WO | WO-2016/033570 A1 | 3/2016 |
| WO | WO-2016/040684 A1 | 3/2016 |
| WO | WO-2016/094517 A1 | 6/2016 |
| WO | WO-2016108587 A1 | 7/2016 |
| WO | WO-2016/142768 A1 | 9/2016 |
| WO | WO-2017/051249 A1 | 3/2017 |
| WO | WO-2017/051254 A1 | 3/2017 |
| WO | WO-2017/066136 A2 | 4/2017 |
| WO | WO-2017089890 A1 | 6/2017 |
| WO | WO-2017089894 A1 | 6/2017 |
| WO | WO-2017089895 A1 | 6/2017 |
| WO | WO-2018/069490 A1 | 4/2018 |
| WO | WO-2018/083535 A1 | 5/2018 |
| WO | WO-2018/146199 A1 | 8/2018 |
| WO | WO2018/182341 A1 | 10/2018 |
| WO | WO-2018/200812 A1 | 11/2018 |
| WO | WO-2019/050362 A2 | 3/2019 |
| WO | WO-2019/215510 A2 | 11/2019 |
| WO | WO-2019/225777 A1 | 11/2019 |
| WO | WO-2019/225992 A1 | 11/2019 |
| WO | WO-2020/180121 A1 | 9/2020 |
| WO | WO-2019/215510 A8 | 11/2020 |
| WO | WO-2021/044208 A1 | 3/2021 |

OTHER PUBLICATIONS

Paul, Fundamental Immunology, 3rd Edition, 1993, pp. 292-295 (Year: 1993).*

Colman P. M. (Research in Immunology, 145:33-36, 1994) (Year: 1994).*

Bendig M. M. (Methods: A Companion to Methods in Enzymology, 1995; 8:83-93) (Year: 1995).*

Edwards et al. The remarkable flexibility of the human antibody repertoire; isolation of over one thousand different antibodies to a single protein, BLyS. J Mol Biol. Nov. 14, 2003;334(1):103-18. (Year: 2003).*

Murphy et al. (Journal of Immunological Methods, vol. 463, p. 127-133, 2018) (Year: 2018).*

Extended European Search Report for EP Application No. 16868096.5 dated Jun. 21, 2019.

Extended European Search Report for EP Application No. EP 16868095 dated Jul. 29, 2019.

Extended European Search Report for EP application No. PCT/IB2016001772 dated May 17, 2019.

Jeffrey et al., "Minor groove binder antibody conjugates employing a water soluable β-glucuronide linker," Bioorganic & Medicinal Chemistry Letters, 17:2278-2280 (2007).

Lee et al., "Enzymatic prenylation and oxime ligation for the synthesis of stable and homogeneous protein-drug conjugates for targeted therapy," Angewandte Chemie, 54(41):12020-12024 (2015).

Lu et al., "Linkers Having a Crucial Role in Antibody—Drug Conjugates," Int J Molec Sci 17(561):1-22 (2016).

Bender et al., "A Mechanistic Pharmacokinetic Model Elucidating the Disposition of Trastuzumab Emtansine (T-DM1), an Antibody-Drug Conjugate (ADC) for Treatment of Metastatic Breast Cancer," The AAPS Journal, 16: 994-1008 (2014).

Collins et al ., "The emergence of oxime click chemistry and its utility in polymer science," Polymer Chemistry, 23: 3812-3826 (2016).

Extended European Search Report for Application No. EP 18774896 dated Dec. 15, 2020.

International Search Report and Written Opinion for International Application No. PCT/IB2020/000649 dated Nov. 27, 2020.

Kim et al., "A dimeric form of a small-sized protein binder exhibits enhanced anti-tumor activity through prolonged blood circulation," Journal of Controlled Release, 279: 282-191 (2018).

Kim et al., "Protein conjugation with genetically encoded unnatural amino acids," Current Opinion in Chemical Biology, 17: 412-419 (2013).

Kim et al., "Strategies and Advancement in Antibody-Drug Conjugate Optimization for Targeted Cancer Therapeutics," Biomolecular Therapeutics, 23: 493-509 (2015).

(56) References Cited

OTHER PUBLICATIONS

Skriec et al., "Non-immunoglobulin scaffolds: a focus on their targets," Trends in Biotechnology, 33(7): 408-418 (2015).
Behrens et al., "Methods for Site-specific Drug Conjugation to Antibodies," MAbs, 6(1): 46-53 (2014).
Bergmann, CP et al. Dental Ceramics. Microstructure, Properties, and Degradation. 2013, Chapter 2, Biomaterials, p. 9.
Carey, FA. Organic Chemistry 6th Ed. McGraw Hill. 2006, chapter 1, p. 9.
Chu et al., "Antibody-drug Conjugates for the Treatment of B-cell Non-Hodgkin's Lymphoma and Leukemia," Future Oncol, 9(3): 355-368 (2013).
Connolly et al., "Discovery of Orally Active 4-amino-6-arylaminopyrimidine-5-carbaldehyde Oximes with Dual EGFR and HER2 Inhibitory Activity," AACR 104th Annual Meeting, Abstract 2456 (2013).
Desbene, S. et al. Doxorubicin prodrugs with reduced cytotoxicity suited for tumour-specific activation. Anti-Cancer Drug Design. 1998,vol. 13,p. 955.
Dunn, PJ. et al. Green Chemistry Principle #8. ACS What is Green Chemistry. Accessed from ACS Website on Jan. 8, 2016.
Extended European Search Report issued by the European Patent Office in corresponding Application No. EP 15799360.1, dated Dec. 21, 2017.
Grinda, M. et al., A Self-Immolative Dendritic Glucuronide Prodrug of Doxorubicin, Medicinal Chemistry Communications, (2012) vol. 3, No. 1, pp. 68-70.
International Search Report and Written Opinion for International Application No. PCT/IB2016/001772 dated Apr. 6, 2017.
International Search Report and Written Opinion for International Application No. PCT/IB2016/001810 dated Apr. 19, 2017.
International Search Report and Written Opinion for International Application No. PCT/IB2016/001811 dated Apr. 19, 2017.
International Search Report and Written Opinion from corresponding International Application Publication No. WO2015182984.
Jeffrey et al., "Development and properties of β-glucuronide linkers for monoclonal antibody-drug conjugates," Bioconjugate Chem, 17:835 (2006).
Kim et al., "Synthesis of Bispecific Antibodies Using Genetically Encoded Unnatural Amino Acids," J Am Chem Soc, 134: 9918-9921 (2012).
Lartigue, "Antibody-Drug Conjugates: Guided Missiles Deployed Against Cancerous Cells," Oncology Live, p. 1 (2012).
Lee et al., "Enzymatic Prenylation and Oxime Ligation for the Synthesis of Stable and Homogeneous Protein-Drug Conjugates for Targeted Therapy," Angew Chem Int Edit, 54: 1-6 (2015).
Leong, KW. Biomaterials. El Sevier. Accessed on Sep. 26, 2016.
McCombs et al., "Antibody Drug Conjugates: Design and Selection of Linker, Payload and Conjugation Chemistry," AAPS J, 17(2): 339-351 (2015).
Merriam-Webster. Biomaterial Definition. Accessed on Sep. 26, 2016.
Tranoy-Opalinski et al., "ß-Glucuronidase-responsive prodrugs for selective cancer chemotherapy: an update," Eur J Med Chem, 74:302-313 (2014).
Wermuth, "Similarity in drugs: reflections on analogue design," Drug Discov Today, 11(Issues 7-8): 248-254 (2006).
Yewale et al., "Epidermal growth factor receptor targeting in cancer: A review of trends and strategies," Biomaterials, 34: 8690-8707 (2013).
U.S. Appl. No. 14/865,778, Issued.
U.S. Appl. No. 14/898,932, Issued.
U.S. Appl. No. 16/005,245, Issued.
U.S. Appl. No. 16/545,869, Issued.
U.S. Appl. No. 15/276,231, Issued.
U.S. Appl. No. 15/276,209, Issued.
U.S. Appl. No. 15/779,446, Pending.
U.S. Appl. No. 15/779,444, Allowed.
U.S. Appl. No. 15/779,450, Allowed.
U.S. Appl. No. 16/328,256, Pending.
U.S. Appl. No. 16/940,326, Pending.
U.S. Appl. No. 16/964,965, Pending.
Christie et al., "Stabilization of cysteine-linked antibody drug conjugates with N-aryl maleimides," Journal of Controlled Release, 220:660-670 (2015).
Gaertner et al., "Chemo-enzymic Backbone Engineering of Proteins ," J. Biol. Chem., 269(10):7224-7230 (1994).
Guan., "Metabolic Activation and Drug Targeting," Drug Delivery: Principles and Applications: 201-244 (2005).
International Search Report and Written Opinion for International Application No. PCT/IB2019/000577 dated Nov. 28, 2019.
Rose et al., "Preparation of well-defined protein conjugates using enzyme-assisted reverse proteolysis," Bioconjugate Chem, 2(3):154-159 (1991).
Sagnou et al., "Design and synthesis of novel pyrrolobenzodiazepine (PBD) prodrugs for ADEPT and GDEPT," Bioorganic and Medicinal Chemistry Letters, 10(18): 2083-2086 (2000).
Schwarz et al., "[15] Enzymatic C-terminal biotinylation of proteins," Methods Enzymol 184:160-162 (1990).
Translation of International Search Report for International Application No. PCT/KR2020/003100 dated Jun. 24, 2020 (4 pages).
Varvounis, "An Update on the Synthesis of Pyrrolo[1,4]benzodiazepines," Molecules, 21(154):1-55 (2016).
Zimmerman et al., "Production of Site-Specific Antibody-Drug Conjugates Using Optimized Non-Natural Amino Acids in a Cell-Free Expression System," Bioconjugate Chem., 25(2):351-361 (2014).
Ai Qaraghuli et al., "Antibody-protein binding and conformational changes: identifying allosteric signaling pathways to engineer a better effector response", Sci Rep 10: 13696 (2020).
Bujak et al., "A Monoclonal Antibody to Human DLK1 Reveals Differential Expression in Cancer and Absence in Healthy Tissues.", Antibodies, 4(2):71-87 (2015).
Dyson et al., "Chemistry of Synthetic Medicinal Substances, N."*World:* 12019 (1964).
Extended European Search Report for EP Application No. 20765639.8 dated Feb. 23, 2023.
Jin et al., "New Technologies Bloom Together for Bettering Cancer Drug Conjugates," Pharmacological Reviews 74: pp. 680-713 (2022).
Lockard et al., "Efficacy and toxicity of the solvent polyethylene glycol 400 in the monkey model." *Epilepsia* 20.1: 77-84 (1979).
Mari et al., "Potential of antibody-drug conjugates (ADCs) for cancer therapy," Cancer Cell International 22(255): pp. 1-12 (2022).
Mariuzza et al., "The structural basis of antigen-antibody recongnition." *Annual review of biophysics and biophsical chemistry* 16.1: 139-159 (1987).
Mashkovsky., "Medicines", Medicine, p. 8, (1993).
Pan et al., "Blocking neuropilin-1 function has an additive effect with anti-VEGF to inhibit tumor growth." *Cancer cell* 11.1:53-67 (2007).
Katoh et al., "Canonical and Non-Canonical WNT Signaling in Cancer Stem Cells and Their Niches: Cellular Heterogeneity, Omics Reprogoramming, Targeted Therapy and Tumor Plasticity (Review)," Int J Oncol, 51(5): pp. 1357-1369 (2017).
U.S. Appl. No. 11/654,197, filed Aug. 16, 2007, Chao et al.

\* cited by examiner

7F1

7F1

COMPOSITIONS AND METHODS RELATED TO ANTI-CD19 ANTIBODY DRUG CONJUGATES

RELATED APPLICATIONS

This application claims the benefit of U.S. Provisional Application No. 62/669,183, filed May 9, 2018, the contents of which are fully incorporated by reference herein.

STATEMENT OF JOINT RESEARCH AGREEMENT

The inventions disclosed herein were made as a result of activities undertaken within the scope of a joint research agreement between LegoChem Biosciences, Inc. and NovImmune, SA., which agreement was in effect on or before the effective filing date of the claimed invention.

SEQUENCE LISTING

The instant application contains a Sequence Listing, which has been submitted via EFS-Web and is hereby incorporated by reference in its entirety. Said ASCII copy is named LCH-00901_SL.txt and is 27,403 bytes in size.

BACKGROUND

Antibody-drug conjugate (ADC) technology is a target-oriented technology, which allows for selective apoptosis of cancer cells. Typically, ADCs function by targeting cancer cells using the antibody and then releasing a toxic material (i.e., the drug) in a cell, thereby triggering cell death. Since ADC technology allows a drug to be accurately delivered to a target cancer cell and released under specific conditions, while minimizing collateral damage to healthy cells, ADC technology increases the efficacy of a therapeutic antibody and decreases the risk of an adverse reaction.

B cells express a wide array of cell surface molecules during their differentiation and proliferation. Examples include the CD10, CD19, CD20, CD21, CD22, CD23, CD24, CD37, CD53, CD72, CD74, CD75, CD77, CD79a, CD79b, CD80, CD81, CD82, CD83, CD84, CD85, and CD86 leukocyte surface markers. These markers have been generally suggested as therapeutic targets for the treatment of B cell disorders or diseases, such as, for example, B cell malignancies, autoimmune diseases, and transplant rejection. CD19 is a surface protein found on B cells and on certain cancerous cells derived from B cells, such as many B cell lymphomas. Anti-CD19 monoclonal antibodies have been generated in mice. However, mouse-derived antibodies are generally immunogenic in humans, and humanized antibodies may be immunogenic in humans.

Accordingly, there exists a need for improved antibody-drug conjugates that target CD19.

SUMMARY OF THE DISCLOSURE

In some aspects, the disclosure relates to antibody-drug conjugates (ADCs). In some embodiments, the disclosure relates to an antibody-drug conjugate, comprising an antibody, a linker, and an active agent (e.g., a drug). The antibody-drug conjugate may comprise a self-immolative group, e.g., for use in releasing an active agent from the antibody and linker.

The disclosure provides monoclonal antibodies and antigen binding fragments or any fragments, variants, multimeric versions, or bispecifics thereof that bind CD19. These antibodies and antigen binding fragments or any fragments, variants, multimeric versions, or bispecifics thereof are collectively referred to herein as anti-CD19 monoclonal antibodies or anti-CD19 mAbs or antigen binding fragments or any fragments, variants, multimeric versions, or bispecifics thereof. Preferably, the monoclonal antibodies and antigen binding fragments or any fragments, variants, multimeric versions, or bispecifics thereof are specific for at least human CD19. In some embodiments, the monoclonal antibodies and antigen binding fragments or any fragments, variants, multimeric versions, or bispecifics thereof that recognize human CD19 are also cross-reactive for at least one other non-human CD19 protein, such as, by way of non-limiting example, non-human primate CD19, e.g., cynomolgus monkey CD19, and/or rodent CD19.

In some aspects, the disclosure relates to antibody-drug conjugates (ADCs) comprising an antibody, at least one branched linker covalently coupled to the antibody, and at least one or two active agents covalently coupled to the branched linker. A branched linker may comprise a branching unit, with at least one drug coupled to the branching unit through a secondary linker; the branching unit is coupled to the antibody by a primary linker. The primary and/or secondary linker may comprise at least one polyethylene glycol unit.

In some aspects, the disclosure relates to an antibody conjugate represented by Formula I, or a pharmaceutically acceptable salt or solvate thereof:

$$\text{Ab-}(X)_y \qquad \text{Formula I}$$

wherein:
Ab is an anti-CD19 antibody or antigen-binding fragment thereof, or a bispecific antibody comprising a first arm that binds CD19, wherein Ab comprises a variable heavy chain complimentary determining region 1 (CDRH1), a variable heavy chain complimentary determining region 2 (CDRH2), a variable heavy chain complimentary determining region 3 (CDRH3), a variable light chain complimentary determining region 1 (CDRL1), a variable light chain complimentary determining region 2 (CDRL2), and a variable light chain complimentary determining region 3 (CDRL3); wherein,
CDRH1 comprises an amino acid sequence of SEQ ID NO: 23 or 29;
CDRH2 comprises an amino acid sequence of SEQ ID NO: 24 or 30;
CDRH3 comprises an amino acid sequence of SEQ ID NO: 25, 26, 27, 28, or 31;
CDRL 1 comprises an amino acid sequence of SEQ ID NO: 32, 37, 41, or 44,
CDRL 2 comprises an amino acid sequence of SEQ ID NO: 33, 38, 42, or 45;
CDRL 3 comprises an amino acid sequence of SEQ ID NO: 34, 35, 36, 40, 43, or 46;
each X is, independently, a chemical moiety comprising an active agent and a linker, wherein the linker links Ab to the active agent; and
y is an integer between 1 to 20.

DETAILED DESCRIPTION OF THE DISCLOSURE

Figure 1A:
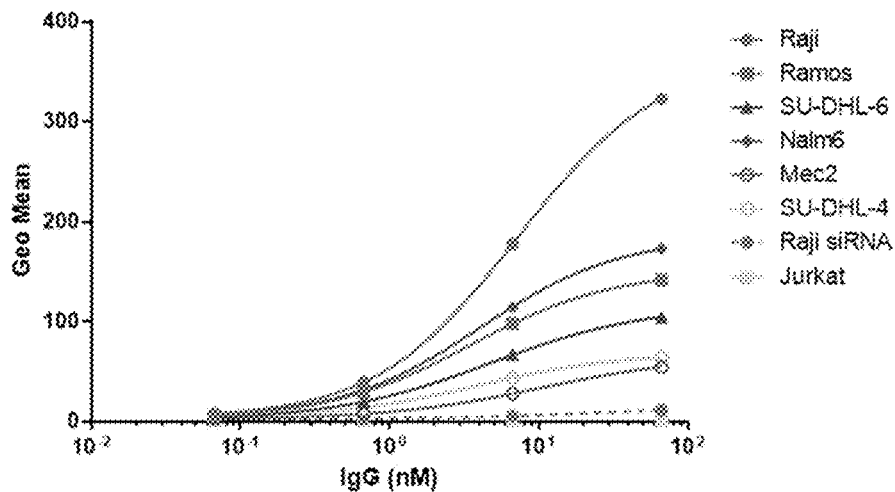
FIGS. 1A-1F are a series of graphs depicting the ability of various anti-CD19 antibodies of the disclosure to bind six different B lymphocyte cell lines (Raji, Ramos, Nalm6, SU-DHL6, SU-DHL4, Mec2), a CD19-silenced cell line (Raji siRNA), and a negative control cell line (Jurkat), as determined by FACS analysis.
Figure 1B:
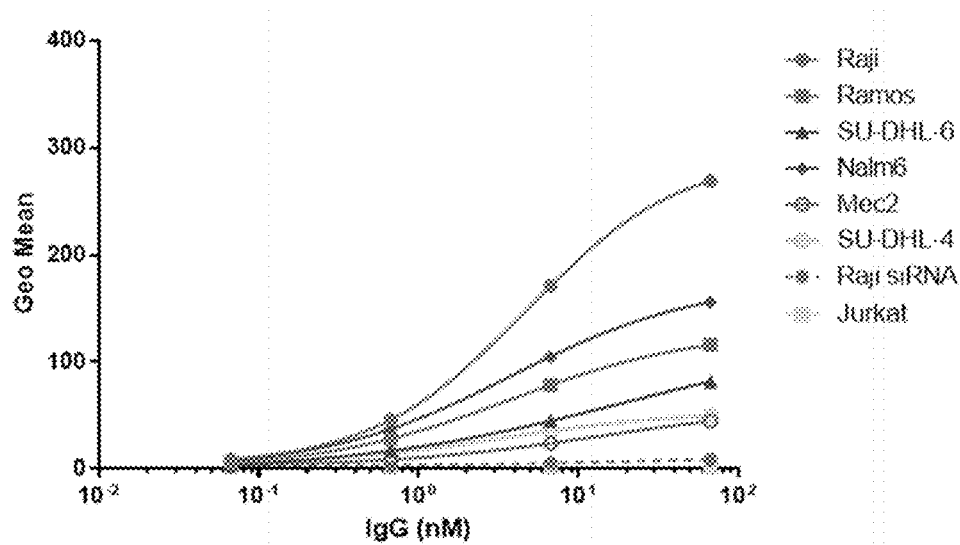
Figure 1C:
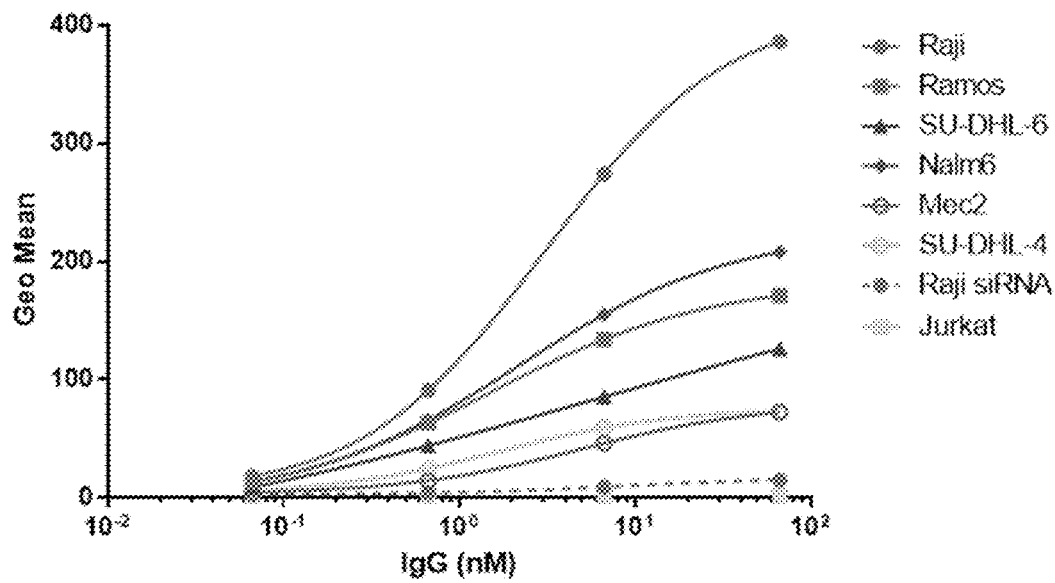
Figure 1D:
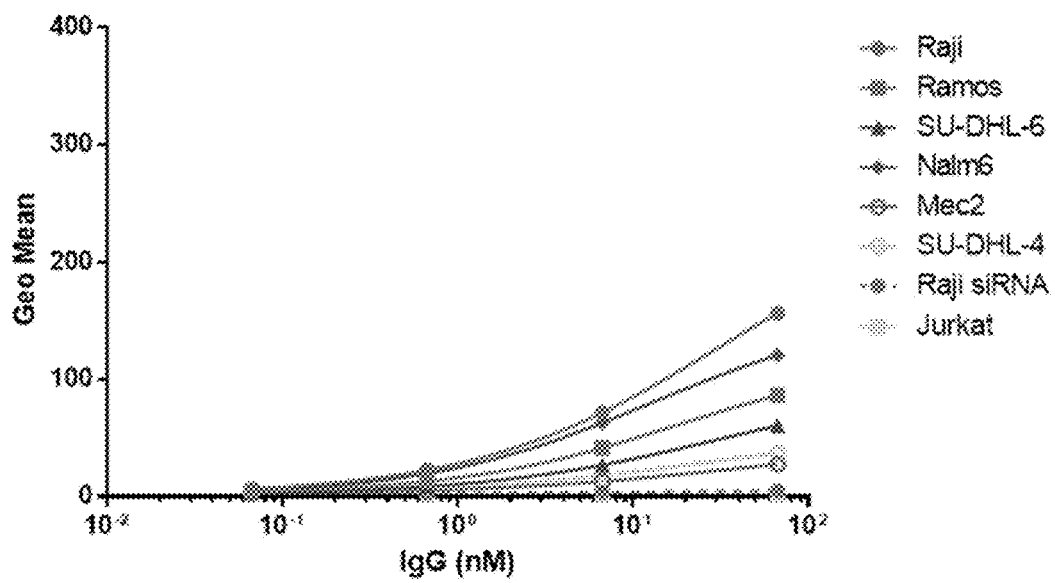
Figure 1E:
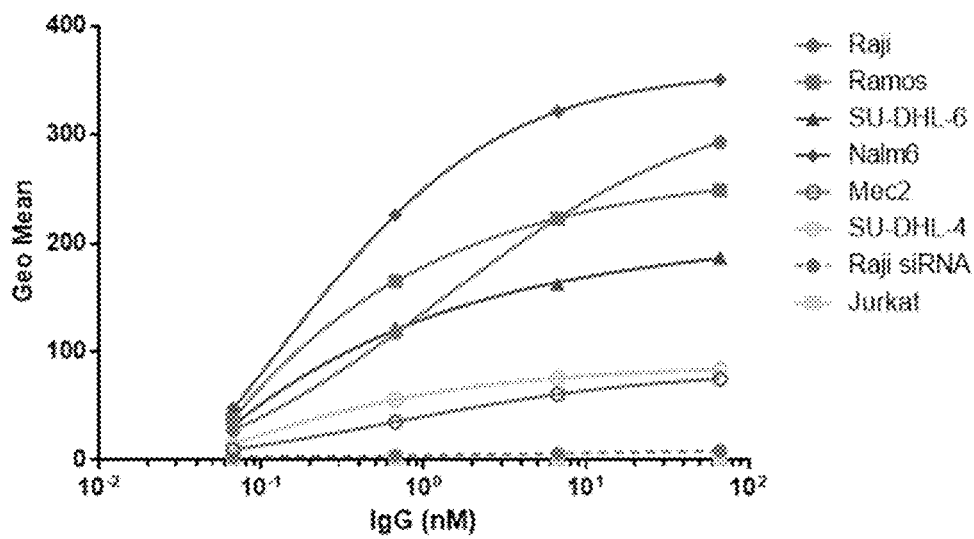
Figure 1F:
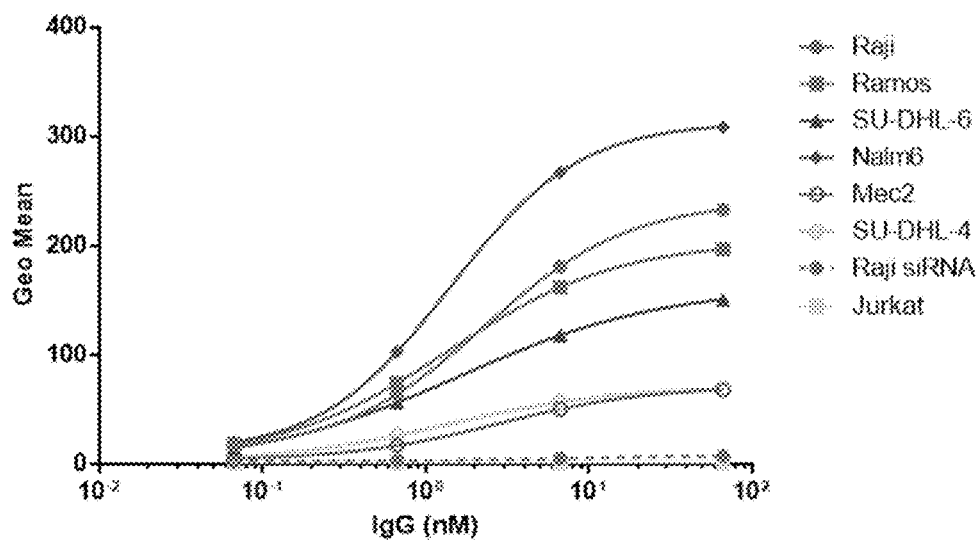

A basic structure of an antibody-drug conjugate is as follows: antibody-linker-low molecular weight drug or toxin. The linker ideally allows the drug to exhibit an effect on a target cancer cell, e.g., after being separated from the antibody (for example, by enzyme-mediated hydrolysis), after the drug reaches a target cell. The linker also plays a functional role, by connecting the antibody and the drug. The efficacy and toxicity of the antibody-drug conjugate depends, in part, on the linker, and thus, the linker plays an important role in drug safety, as described in U.S. Pat. No. 9,919,057, PCT Publication No. WO 2017/089890 and PCT Publication No. WO 2017/089895, the contents of which are fully incorporated by reference herein.

The linkers of antibody-drug conjugates may be roughly classified as non-cleavable or cleavable. Many non-cleavable linkers are attached to antibodies using a thioether, comprising a cysteine of the antibody. The pendant drug generally cannot dissociate from the antibody in vivo. In the case of the widely-used thiol-maleimide method, however, the antibody-drug conjugate is unstable, which may result in dissociation of the drug from the conjugate before or after it reaches a target cell.

Cleavable linkers are linkers that may be hydrolyzed, for example, by a lysosomal enzyme. A cleavable linker may comprise a disulfide bond, e.g., including a cysteine of the antibody. A disulfide linker, which allows for dissociation via a thiol exchange reaction, relies in part on the uptake of an antibody-drug conjugate into a target cell and the exposure of the disulfide to the cytosol, which is a reducing environment. Since various types of thiols (for example, albumin, and glutathione) are present in the blood, however, a drug may dissociate from the antibody prior to reaching its target.

Recently, a new approach to making antibody-drug conjugates has been described, using protein prenylation of a C-terminal amino acid sequence to install a modified isoprenoid unit that allows for attachment of a drug or other active agent to the antibody in a mild and site-specific manner (e.g., U.S. Patent Publication No. 2012/0308584, which is fully incorporated by reference herein). Further refinement is possible, and descriptions of additional cleavable linkers may be found in the following: U.S. Pat. No. 9,919,057, PCT Publication No. WO 2017/089890 and PCT Publication No. WO 2017/089895, the contents of which are fully incorporated by reference herein.

The disclosure provides antibody-drug conjugates of antibodies that bind CD19. These antibodies include anti-CD19 monoclonal antibodies or anti-CD19 mAbs, as well as their antigen-binding fragments, and are described in U.S. patent application Ser. No. 15/804,517, published as US 2018/0142018 A1, the contents of which are fully incorporated by reference herein. Preferably, the monoclonal antibodies are specific for at least human CD19. In some embodiments, the monoclonal antibodies that recognize human CD19 are also cross-reactive for at least one other non-human CD19 protein, such as, by way of non-limiting example, non-human primate CD19, e.g., cynomolgus monkey CD19, and/or rodent CD19. The disclosure also includes antibodies that bind to the same epitope as an anti-CD19 monoclonal antibody disclosed herein.

The disclosure also provides monovalent antibodies and/or bispecific antibodies that include at least a first arm that is specific for CD19. Preferably, the monovalent antibodies and/or bispecific antibodies are specific for at least human CD19. In some embodiments, the monovalent antibodies and/or bispecific antibodies that recognize human CD19 are also cross-reactive for at least one other non-human CD19 protein, such as, by way of non-limiting example, non-human primate CD19, e.g., cynomolgus monkey CD19, and/or rodent CD19. The disclosure also provides antibodies that bind to the same epitope as an anti-CD19 monovalent and/or an anti-CD19 bispecific antibody disclosed herein.

The bispecific antibodies of the disclosure allow for simultaneous binding of the two antibody arms to two antigens on the surface of the cell (termed co-engagement), which results in additive or synergistic increase of affinity due to avidity mechanism. As a consequence, co-engagement confers high selectivity towards cells expressing both antigens as compared to cells that express just one single antigen. In addition, the affinities of the two arms of a bispecific antibody to their respective targets can be set up in a way that binding to target cells is principally driven by one of the antibody arms. In some embodiments, the bispecific antibody includes a first arm that binds CD19 and a second arm that binds a second target that is not CD19. In some embodiments, the bispecific antibody includes a first arm that binds CD19 and a second arm that binds a tumor associated antigen (TAA). In some embodiments, the bispecific antibody includes a first arm that binds CD19 and a second arm that binds a tumor associated antigen (TAA), where the first arm binds to CD19 with high affinity, and the second arm binds to the TAA with low affinity. In some embodiments, the TAA is an antigen that is expressed on the cell surface of a cancer cell. In some embodiments, the cancer cell is selected from a lung cancer cell, a bronchial cancer cell, a prostate cancer cell, a breast cancer cell, a colorectal cancer cell, a pancreatic cancer cell, an ovarian, a leukemia cancer cell, a lymphoma cancer cell, an esophageal cancer cell, a liver cancer cell, a urinary and/or bladder cancer cell, a renal cancer cell, an oral cavity cancer cell, a pharyngeal cancer cell, a uterine cancer cell, and/or a melanoma cancer cell. In some embodiments, suitable second targets include, by way of non-limiting example, CD47, CD20, CD22, CD40, BAF1-R, CD5, CD32b, ICOSL, IL6R, and/or IL21R.

In some embodiments, the bispecific antibody is a fully human bispecific IgG format, such as the κλ-body format described in PCT Publication No. WO 2012/023053, the contents of which are incorporated by reference herein in their entirety.

Exemplary anti-CD19 monoclonal antibodies of the disclosure and antigen binding fragments thereof include, for example, the 5F5 antibody, the 7F11 antibody, the 9G8 antibody, the F6 antibody, the 7F1 antibody, and the 10D8 antibody or an antigen binding fragment thereof.

Exemplary anti-CD19 bispecific antibodies of the disclosure in which at least one binding site is specific for CD19 include, for example, the 5F5 antibody, the 7F11 antibody, the 9G8 antibody, the F6 antibody, the 7F1 antibody, and the 10D8 antibody or an antigen binding fragment thereof.

In some embodiments, exemplary anti-CD19 monoclonal antibodies of the disclosure and antigen binding fragments thereof include a combination of heavy chain complementarity determining regions (CDRs) selected from the CDR sequences shown in Table 1 and light chain CDRs selected from the CDR sequences shown in Table 2, where the CDRs shown in Tables 1 and 2 are defined according to the IMGT nomenclature.

In some embodiments, exemplary anti-CD19 monoclonal, monospecific anti-CD19 antibodies, anti-CD19 monovalent antibodies, and/or bispecific antibodies of the disclosure include a combination of heavy chain complementarity determining regions (CDRs) selected from the CDR sequences shown in Table 1 and light chain CDRs selected from the CDR sequences shown in Table 2, where the CDRs shown in Tables 1 and 2 are defined according to the IMGT nomenclature.

TABLE 1

Anti-CD19 Heavy Chain CDRs

| Antibody | CDRH1 | CDRH2 | CDRH3 |
|---|---|---|---|
| 5F5 | GYSFTSYW (SEQ ID NO: 23) | IYPGDSDT (SEQ ID NO: 24) | ARGISGIYNLHGFDI (SEQ ID NO: 25) |
| 7F11 | GYSFTSYW (SEQ ID NO: 23) | IYPGDSDT (SEQ ID NO: 24) | ARGVSGIYNLHGFDI (SEQ ID NO: 26) |
| 9G8 | GYSFTSYW (SEQ ID NO: 23) | IYPGDSDT (SEQ ID NO: 24) | ARGVSGIYNLHGFDI (SEQ ID NO: 26) |
| F6 | GYSFTSYW (SEQ ID NO: 23) | IYPGDSDT (SEQ ID NO: 24) | ARVWYYDFWSGADAFDI (SEQ ID NO: 27) |
| 7F1 | GYSFTSYW (SEQ ID NO: 23) | IYPGDSDT (SEQ ID NO: 24) | ARGDYWTGFAY (SEQ ID NO: 28) |
| 10D8 | GGTFSSYA (SEQ ID NO: 29) | IIPIFGTA (SEQ ID NO: 30) | ARDRGYDYVWGSYRYGAFDI (SEQ ID NO: 31) |

TABLE 2

Anti-CD19 Light Chain CDRs

| Antibody | CDRL1 | CDRL2 | CDRL3 |
|---|---|---|---|
| 5F5 | QSISSY (SEQ ID NO: 32) | AAS (SEQ ID NO: 33) | QQASLDSPLT (SEQ ID NO: 34) |
| 7F11 | QSISSY (SEQ ID NO: 32) | AAS (SEQ ID NO: 33) | QQGMWDNPFT (SEQ ID NO: 35) |
| 9G8 | QSISSY (SEQ ID NO: 32) | AAS (SEQ ID NO: 33) | QQGRFGSPFT (SEQ ID NO: 36) |
| F6 | QSVSSN (SEQ ID NO: 37) | GAS (SEQ ID NO: 38) | QQGSLEAPQT (SEQ ID NO: 40) |
| 7F1 | SSNIGNNY (SEQ ID NO: 41) | DNN (SEQ ID NO: 42) | GTWDLGWNSV (SEQ ID NO: 43) |
| 10D8 | SSDVGGYNY (SEQ ID NO: 44) | EVS (SEQ ID NO: 45) | SSYDVWVPHMV (SEQ ID NO: 46) |

In one aspect, the antibody-drug conjugates disclosed herein are represented by Formula I or a pharmaceutically acceptable salt or solvate thereof:

$$Ab\text{-}(X)_y \qquad \text{Formula I}$$

wherein:
Ab is an anti-CD19 antibody or antigen-binding fragment thereof, or a bispecific antibody comprising a first arm that binds CD19, wherein Ab comprises a variable heavy chain complimentary determining region 1 (CDRH1), a variable heavy chain complimentary determining region 2 (CDRH2), a variable heavy chain complimentary determining region 3 (CDRH3), a variable light chain complimentary determining region 1 (CDRL1), a variable light chain complimentary determining region 2 (CDRL2), and a variable light chain complimentary determining region 3 (CDRL3); wherein
CDRH1 comprises an amino acid sequence of SEQ ID NO: 23 or 29;
CDRH2 comprises an amino acid sequence of SEQ ID NO: 24 or 30;
CDRH3 comprises an amino acid sequence of SEQ ID NO: 25, 26, 27, 28, or 31;
CDRL1 comprises an amino acid sequence of SEQ ID NO: 32, 37, 41, or 44,
CDRL2 comprises an amino acid sequence of SEQ ID NO: 33, 38, 42, or 45;
CDRL3 comprises an amino acid sequence of SEQ ID NO: 34, 35, 36, 40, 43, or 46;
each X is, independently, a chemical moiety comprising one or more active agents and a linker, wherein the linker links Ab to the active agent(s); and
y is an integer between 1 to 20.

In some embodiments, Ab is a monoclonal antibody, a domain antibody (dAb), a single chain antibody (scAb), a Fab fragment, a F(ab')2 fragment, a single chain variable fragment (scFv), a scFv-Fc fragment, a single domain heavy chain antibody, a single domain light chain antibody, a variant antibody, a multimeric antibody, or a bispecific antibody. Ab may be a rabbit, mouse, chimeric, humanized or fully human monoclonal antibody. In some embodiments, Ab is an IgG isotype, such as an IgG1 isotype.

In some embodiments, Ab comprises a combination of a variable heavy chain comprising the amino acid sequence of SEQ ID NO: 2, 6, 12, 16, or 20, and a variable light chain comprising the amino acid sequence of SEQ ID NO: 4, 8, 10, 14, 18, or 22.

In some embodiments, Ab comprises a combination of a variable heavy chain sequence and a variable light chain sequence selected from:
(a) a variable heavy chain comprising the amino acid sequence of SEQ ID NO: 2 and a variable light chain comprising the amino acid sequence of SEQ ID NO: 4;
(b) a variable heavy chain comprising the amino acid sequence of SEQ ID NO: 6, and a variable light chain comprising the amino acid sequence of SEQ ID NO: 8;
(c) a variable heavy chain comprising the amino acid sequence of SEQ ID NO: 6 and a variable light chain comprising the amino acid sequence of SEQ ID NO: 10;
(d) a variable heavy chain comprising the amino acid sequence of SEQ ID NO: 12 and a variable light chain comprising the amino acid sequence of SEQ ID NO: 14;
(e) a variable heavy chain comprising the amino acid sequence of SEQ ID NO: 16 and a variable light chain comprising the amino acid sequence of SEQ ID NO: 18; and
(f) a variable heavy chain comprising the amino acid sequence of SEQ ID NO: 20 and a variable light chain comprising the amino acid sequence of SEQ ID NO: 22.

In some embodiments, the anti-CD19 antibody is 5F5, 7F11, 9G8, F6, 7F1 or 10D8. In some embodiments, the CD19 is human CD19.

Preferably, the link between Ab and the active agent is cleavable. Generally, the linker is represented by Formula II:

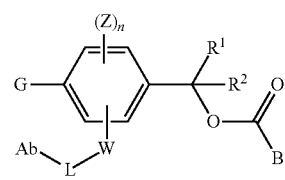

Formula II

G is a glucuronic acid moiety or

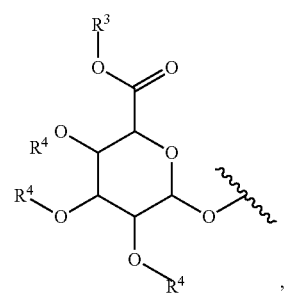

wherein $R^3$ is hydrogen or a carboxyl protecting group, and each $R^4$ is independently hydrogen or a hydroxyl protecting group;
B is an active agent;
$R^1$ and $R^2$ are each independently hydrogen, $C_{1-8}$ alkyl, or $C_{3-8}$ cycloalkyl; or
W is —C(O)—, —C(O)NR'—, —C(O)O—, —SO$_2$NR'—, —P(O)R''NR'—, —SONR'—, or —PO$_2$NR'—, wherein the C, S, or P is directly bound to the phenyl ring, and R' and R'' are each independently hydrogen, $C_{1-8}$ alkyl, $C_{3-8}$ cycloalkyl, $C_{1-8}$ alkoxy, $C_{1-8}$ alkylthio, mono- or di-$C_{1-8}$ alkylamino, $C_{3-20}$ heteroaryl or $C_{6-20}$ aryl;
each instance of Z is, independently, $C_{1-8}$ alkyl, halogen, cyano, or nitro;
n is an integer of 0 to 3; and
L is a linker connecting Ab and W.

In some embodiments, L is $C_{1-50}$ alkylene or 1-50 atom heteroalkylene. In some embodiments, L satisfies at least one of the following:
(i) L includes at least one unsaturated bond;
(ii) two atoms within L are substituted with a bivalent substituent such that the substituent; with the atoms that it bridges, completes a heteroarylene;
(iii) L is a 1-50 atom heteroalkylene; or
(iv) the alkylene is substituted with one or more $C_{1-20}$ alkyls.

In some embodiments, L includes at least one isoprenyl derivative unit represented by Formula III, which is recognized by an isoprenoid transferase:

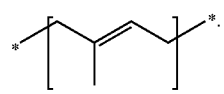

Formula III

In some such embodiments, the linker is represented by Formula II:

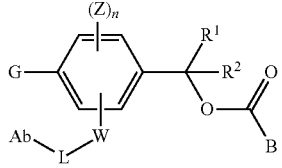

Formula II

G is a glucuronic acid moiety or

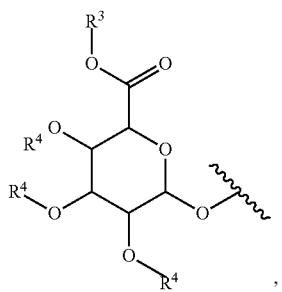

wherein $R^3$ is hydrogen or a carboxyl-protecting group, and each $R^4$ is independently hydrogen or a hydroxyl-protecting group;

B is the active agent;

$R^1$ and $R^2$ are each independently hydrogen, $C_{1-8}$ alkyl, or $C_{3-8}$ cycloalkyl; or W is —C(O)—, —C(O)NR'—, —C(O)O—, —SO$_2$NR'—, —P(O)R"NR'—, —SONR'—, or —PO$_2$NR'—, wherein the C, S, or P is directly bound to the phenyl ring, and R' and R" are each independently hydrogen, $C_{1-8}$ alkyl, $C_{3-8}$ cycloalkyl, $C_{1-8}$ alkoxy, $C_{1-8}$ alkylthio, mono- or di-$C_{1-8}$ alkylamino, $C_{3-20}$ heteroaryl or $C_{6-20}$ aryl;

each instance of Z is, independently, $C_{1-8}$ alkyl, halogen, cyano, or nitro;

n is an integer of 0 to 3;

wherein either:

A) L is $C_{1-50}$ alkylene or 1-50 atom heteroalkylene and satisfies at least one of the following:
(i) L includes at least one unsaturated bond;
(ii) two atoms within L are substituted with a bivalent substituent such that the substituent, with the atoms that it bridges, completes a heteroarylene;
(iii) L is a 1-50 atom heteroalkylene;
(iv) the alkylene is substituted with one or more $C_{1-20}$ alkyls; or B) L includes at least one isoprenyl derivative unit represented by Formula III, which is recognized by an isoprenoid transferase:

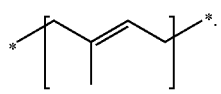

Formula III

In some embodiments, G is

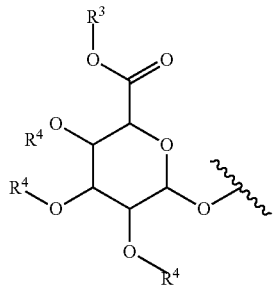

$R^3$ is hydrogen or a carboxyl-protecting group; and each $R^4$ is independently hydrogen or a hydroxyl-protecting group. In some preferred embodiments, each $R^1$ and $R^2$ is hydrogen.

In some embodiments, each Z, independently, is $C_{1-8}$ alkyl, halogen, cyano, or nitro. In some preferred embodiments, n is 0.

In some embodiments, W is —C(O)—, —C(O)NR'—, —C(O)O—, —SO$_2$NR'—, —P(O)R"NR'—, —SONR'—, or —PO$_2$NR'—, wherein the C, S, or P is directly bound to the phenyl ring, and R' and R" are each independently hydrogen, $C_{1-8}$ alkyl, $C_{3-8}$ cycloalkyl, $C_{1-8}$ alkoxy, $C_{1-8}$ alkylthio, mono- or di-$C_{1-8}$ alkylamino, $C_{3-20}$ heteroaryl or $C_{6-20}$ aryl. In some preferred embodiments, W is —C(O)—, —C(O)NR'—, or —C(O)O—. In some even further preferred embodiments, W is —C(O)NR'—, wherein C(O) is bonded to the phenyl ring and NR' is bonded to L.

In some embodiments, G is

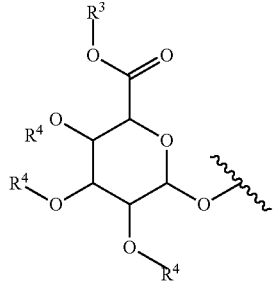

W is —C(O)NR'—, wherein C(O) is bonded to the phenyl ring and NR' is bonded to L; and $R^1$ and $R^2$ each represent hydrogen.

In some embodiments, L is $C_{1-50}$ alkylene or 1-50 atom heteroalkylene and satisfies at least one of the following:
(i) L includes at least one unsaturated bond;
(ii) two atoms within L are substituted with a bivalent substituent such that the substituent; with the atoms that it bridges, completes a heteroarylene;
(iii) L is a 1-50 atom heteroalkylene; and
(iv) the alkylene is substituted with one or more $C_{1-20}$ alkyls.

In some embodiments, L comprises an oxime, and the at least one polyethylene glycol unit covalently links the oxime to the active agent.

In some embodiments, L is a nitrogen-containing 1-50 atom heteroalkylene, the linker comprises at least two atoms of a hydrophilic amino acid, and the nitrogen forms a peptide bond with a carbonyl of the hydrophilic amino acid.

In some preferred embodiments, W represents —C(O)NR'—, and the nitrogen of W is a nitrogen atom of a hydrophilic amino acid. In some embodiments, the hydrophilic amino acid is an amino acid that comprises a side chain having a moiety that bears a charge at neutral pH in aqueous solution. In some embodiments, the hydrophilic amino acid is arginine, aspartate, asparagine, glutamate, glutamine, histidine, lysine, ornithine, proline, serine, or threonine. In some preferred embodiments, the hydrophilic amino acid is arginine, aspartate, asparagine, glutamate, glutamine, histidine, lysine, ornithine, proline, serine, or threonine. In some preferred embodiments, the hydrophilic amino acid is aspartate or glutamate. In other preferred embodiments, the hydrophilic amino acid is ornithine or lysine. In yet other preferred embodiments, the hydrophilic amino acid is arginine. In some embodiments, the amino acid covalently links an oxime of the linker to a polyethylene glycol unit of the linker.

In some embodiments, the linker comprises a peptide and the peptide comprises at least one hydrophilic amino acid, preferably an amino acid having a side chain having a moiety that bears a charge at neutral pH in aqueous solution (e.g., an amine, guanidine, or carboxyl moiety). In some embodiments, each amino acid of the peptide is independently selected from alanine, aspartate, asparagine, glutamate, glutamine, glycine, lysine, ornithine, proline, serine, and threonine. In some embodiments, the peptide comprises at least one aspartate or glutamate.

In some preferred embodiments, W represents —C(O)NR'—, and the nitrogen of W is a nitrogen of the N-terminal amino acid in the peptide.

In some embodiments, the peptide covalently links an oxime of the linker to a polyethylene glycol unit of the linker.

In some embodiments, the peptide comprises 2 to 20 amino acids.

In some embodiments, the linker is covalently bound to Ab by a thioether bond, and the thioether bond comprises a sulfur atom of a cysteine of the Ab. In some embodiments, Ab comprises an amino acid motif, preferably at a C-terminus of Ab, that is recognized by an isoprenoid transferase; and the thioether bond comprises a sulfur atom of a cysteine of the amino acid motif.

In some embodiments, the amino acid motif is a sequence CYYX;
C represents cysteine;
Y, independently for each occurrence, represents an aliphatic amino acid, such as alanine, isoleucine, leucine, methionine, or valine;
X, independently for each occurrence, represents glutamine, glutamate, serine, cysteine, methionine, alanine, or leucine; and
the thioether bond comprises a sulfur atom of a cysteine of the amino acid motif.

In some embodiments, the amino acid motif is a sequence CVIM or CVLL.

In some embodiments, at least one of the seven amino acids preceding the amino acid motif is glycine. In some embodiments, at least three of the seven amino acids preceding the amino acid motif are each independently selected from glycine and proline. In some embodiments, at least three of the seven amino acids preceding the amino acid motif are each independently selected from glycine, aspartic acid, arginine, and serine. In some embodiments, each of the one, two, three, four, five, six, seven, eight, nine, or ten amino acids preceding the amino acid motif is glycine. In some preferred embodiments, L comprises the amino acid sequence GGGGGGGGCVIM, preferably at a C-terminus.

In some embodiments, L comprises at least one isoprenyl derivative unit represented by Formula III, which is recognized by an isoprenoid transferase:

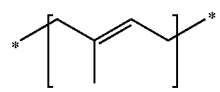

Formula III

In some embodiments, L is a 3-50 heteroalkylene comprising an oxime, wherein:
the oxygen atom of the oxime is on the side of L that is linked to W and the carbon atom of the oxime is on the side of L that is linked to Ab; or
the carbon atom of the oxime is on the side of L that is linked to W and the oxygen atom of the oxime is on the side of L that is linked to Ab.

In some preferred embodiments, L comprises an oxime, and the at least one isoprenyl unit covalently links the oxime to Ab. In some embodiments, L comprises:

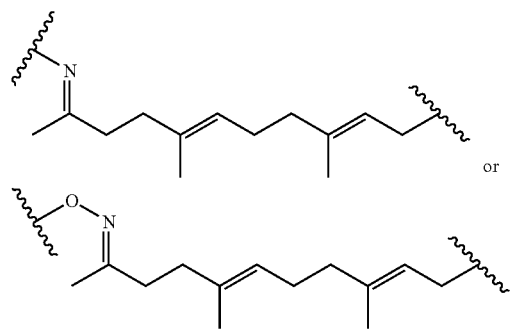

or

In some embodiments, L comprises:

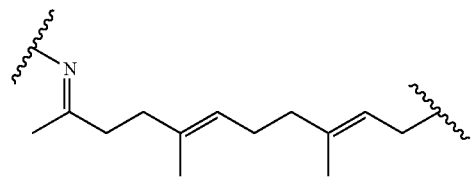

In some preferred embodiments, L comprises:

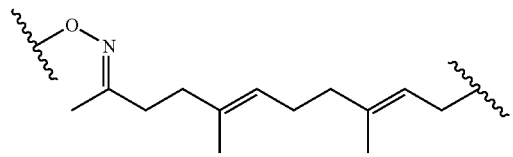 [SMILES: *C/C=C(\C)CC/C=C(\C)CC/C(C)=N/O*]

In some embodiments, L further comprises a connection unit represented by Formula VIII or IX:

    Formula VIII,

    Formula IX;

V is a single bond, —O—, —S—, —NR²¹—, —C(O)NR²²—, —NR²³C(O)—, —NR²⁴SO₂—, or —SO₂NR²⁵—;

X is —O—, $C_{1-8}$ alkylene, or —NR$^{21}$—;

$R^{21}$ to $R^{25}$ are each independently hydrogen, $C_{1-6}$ alkyl, $C_{1-6}$ alkyl $C_{6-20}$ aryl, or $C_{1-6}$ alkyl $C_{3-20}$ heteroaryl;

r is an integer of 1 to 10;

p is an integer of 0 to 12;

q is an integer of 1 to 20; and w is an integer of 1 to 20.

In some embodiments, q is an integer from 4 to 20. In some embodiments, q is an integer from 2 to 12. In some embodiments, q is an integer from 6 to 20. In some embodiments, q is 2, 5 or 11. In some embodiments, r is 2. In some embodiments, p is 2. In some preferred embodiments, V is —O—. In some embodiments, r is 2; p is 2; q is 2, 5, or 11; and V is —O—. In some preferred embodiments, X is —O—.

In some embodiments, w is an integer from 6 to 20. In some embodiments, L comprises at least one polyethylene glycol unit, represented by either

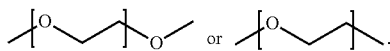

In some embodiments, L comprises 1 to 12 —OCH$_2$CH$_2$— units. In some embodiments, L comprises 3 to 12 —OCH$_2$CH$_2$— units. In some embodiments, L comprises 5 to 12 —OCH$_2$CH$_2$— units. In some embodiments, L comprises 6 or 12 —OCH$_2$CH$_2$— units. In some preferred embodiments, L comprises 3 —OCH$_2$CH$_2$— units.

In some embodiments, L comprises an oxime, and the at least one polyethylene glycol unit covalently links the oxime to the active agent. In some embodiments, L comprises a binding unit formed by a 1,3-dipolar cycloaddition reaction, hetero-Diels-Alder reaction, nucleophilic substitution reaction, non-aldol type carbonyl reaction, addition to carbon-carbon multiple bond, oxidation reaction, or click reaction.

Click chemistry reactions are carried out in a mild condition, thereby making it possible to easily handle proteins. The click chemistry reaction shows significantly high reaction specificity. Therefore, even though a protein has other functional groups (for example, a side chain residue, or at a C- or N-terminal), these functional groups are not affected by the click chemistry reaction. For example, a click chemistry reaction between an azide group and an acetylene group of a protein may occur while other functional groups of the protein are not affected by the click chemistry reaction. Further, the click chemistry reaction may specifically occur regardless of the kind of involved ligand. In some cases, the ligand may be selected so as to improve overall reaction efficiency. For example, an azide-acetylene click chemistry reaction may produce triazole with a high yield (ref: Rhiannon K. Hia et al, Chem. Rev. 2009, 109, 5620; Morten Meldal and Christian Wenzel Tornoe, Chem Rev., 2008, 108, 2952; Hartmuth C. Kolb et al, Angew. Chemie Int. Ed. Engl., 2001, 40, 2004, which are all incorporated herein by reference).

In some embodiments, the binding unit is formed by a reaction between acetylene and azide, or a reaction between an aldehyde or ketone group and a hydrazine or alkoxyamine.

In some embodiments, L further includes a binding unit represented by Formula IV, V, VI, or VII:

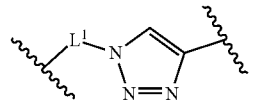

Formula IV

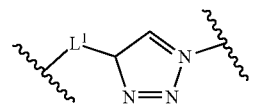

Formula V

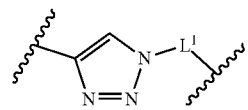

Formula VI

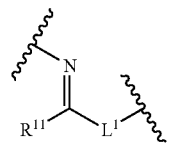

Formula VII $L^1$ is a single bond or $C_{1-30}$ alkylene; and $^{11}$ is hydrogen or $C_{1-10}$ alkyl.

In some embodiments, $L^1$ is a single bond. In other embodiments, $L^1$ is a $C_{11}$ alkylene. In yet other embodiments, $L^1$ is a $C_{12}$ alkylene.

In some embodiments, L comprises:

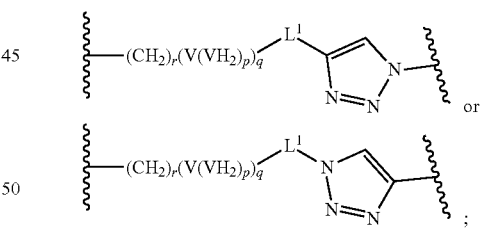

V is a single bond, —O—, —S—, —NR$^{21}$—, —C(O)NR$^{22}$—, —NR$^{23}$C(O)—, —NR$^{24}$SO$_2$—, or —SO$_2$NR$^{25}$—, preferably —O—;

$R^{21}$ to $R^{25}$ are each independently hydrogen, $C_{1-6}$ alkyl, $C_{1-6}$ alkyl $C_{6-20}$ aryl, or $C_{1-6}$ alkyl $C_{3-20}$ heteroaryl;

r is an integer from 1 to 10;

p is an integer from 0 to 10;

q is an integer from 1 to 20; and $L_1$ is a single bond.

In some embodiments, r is 2 or 3. In some embodiments, p is 1 or 2. In some embodiments, q is 1 to 6. In some embodiments, r is 2 or 3; p is 1 or 2; and q is 1 to 6.

In some embodiments, the linker comprises:

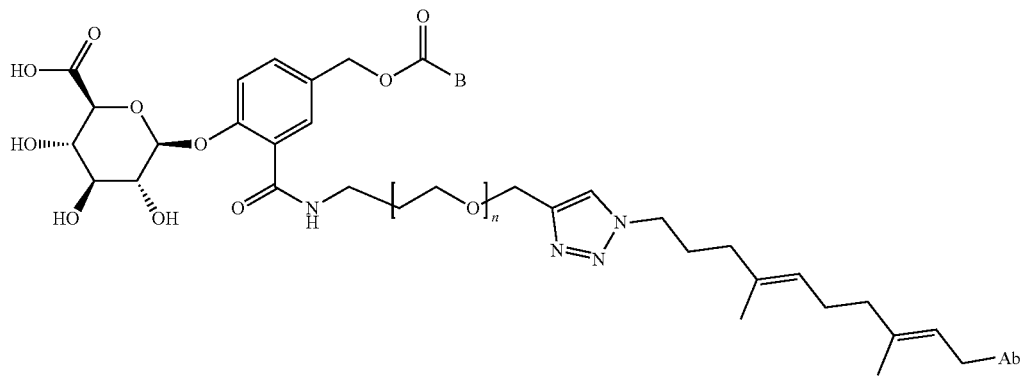

wherein Ab represents an anti-CD19 antibody; B represents the active agent; and n is an integer from 1 to 20.

In other embodiments, the linker comprises:

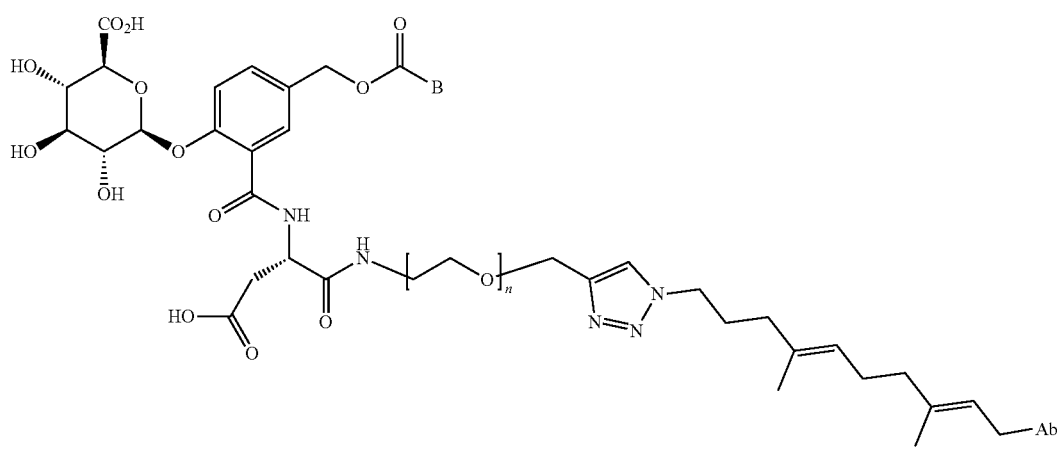

wherein Ab represents an anti-CD19 antibody; B represents the active agent; and n is an integer from 1 to 20.

In yet other embodiments, the linker comprises:

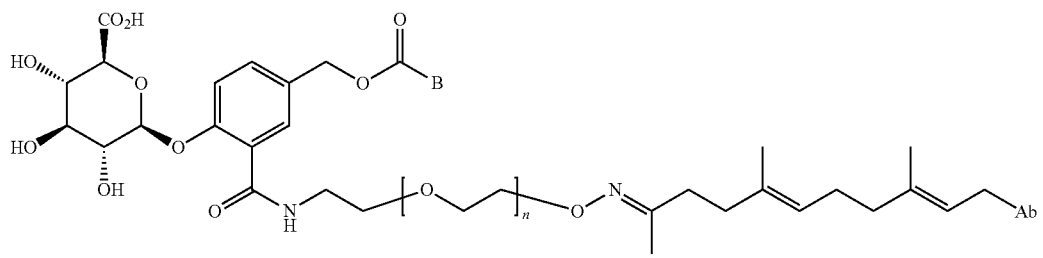

wherein Ab represents an anti-CD19 antibody; B represents the active agent; and n is an integer from 0 to 20.

In yet other embodiments, the linker comprises:

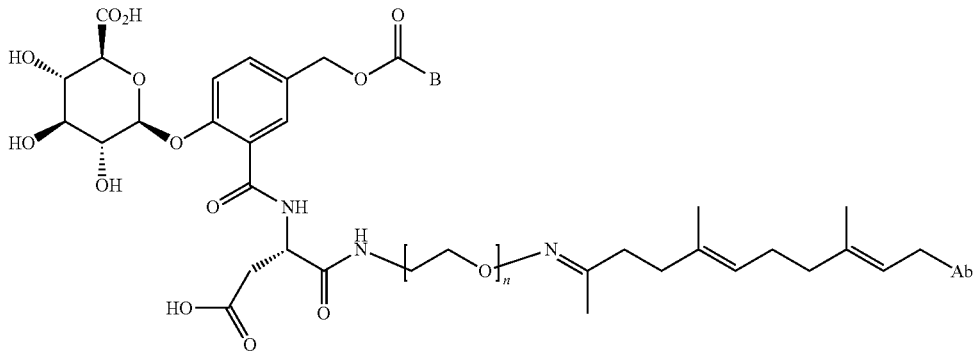

wherein Ab represents an anti-CD19 antibody; B represents the active agent; and n is an integer from 1 to 20.

In some embodiments, the isoprenoid transferase is farnesyl protein transferase (FTase) or geranylgeranyl transferase (GGTase).

In some embodiments, L further comprises

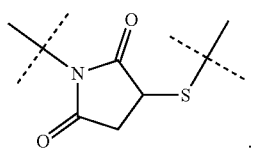

In some embodiments,

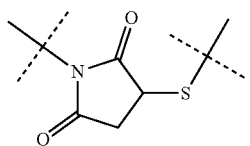

is a binding moiety.

In some embodiments, L comprises one or more branched linkers covalently coupled to Ab, wherein:
i) each branched linker comprises a branching unit (BR) covalently coupled to Ab by a primary linker (PL);
ii) each branched linker comprises a first branch (B1), which couples a first active agent to the branching unit and comprises a secondary linker (SL) and a cleavage group (CG); and
iii) each branched linker further comprises a second branch (B2), in which either a) a second active agent is covalently coupled to the branching unit by a secondary linker (SL) and a cleavage group (CG); orb) a polyethylene glycol moiety is covalently coupled to the branching unit, and
wherein each cleavage group can be hydrolyzed to release the active agent from the antibody conjugate.

In some embodiments, at least one branching unit has the structure

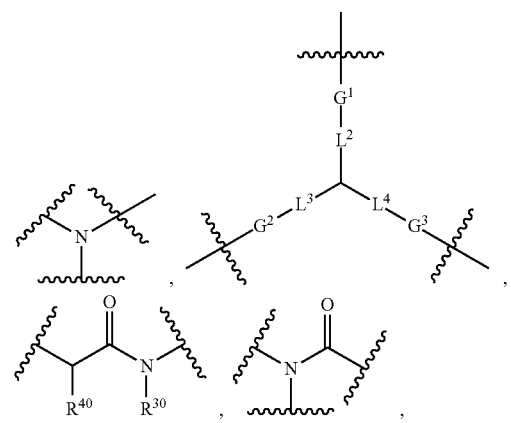

wherein $L^2$, $L^3$, $L^4$ is each independently a direct bond or $-C_nH_{2n}-$ where n is a integer of 1 to 30, wherein $G^1$, $G^2$, $G^3$ is each independently a direct bond,

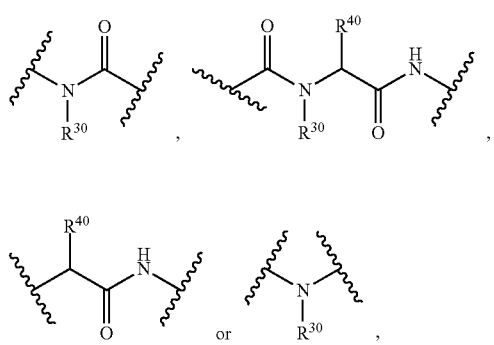

wherein $R^{30}$ is hydrogen or $C_{1-30}$ alkyl; and wherein $R^{405}$—COOR$^{50}$, wherein L5 is a direct bond or $C_{1-10}$ alkylene, and $R^{50}$ is hydrogen or $C_{1-30}$ alkyl.

In yet other embodiments, the linker comprises:

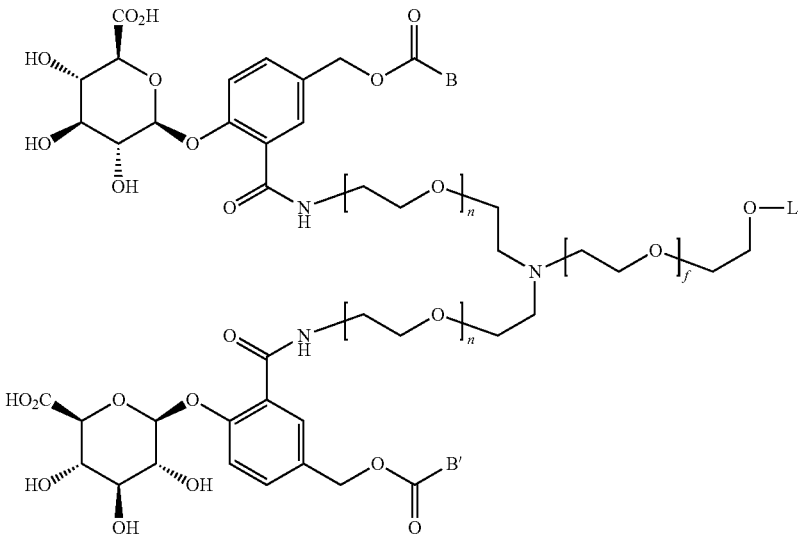

wherein:

B and B' represent active agents, which may be the same or different;

n, independently for each occurrence, represents an integer from 0 to 30;

f, independently for each occurrence, represents an integer from 0 to 30; and

L represents a linkage to the Ab.

In some embodiments, n is an integer from 1 to 10. In some embodiments, n is an integer from 4 to 20.

In some embodiments, the cleavage group is capable of cleaving within a target cell. In some embodiments, the cleavage group is capable of releasing one or more active agents. In some embodiments, the antibody conjugate comprises Ab; at least one branched linker covalently coupled to Ab; and at least two active agents covalently coupled to the branched linker. In some embodiments, at least two branched linkers are coupled to Ab, and each branched linker is coupled to at least two active agents. In some embodiments, three branched linkers are coupled to Ab. In other embodiments, four branched linkers are coupled to Ab. In yet other embodiments, exactly one branched linker is coupled to Ab. In yet other embodiments, each branched linker is coupled to exactly two active agents. In some embodiments, the conjugate comprises at least two different active agents. In some embodiments, at least one branched linker is coupled to two different active agents.

In some embodiments, each active agent is coupled to a branched linker by a cleavable (e.g., hydrolysable) bond. In some embodiments, each branched linker comprises a branching unit, and each active agent is coupled to the branching unit through a secondary linker and the branching unit is coupled to the anti-CD19 antibody by a primary linker. In some embodiments, the branching unit is a nitrogen atom, e.g., of an amine or an amide. In some embodiments, the branching unit is an amide and the primary linker comprises the carbonyl of the amide. In some embodiments, the branching unit is an amide and the secondary linker comprises the carbonyl of the amide. In some preferred embodiments, the branching unit is a lysine unit.

In some preferred embodiments, B is an active agent. In some embodiments, the active agent is independently selected from chemotherapeutic agents and toxins. In some embodiments, the active agent is an immunomodulatory compound, an anticancer agent, an antiviral agent, an antibacterial agent, an antifungal agent, an antiparasitic agent, or a combination thereof.

In some embodiments, each active agent is independently selected from:

(a) erlotinib, bortezomib, fulvestrant, sutent, letrozole, imatinib mesylate, PTK787/ZK 222584, oxaliplatin, 5-fluorouracil, leucovorin, rapamycin, lapatinib, lonafarnib, sorafenib, gefitinib, AG1478, AG1571, thiotepa, cyclophosphamide, busulfan, improsulfan, piposulfan, benzodopa, carboquone, meturedopa, uredopa, ethylenimine, altretamine, triethylenemelamine, trietylenephosphormide, triethiylenethiophosphoramide, trimethylolomelamine, bullatacin, bullatacinone, camptothecin, topotecan, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, sarcodictyin, spongistatin, chlorambucil, chlornaphazine, cholophosphamide, estramustine, ifosfamide, mechlorethamine, melphalan, novembichin, phenesterine, prednimustine, trofosfamide, uracil mustard, carmustine, chlorozotocin, fotemustine, lomustine, nimustine, ranimnustine, calicheamicin, calicheamicin gamma 1, calicheamicin omega 1, dynemicin, dynemicin A, clodronate, esperamicin, neocarzinostatin chromophore, aclacinomysins, actinomycin, antrmycin, azaserine, bleomycins, cactinomycin, carabicin, carninomycin, carzinophilin, chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubucin, liposomal doxorubicin, deoxydoxorubicin, epirubicin, esorubicin, marcellomycin, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, zorubicin, 5-fluorouracil, denopterin, methotrexate, pteropterin, trimetrexate, fludarabine, 6-mercaptopurine, thiamiprine, thiguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, polysaccharide-k, razoxane, rhizoxin, sizofiran, spirogermanium, tenuazonic acid, triaziquone, 2,2',2"-trichlorotriethylamine, T-2 toxin, verracurin A, roridin A, and anguidine, urethane, vindesine, dacarbazine, mannomustine, mitobronitol, mitolactol, pipobroman, gacytosine, arabinoside, cyclophosphamide, thiotepa, paclitaxel, albumin-engineered nanoparticle formulation of paclitaxel, doxetaxel, chlorambucil, gemcitabine, 6-thioguanine, mercaptopurine, cisplatin, carboplatin, vinblastine, platinum, etoposide, ifosfamide, mitoxantrone, vincristine, vinorelbine, novantrone, teniposide, edatrexate, daunomycin, aminopterin, xeloda, ibandronate, CPT-11, topoisomerase inhibitor RFS 2000, difluoromethylornithine, retinoic acid, capecitabine, or pharmaceutically acceptable salts, solvates or acids of any of the foregoing;

(b) monokine, a lymphokine, a traditional polypeptide hormone, parathyroid hormone, thyroxine, relaxin, prorelaxin, a glycoprotein hormone, follicle stimulating hormone, thyroid stimulating hormone, luteinizing hormone, hepatic growth factor fibroblast growth factor, prolactin, placental lactogen, tumor necrosis factor-α, tumor necrosis factor-β, mullerian-inhibiting substance, mouse gonadotropin-associated peptide, inhibin, activin, vascular endothelial growth factor, thrombopoietin, erythropoietin, an osteoinductive factor, an interferon, interferon-α, interferon-β, interferon-γ, a colony stimulating factor ("CSF"), macrophage-CSF, granulocyte-macrophage-CSF, granulocyte-CSF, an interleukin ("IL"), IL-1, IL-1a, IL-2, IL-3, IL-4, IL-5, IL-6, IL-7, IL-8, IL-9, IL-10, IL-11, IL-12, a tumor necrosis factor, TNF-α, TNF-β, a polypeptide factor, LIF, kit ligand, or a combination of any of the foregoing;

(c) diphtheria toxin, botulium toxin, tetanus toxin, dysentery toxin, cholera toxin, amanitin, amanitin derivatives, α-amanitin, pyrrolobenzodiazepine, pyrrolobenzodiazepine derivatives, tetrodotoxin, brevetoxin, ciguatoxin, ricin, AM toxin, auristatin, tubulysin, geldanamycin, maytansinoid, calicheamicin, daunomycin, doxorubicin, methotrexate, vindesine, SG2285, dolastatin, a dolastatin analog, cryptophycin, camptothecin, camptothecin derivatives and metabolites, rhizoxin, a rhizoxin derivative, CC-1065, a CC-1065 analogue or derivative, duocarmycin, an enediyne antibiotic, esperamicin, epothilone, azonafide, aplidine, a toxoid, or a combination of any of the foregoing;

(d) an affinity ligand, wherein the affinity ligand is a substrate, an inhibitor, a stimulating agent, a neurotransmitter, a radioisotope, or a combination of any of the foregoing;

(e) a radioactive label, $^{32}P$, $^{35}S$, a fluorescent dye, an electron dense reagent, an enzyme, biotin, streptavidin, dioxigenin, a hapten, an immunogenic protein, a nucleic acid molecule with a sequence complementary to a target, or a combination of any of the foregoing;

(f) an immunomodulatory compound, an anti-cancer agent, an anti-viral agent, an anti-bacterial agent, an anti-fungal agent, and an anti-parasitic agent, or a combination of any of the foregoing;

(g) tamoxifen, raloxifene, droloxifene, 4-hydroxytamoxifen, trioxifene, keoxifene, LY117018, onapristone, or toremifene;

(h) 4(5)-imidazoles, aminoglutethimide, megestrol acetate, exemestane, letrozole, or anastrozole;

(i) flutamide, nilutamide, bicalutamide, leuprolide, goserelin, or troxacitabine;

(j) an aromatase inhibitor;

(k) a protein kinase inhibitor;

(l) a lipid kinase inhibitor;

(m) an antisense oligonucleotide;

(n) a ribozyme;

(o) a vaccine; and (p) an anti-angiogenic agent.

In some embodiments, Ab is an anti-CD19 antibody;

the active agent is a pyrrolobenzodiazepine dimer;

the linker links Ab to the N10 or N'10 position of the pyrrolobenzodiazepine dimer; and y is an integer between 1 to 20.

In some embodiments, the active agent is a pyrrolobenzodiazepine dimer;

the pyrrolobenzodiazepine dimer is substituted at the N10 position with X or at the N'10 position with X', wherein X or X' link the pyrrolobenzodiazepine dimer to the linker;

X and X' are each independently selected from —C(O)O—*, —S(O)O—*, —C(O)—*, —C(O)NR$^X$—*, —S(O)$_2$NR$^X$—*, —(P(O)R')NR$^X$—*, —S(O)NR$^X$—*, or —PO$_2$NR$^X$—*;

R$^X$ is H, C$_{1-8}$ alkyl, C$_{3-8}$ cycloalkyl, C$_{3-20}$ heteroaryl, or C$_{5-20}$ aryl;

R$^{X'}$ is OH, N3, CN, SH, C$_{1-8}$ alkyl, C$_{3-8}$ cycloalkyl, C$_{1-8}$ alkoxy, C$_{1-8}$ alkylthio, C$_{3-20}$ heteroaryl, C$_{5-20}$ aryl, or amino; and

* represents the attachment point between the pyrrolobenzodiazepine dimer and the linker.

In some embodiments, X and X' are each independently selected from —C(O)O—*, —C(O)—* or —C(O)NR$^X$—*.

In some embodiments, wherein the pyrrolobenzodiazepine dimer is represented by Formula X or Formula XI:

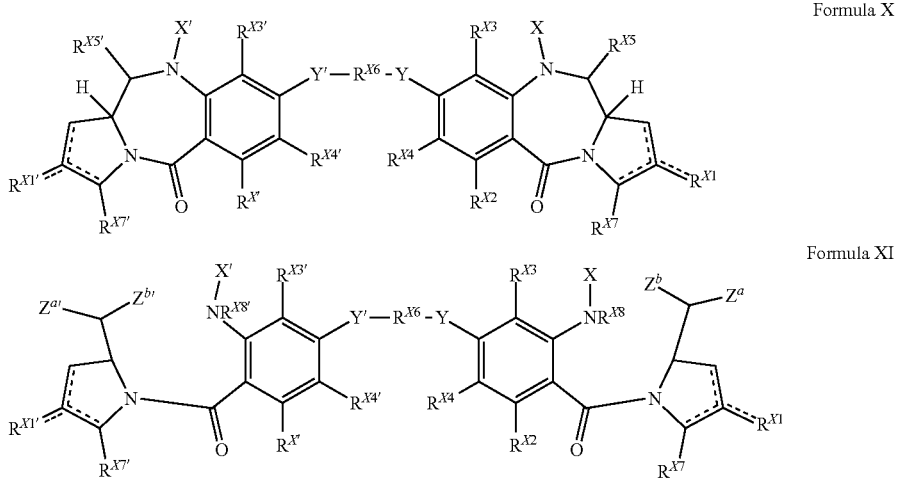

Formula X

Formula XI wherein:
the dotted lines indicate the optional presence of a double bond between C1 and C2, or between C2 and C3; and between C'1 and C'2, or between C'2 or C'3;

$R^{X1}$ and $R^{X1'}$ are independently selected from H, OH, =O, =CH$_2$, CN, R$'''$, OR$'''$, =CH—R$'''$, =C(R$'''$)$_2$, O—SO$_2$—R$'''$, CO$_2$R$'''$, COR$'''$, halo and dihalo, R$'''$ is independently selected from R$'''$, CO$_2$R$'''$, COR$'''$, CHO, CO$_2$H, and halo, each R$'''$ is independently selected from C$_{1-12}$ alkyl, C$_{2-12}$ alkenyl, C$_{2-12}$ alkynyl, C$_{5-20}$ aryl, C$_{5-20}$ heteroaryl, C3-6 cycloalkyl, 3 to 7-membered heterocyclyl, 3 to 7-membered heterocycloalkyl, and 5 to 7-membered heteroaryl;

$R^{X2}$, $R^{X2'}$, $R^{X3}$, $R^{X3'}$, $R^{X5}$, and $R^{X5'}$ are each independently selected from H, R$'''$, OH, OR$'''$, SH, SR$'''$, NH$_2$, NHR$'''$, NR$'''_2$, NO$_2$, Me$_3$Sn and halo;

$R^{X4}$ and $R^{X4'}$ are independently selected from H, R$'''$, OH, OR$'''$, SH, SR$'''$, NH$_2$, NHR$'''$, NR$'''_2$, NO$_2$, Me$_3$Sn, halo, C$_{1-6}$ alkyl, C$_{1-6}$ alkoxy, C$_{2-6}$ alkenyl, C$_{2-6}$ alkynyl, C$_{3-6}$ cycloalkyl, 3 to 7-membered heterocycloalkyl, C$_{5-12}$ aryl, 5 to 7-membered heteroaryl, —CN, —NCO, —OR$''$, —OC(O)R$''$, —OC(O)NR$''$R$'''$, —OS(O)R$''$, —OS(O)$_2$R$''$, —SR$''$, —S(O)R$''$, —S(O)$_2$R$''$, —S(O)NR$''$R$'''$, —S(O)$_2$NR$''$R$'''$, —OS(O)NR$''$R$'''$, —OS(O)$_2$NR$''$R$'''$, —NR$''$R$'''$, —NR$''$C(O)R$°$, —NR$''$C(O)OR$°$, —NR$''$C(O)NR$°$R$°'$, —NR$''$S(O)R$°$, —NR$''$S(O)$_2$R$°$, —NR$''$S(O)NR$°$R$°'$, —NR$''$S(O)$_2$NR$°$R$°'$, —C(O)R$''$, —C(O)OR$''$ and —C(O)NR$''$R$'''$;

$R^X$ and $R^{X'}$ are independently selected from H, OH, N$_3$, CN, NO$_2$, SH, NH$_2$, ONH$_2$, NHNH$_2$, halo, C$_{1-8}$ alkyl, C$_{3-8}$ cycloalkyl, C$_{1-8}$ alkoxy, C$_{1-8}$ alkylthio, C$_{3-20}$ heteroaryl, C$_{5-20}$ aryl or mono- or di-C$_{1-8}$ alkylamino;

Y and Y' are independently selected from O, S, and N(H);

$R^{X6}$ is C$_{3-12}$ alkylene, C$_{3-12}$ alkenylene, or C$_{3-12}$ heteroalkylene;

$R^{X7}$ and $R^{X7'}$ are independently selected from H, C$_{1-6}$ alkyl, C$_{2-6}$ alkenyl, C$_{2-6}$ alkynyl, C$_{3-6}$ cycloalkyl, 3 to 7-membered heterocycloalkyl, C$_{6-10}$ aryl, 5 to 7-membered heteroaryl, —OR$^r$, —OC(O)R$^r$, —OC(O)NR$^r$R$^{r'}$, —OS(O)R$^r$, —OS(O)$_2$R$^r$, —SR$^r$, —S(O)R$^r$, —S(O)$_2$R$^r$, —S(O)NR$^r$R$^{r'}$, —S(O)$_2$NR$^r$R$^{r'}$, —OS(O)NR$^r$R$^{r'}$, —OS(O)$_2$NR$^r$R$^{r'}$, —NR$^r$R$^{r'}$, —NR$^r$C(O)R$^s$, —NR$^r$C(O)OR$^s$, —NR$^r$C(O)NR$^s$R$^{s'}$, —NR$^r$S(O)R$^s$, —NR$^r$S(O)$_2$R$^s$, —NR$^r$S(O)NR$^s$R$^{s'}$, —NR$^r$S(O)$_2$NR$^s$R$^{s'}$, —C(O)R$^r$, —C(O)OR$^s$ or —C(O)NR$^r$R$^{r'}$;

each R$^r$, R$^{r'}$, R$^s$, and R$^{s'}$ is independently selected from H, C$_{1-7}$ alkyl, C$_{2-7}$ alkenyl, C$_{2-7}$ alkynyl, C$_{3-13}$ cycloalkyl, 3 to 7-membered heterocycloalkyl, C$_{5-10}$ aryl, and 5 to 7-membered heteroaryl;

each $R^{X8}$ and $R^{X8'}$ is independently selected from H, C$_{1-6}$ alkyl, C$_{2-6}$ alkenyl, C$_{2-6}$ alkynyl, C$_{3-6}$ heteroalkyl, 3 to 7-membered heterocycloalkyl, C$_{5-10}$ aryl, 5 to 7-membered heteroaryl, —S(O)R$'''$, —S(O)$_2$R$'''$, —S(O)NR$'''$R$''''$, —S(O)$_2$NR$'''$R$''''$, —NR$'''$R$''''$, —NR$'''$C(O)R$'''$, —NR$'''$C(O)OR$''$, —NR$'''$C(O)NR$''$R$'''$, —NR$'''$S(O)R$''$, —NR$'''$S(O)$_2$R$''$, —NR$'''$S(O)NR$''$R$'''$, —NR$'''$S(O)$_2$NR$''$R$'''$, —C(O)R$'''$, —C(O)OR$'''$ and —C(O)NR$'''$R$''''$, $Z^a$ is selected from OR$^{X12a}$, NR$^{X12a}$R$^{X12a}$, or SR$^{X12a}$;
$Z^b$ is selected from OR$^{X13a}$, NR$^{X13a}$R$^{X13a}$, or SR$^{X13a}$;
$Z^{a'}$ is selected from OR$^{X12a}$, NR$^{X12a}$R$^{X12a}$, or SR$^{X12a}$;
$Z^{b'}$ is selected from OR$^{X13a'}$, NR$^{X13a'}$R$^{X13a'}$, or SR$^{X13a'}$;

each of $R^{X12a}$, $R^{X12a'}$, $R^{X13a}$, and $R^{X13a'}$ is independently selected from absent, H, C$_{1-6}$ alkyl, C$_{2-6}$ alkenyl, C$_{2-6}$ alkynyl, C$_{3-6}$ cycloalkyl, 3 to 7-membered heterocycloalkyl, C$_{5-10}$ aryl, 5 to 7-membered heteroaryl, —C(O)R$^{X15a}$, —C(O)OR$^{X15a}$ and —C(O)NR$^{X15a}$R$^{X15a}$; and each $R^{X15a}$ and $R^{X15a'}$ is independently selected from C$_{1-12}$ alkyl, C$_{2-12}$ alkenyl, C$_{2-12}$ alkynyl, C$_{5-20}$ aryl, C$_{5-20}$ heteroaryl, C3-6 cycloalkyl, 3 to 7-membered heterocyclyl, 3 to 7-membered heterocycloalkyl, and 5 to 7-membered heteroaryl;

wherein $R^{X13a}$ and $R^{X14a}$ taken together with the atoms to which they are attached optionally combine to form a 3 to 7-membered heterocyclyl, 3 to 7-membered heterocycloalkyl, or 3 to 7-membered heteroaryl; and $R^{X13a'}$ and $R^{X14a'}$ taken together with the atoms to which they are attached optionally combine to form a 3 to 7-membered heterocyclyl, 3 to 7-membered heterocycloalkyl, or 3 to 7-membered heteroaryl; and wherein each R$''$, R$'''$, R$°$, R$°'$, R$^p$, and R$^{p'}$ is independently selected from H, C$_{1-7}$ alkyl, C$_{2-7}$ alkenyl, C$_{2-7}$ alkynyl, C$_{3-13}$ cycloalkyl, 3 to 7-membered heterocycloalkyl, C$_{5-10}$ aryl, and 5 to 7-membered heteroaryl.

In some embodiments, each R$'''$ is independently selected from C$_{1-12}$ alkyl, C$_{2-12}$ alkenyl, C$_{2-12}$ alkynyl, C$_{5-20}$ aryl, C$_{5-20}$ heteroaryl, C3-6 cycloalkyl, 3 to 7-membered heterocyclyl, 3 to 7-membered heterocycloalkyl, and 5 to 7-membered heteroaryl, wherein, when R$'''$ optionally substituted with one or more C$_{1-12}$ alkyl, C$_{2-12}$ alkenyl, C$_{2-12}$ alkynyl, C$_{5-20}$ aryl, C$_{5-20}$ heteroaryl, $C_{3-6}$ cycloalkyl, 3 to 7-membered heterocyclyl, 3 to 7-membered heterocycloalkyl, or 5 to 7-membered heteroaryl.

In some embodiments, $R^{X4}$ and $R^{X4'}$ are independently selected from H, $R^m$, OH, $OR^m$, SH, $SR^m$, $NH_2$, $NHR^m$, $NR^m R^{m'}$, $NO_2$, $Me_3Sn$, halo, $C_{1-6}$ alkyl, $C_{1-6}$ alkoxy, $C_{2-6}$ alkenyl, $C_{2-6}$ alkynyl, $C_{3-6}$ cycloalkyl, 3 to 7-membered heterocycloalkyl, $C_{5-12}$ aryl, 5 to 7-membered heteroaryl, —CN, —NCO, —$OR^n$, —$OC(O)R^n$, —$OC(O)NR^n R^{n'}$, —$OS(O)R^n$, —$OS(O)_2R^n$, —$SR^n$, —$S(O)R^n$, —$S(O)_2R^n$, —$S(O)NR^n R^{n'}$, —$S(O)_2NR^n R^{n'}$, —$OS(O)NR^n R^{n'}$, —$OS(O)_2NR^n R^{n'}$, —$NR^n R^{n'}$, —$NR^n C(O)R^o$, —$NR^n C(O)OR^o$, —$NR^n C(O)NR^o R^{o'}$, —$NR^n S(O)R^o$, —$NR^n S(O)_2R^o$, —$NR^n S(O)NR^o R^{o'}$, —$NR^n S(O)_2 NR^o R^{o'}$, —$C(O)R^n$, —$C(O)OR^n$ and —$C(O)NR^n R^{n'}$, wherein, when $R^{X4}$ or $R^{X4'}$ is $C_{1-6}$ alkyl, $C_{1-6}$ alkoxy, $C_{2-6}$ alkenyl, $C_{2-6}$ alkynyl, $C_{3-6}$ cycloalkyl, 3 to 7-membered heterocycloalkyl, $C_{5-12}$ aryl, 5 to 7-membered heteroaryl, it is optionally substituted with one or more $C_{1-6}$ alkyl, $C_{1-6}$ alkoxy, $C_{2-6}$ alkenyl, $C_{2-6}$ alkynyl, $C_3$-$C_6$ cycloalkyl, 3 to 7-membered heterocycloalkyl, $C_{5-10}$ aryl, 5 to 7-membered heteroaryl, —$OR^p$, —$OC(O)R^p$, —$OC(O)NR^p R^{p'}$, —$OS(O)R^p$, —$OS(O)_2R^p$, —$SR^p$, —$S(O)R^p$, —$S(O)_2R^p$, —$S(O)NR^p R^{p'}$, —$S(O)_2NR^p R^{p'}$, —$OS(O)NR^p R^{p'}$, —$OS(O)_2NR^p R^{p'}$, —$NR^p R^{p'}$, —$NR^p C(O)R^q$, —$NR^p C(O)OR^q$, —$NR^p C(O)NR^q R^{q'}$, —$NR^p S(O)R^q$, —$NR^p S(O)_2 R^q$, —$NR^p S(O)NR^q R^{q'}$, —$NR^p S(O)_2 NR^q R^{q'}$, —$C(O)R^p$, —$C(O)OR^p$ or —$C(O)NR^p R^p$.

In some embodiments, $R^{X7}$ and $R^{X7'}$ are independently selected from H, $C_{1-6}$ alkyl, $C_{2-6}$ alkenyl, $C_{2-6}$ alkynyl, $C_{3-6}$ cycloalkyl, 3 to 7-membered heterocycloalkyl, $C_{6-10}$ aryl, 5 to 7-membered heteroaryl, —$OR^r$, —$OC(O)R^r$, —$OC(O)NR^r R^{r'}$, —$OS(O)R^r$, —$OS(O)_2 R^r$, —$SR^r$, —$S(O)R^r$, —$S(O)_2 R^r$, —$S(O)NR^r R^{r'}$, —$S(O)_2 NR^r R^{r'}$, —$OS(O)NR^r R^{r'}$, —$OS(O)_2 NR^r R^{r'}$, —$NR^r C(O)R^s$, —$NR^r C(O)OR^s$, —$NR^r C(O)NR^s R^{s'}$, —$NR^r S(O)R^s$, —$NR^r S(O)_2 R^s$, —$NR^r S(O)NR^s R^{s'}$, —$NR^r S(O)_2 NR^s R^s$, —$C(O)R^r$, —$C(O)OR^s$ or —$C(O)NR^r R^{r'}$, wherein, when $R^{X7}$ or $R^{X7'}$ is $C_{1-6}$ alkyl, $C_{2-6}$ alkenyl, $C_{2-6}$ alkynyl, $C_{3-6}$ cycloalkyl, 3 to 7-membered heterocycloalkyl, $C_{6-10}$ aryl, 5 to 7-membered heteroaryl, it is optionally substituted with one or more $C_{1-6}$ alkyl, $C_{2-6}$ alkenyl, $C_{2-6}$ alkynyl, $C_{3-6}$ cycloalkyl, 3 to 7-membered heterocycloalkyl, $C_{6-10}$ aryl, 5 to 7-membered heteroaryl, —$OR^t$, —$OC(O)R^t$, —$OC(O)NR^t R^{t'}$, —$OS(O)R^t$, —$OS(O)_2 R^t$, —$SR^t$, —$S(O)R^t$, —$S(O)_2 R^t$, —$S(O)NR^t R^{t'}$, —$S(O)_2 NR^t R^{t'}$, —$OS(O)NR^t R^{t'}$, —$OS(O)_2 NR^t R^{t'}$, —$NR^t C(O)R^u$, —$NR^t C(O)OR^u$, —$NR^t C(O)NR^u R^{u'}$, —$NR^t S(O)R^u$, —$NR^t S(O)_2 R^u$, —$NR^t S(O)NR^u R^{u'}$, —$NR^t S(O)_2 NR^u R^{u'}$, —$C(O)R^t$, —$C(O)OR^t$ or —$C(O)NR^t R^{t'}$, wherein, each of $R^r$, $R^{r'}$, $R^s$, $R^{s'}$, $R^t$, $R^{t'}$, $R^u$ and $R^{u'}$ is independently selected from H, $C_{1-7}$ alkyl, $C_{2-7}$ alkenyl, $C_{2-7}$ alkynyl, $C_{3-13}$ cycloalkyl, 3 to 7-membered heterocycloalkyl, $C_{5-10}$ aryl, and 5 to 7-membered heteroaryl.

In some embodiments, $R^{X1}$ and $R^{X1'}$ are independently selected from $R^m$; and $R^m$ is selected from $C_{1-6}$ alkyl, $C_{2-6}$ alkenyl, $C_{5-7}$ aryl and $C_{3-6}$ heteroaryl.

In some embodiments, $R^{X2}$, $R^{X2'}$, $R^{X3}$, $R^{X3'}$, $R^{X5}$, and $R^{X5'}$ are independently selected from H or OH.

In some embodiments, $R^{X4}$ and $R^{X4'}$ are independently selected from $R^m$; and $R^m$ is $C_{1-6}$ alkoxy. In some preferred embodiments, $R^{X4}$ and $R^{X4'}$ are independently selected from methoxy, ethoxy, or butoxy. In some embodiments, Y and Y' are O.

In some embodiments, $R^{X6}$ is $C_{3-12}$ alkylene, $C_{3-12}$ alkyenylene, $C_{3-12}$ heteroalkylene, wherein:

$R^{X6}$ is substituted with —$NH_2$, —$NHR^m$, —$NHC(O)R^m$, —$NHC(O)CH_2$—$[OCH_2CH_2]_n$—$R^{XX}$, or —$[CH_2CH_2O]_n$—$R^{XX}$;

wherein $R^{XX}$ is selected from H, OH, $N_3$, CN, $NO_2$, SH, $NH_2$, $ONH_2$, $NHNH_2$, halo, $C_{1-8}$ alkyl, $C_{3-8}$ cycloalkyl, $C_{1-8}$ alkoxy, $C_{1-8}$ alkylthio, $C_{3-20}$ heteroaryl, $C_{5-20}$ aryl or mono- or di-$C_{1-8}$ alkylamino; and n is an integer between 1 to 6.

In some embodiments, the active agent is a pyrrolobenzodiazepine dimer represented by Formula XII or Formula XIII:

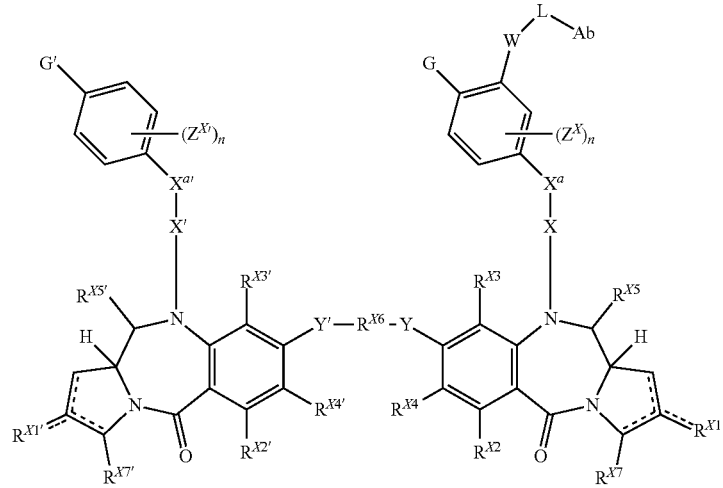

Formula XII

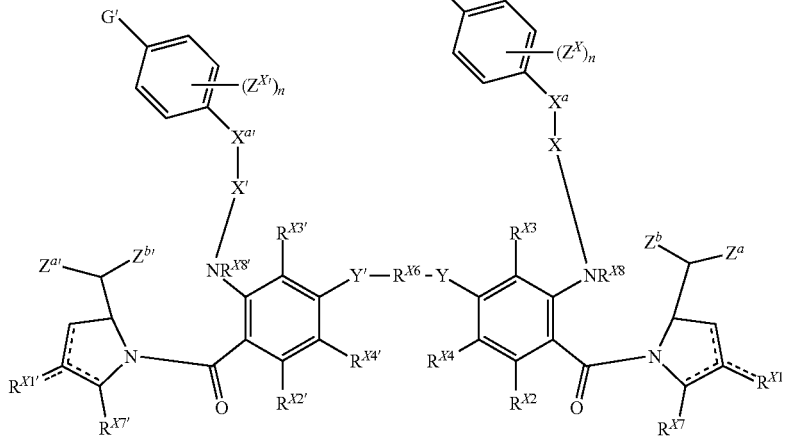

Formula XIII wherein:

$X^a$ and $X^{a'}$ are independently selected from a bond or $C_{1-6}$ alkylene;

$Z^{X'}$ and $Z^X$ are each independently selected from hydrogen, $C_{1-8}$ alkyl, halogen, cyano, nitro,

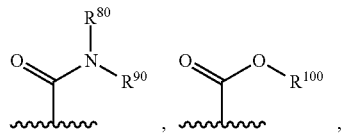

or —$(CH_2)_m$—$OCH_3$;

each $R^{80}$, $R^{90}$ and $R^{100}$ is independently selected from hydrogen, $C_{1-8}$ alkyl, $C_{2-6}$ alkenyl, and $C_{1-6}$ alkoxy; and m is an integer of 0 to 12.

In some embodiments, $Z^{X'}$ and $Z^X$ are each independently selected from hydrogen,

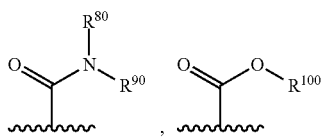

and —$(CH_2)_m$—$OCH_3$;

each $R^{80}$, $R^{90}$ and $R^{100}$ is independently selected from hydrogen, $C_{1-3}$ alkyl, and $C_{1-3}$ alkoxy;

m is an integer of 1 to 6.

In some preferred embodiments, the active agent is

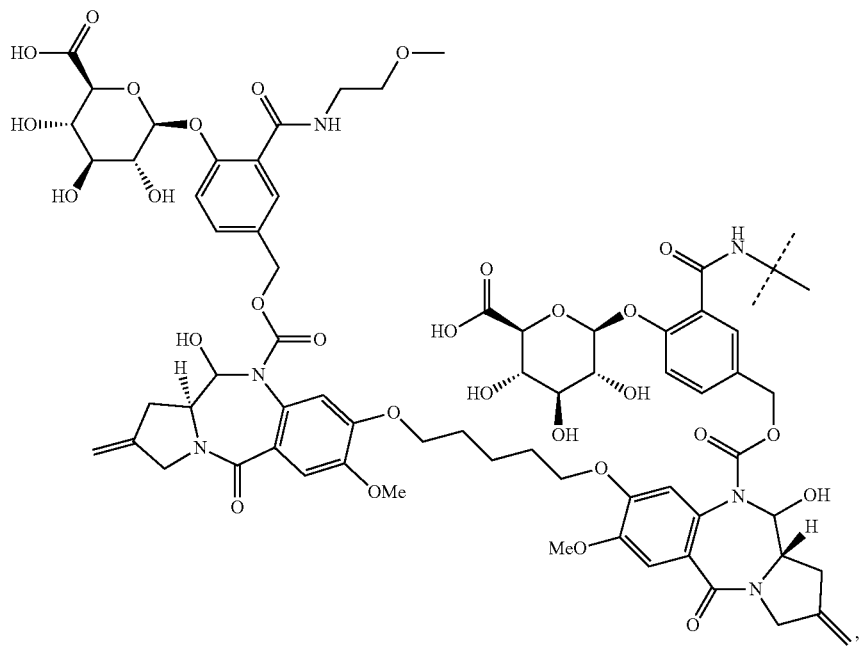

-continued
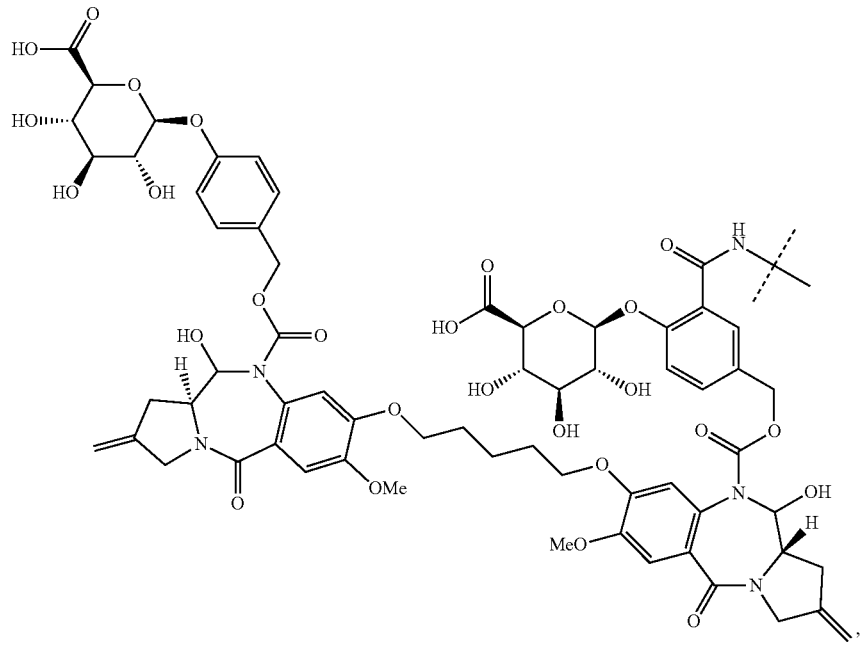
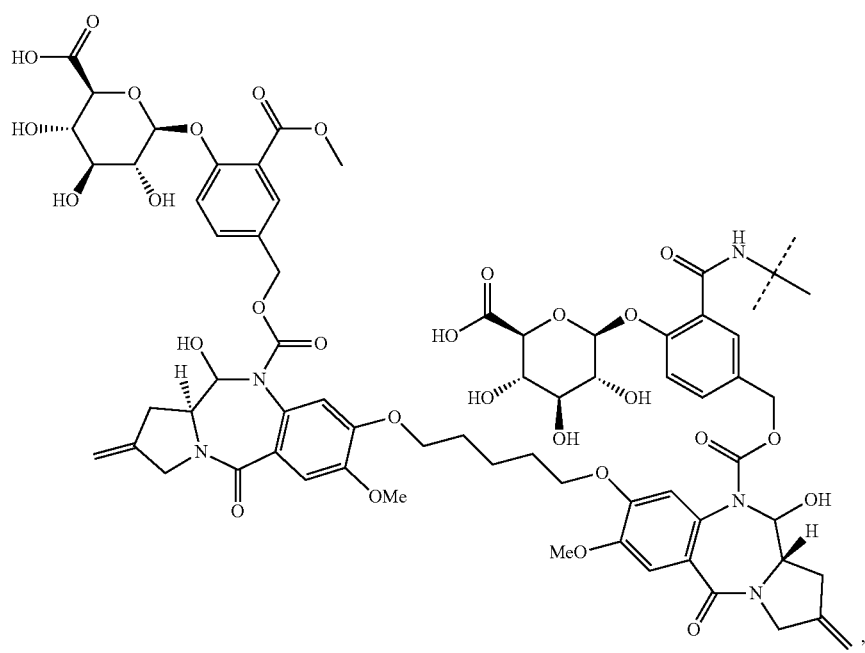

-continued
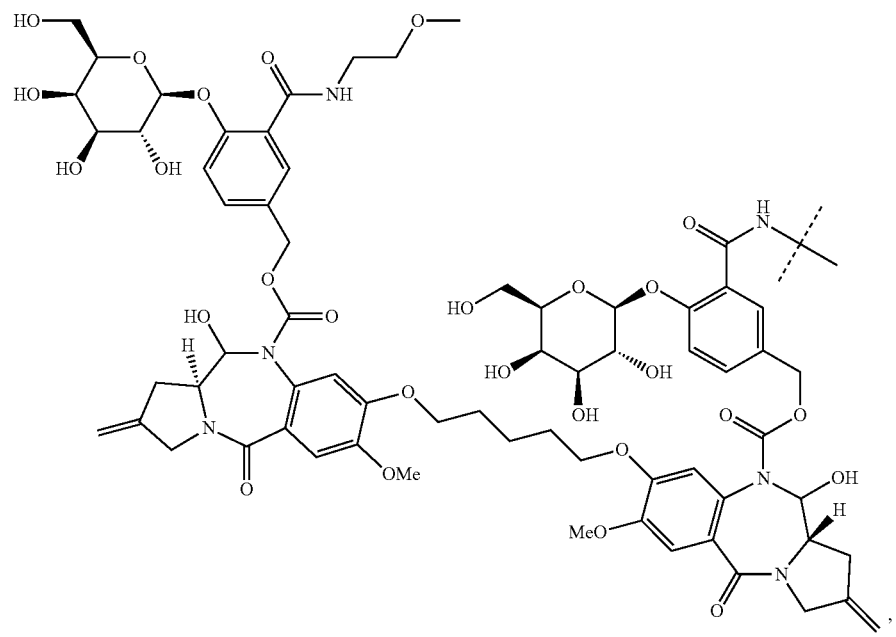
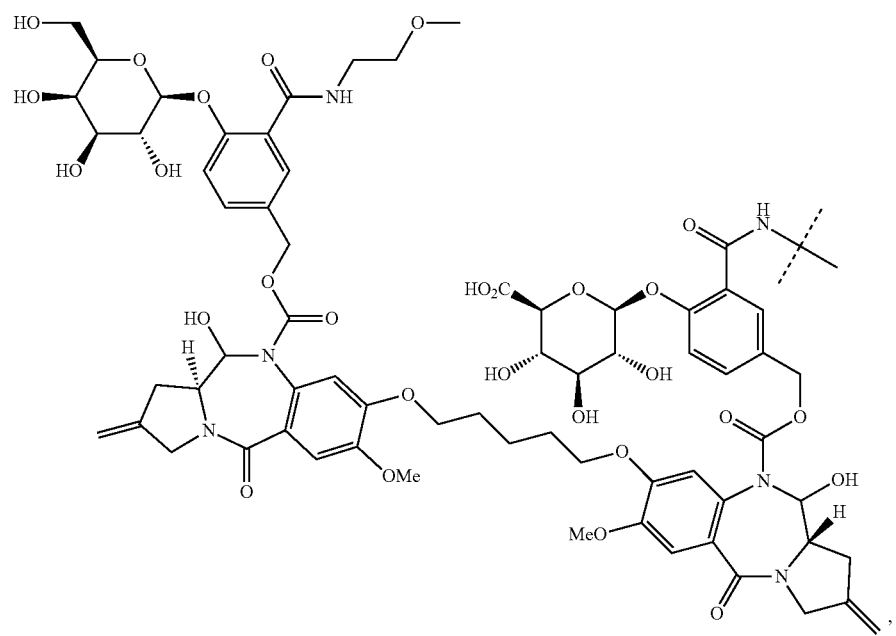

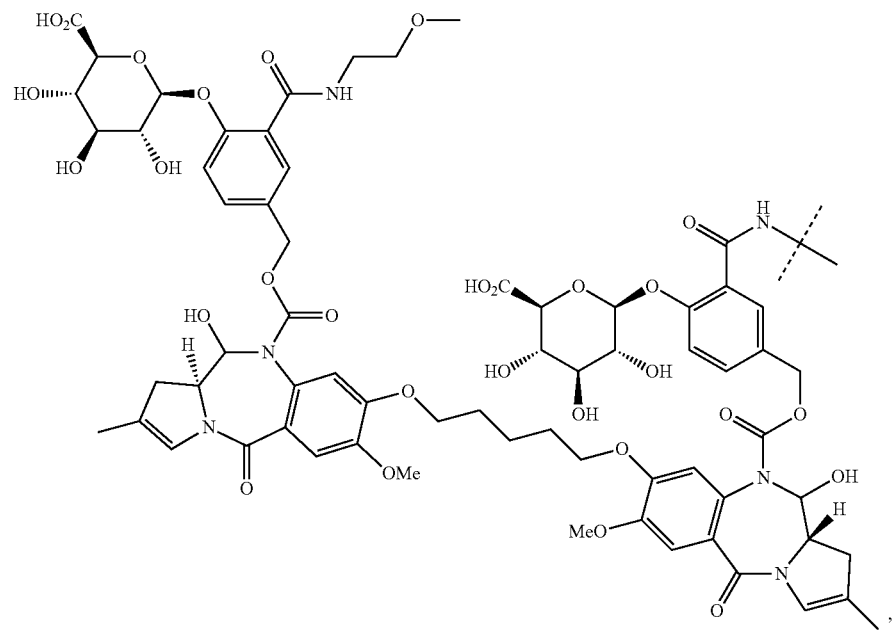
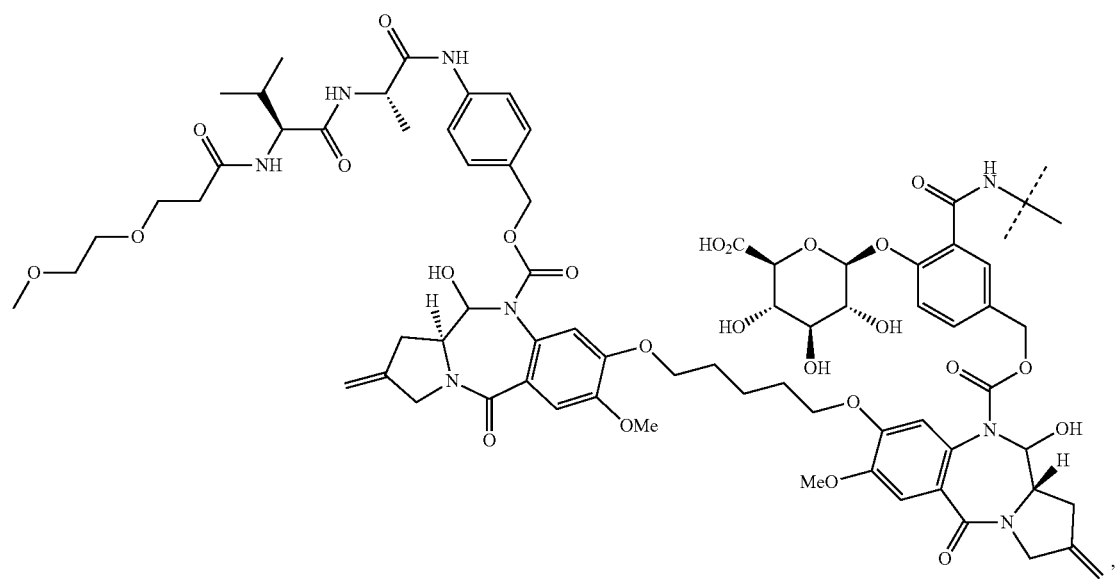

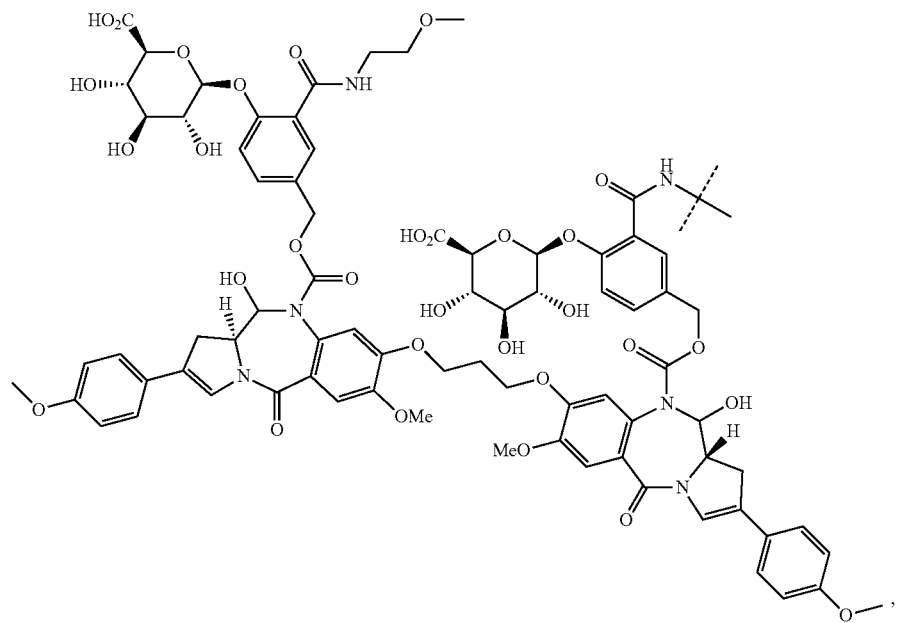
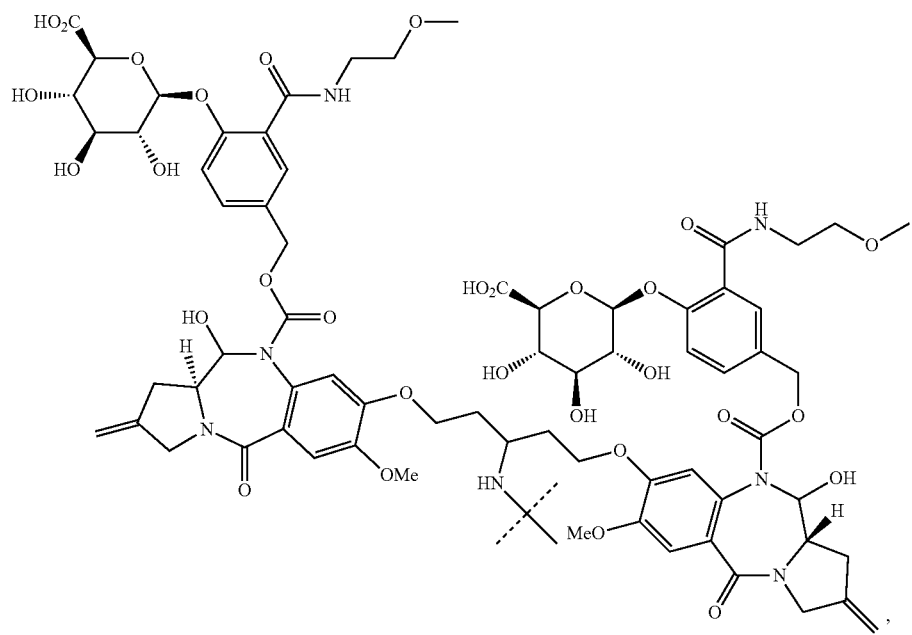

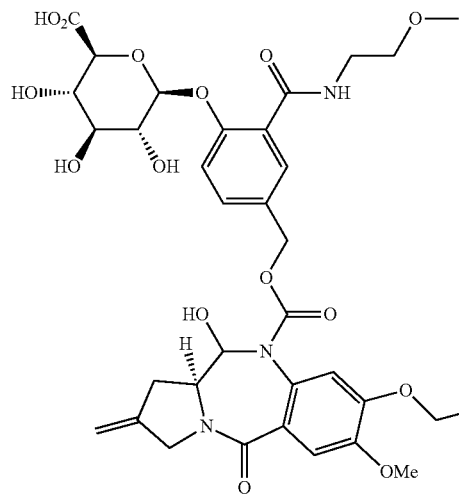
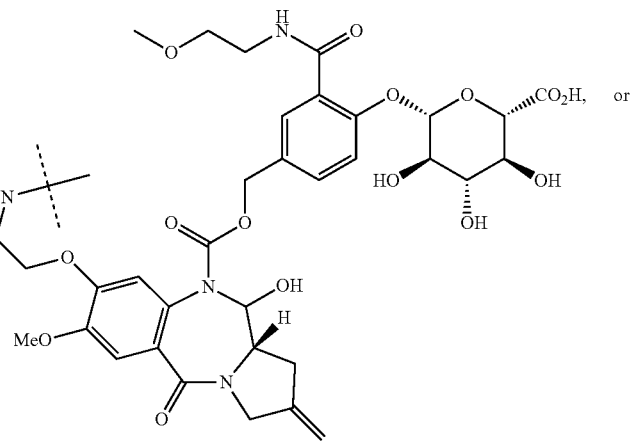
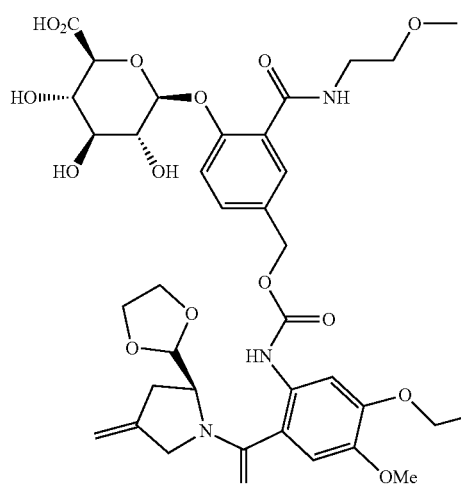
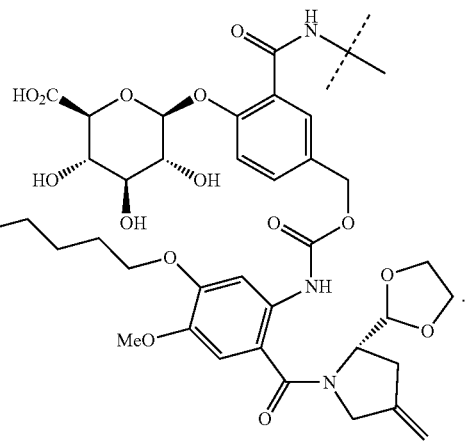

X may be connected to Ab via a coupling group, which may be formed by reacting two individual coupling groups. For example, the coupling group may be formed by the reaction of an amine or a hydroxylamine with an electrophile to form, e.g., an amide or an N—C bond. In some embodiments, X comprises a coupling group and is connected to Ab via the coupling group (e.g., an amine, an amide, a hydroxylamine, a triazole, an alkyne, a disulfide, or a thioether). The triazole may be formed by reacting an azide with an alkyne. The succinimide may be formed by reacting a thiol with a maleimide. The disulfide may be formed by reacting a thiol with a maleimide.

In some embodiments, at least one X comprises a moiety formed from one of the following structural formulas. It is understood that the coupling groups in the structures below are drawn as structurally complete formulas, but the coupling groups therein are coupled to Ab through suitable reactions. For example, —NH₂ groups drawn below are understood to encompass —N(H)— groups when coupled to an Ab moiety. Likewise, azide or ethynyl groups are understood to encompass triazoles:

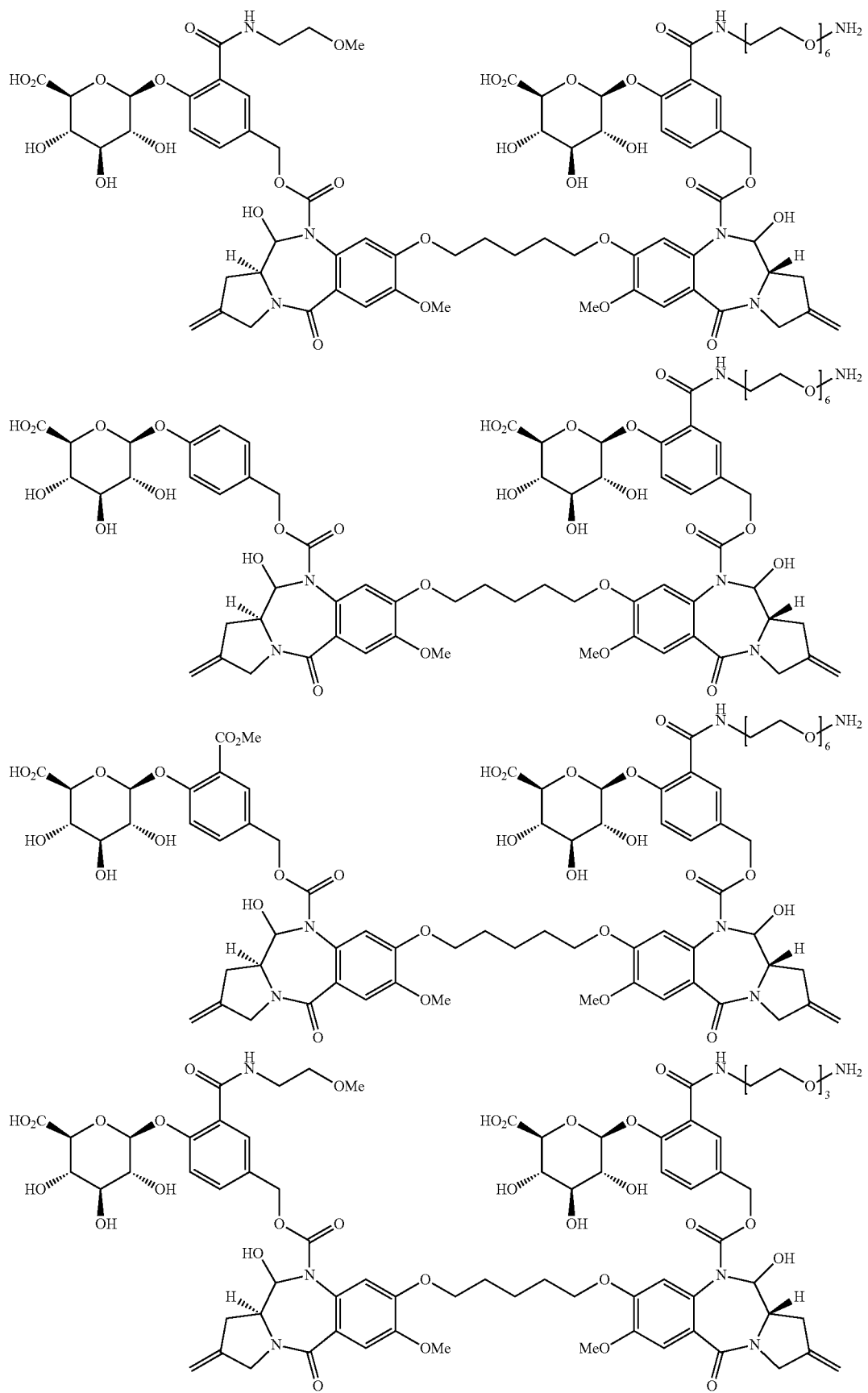

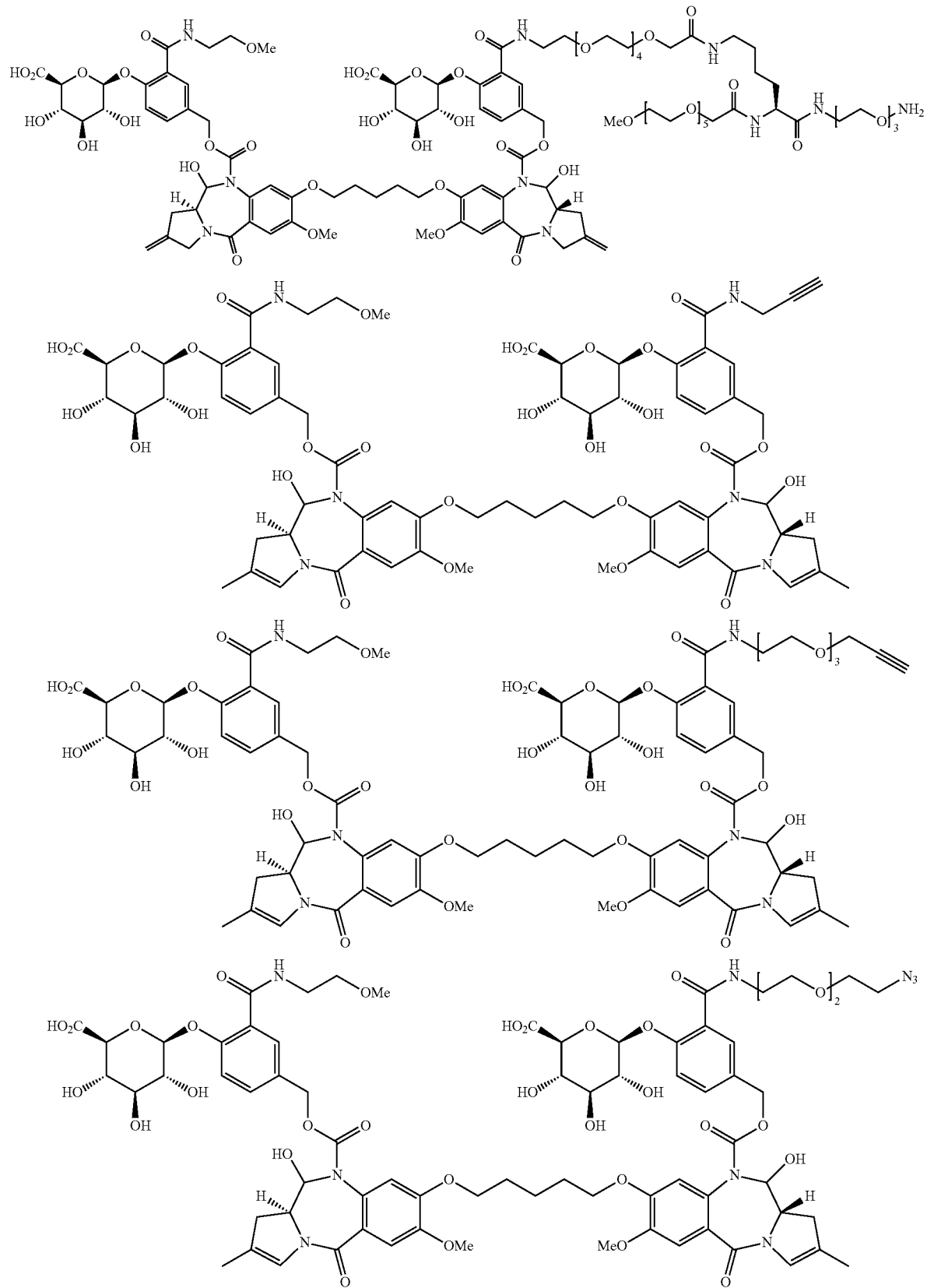

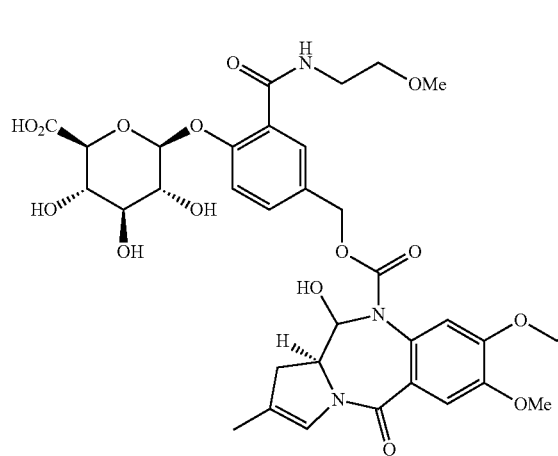
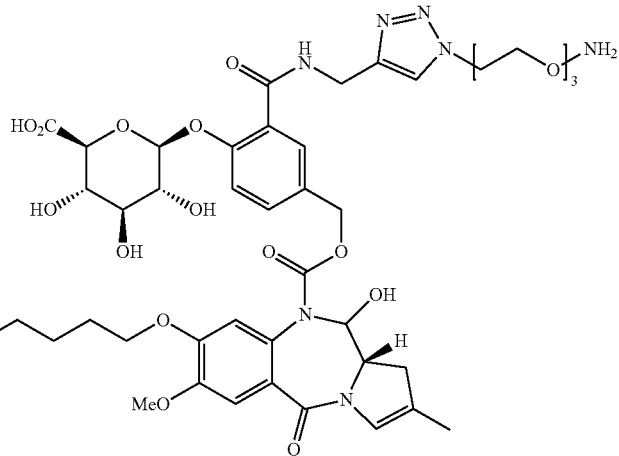
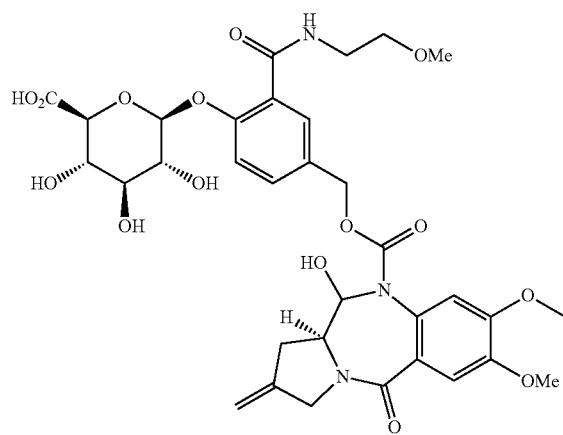
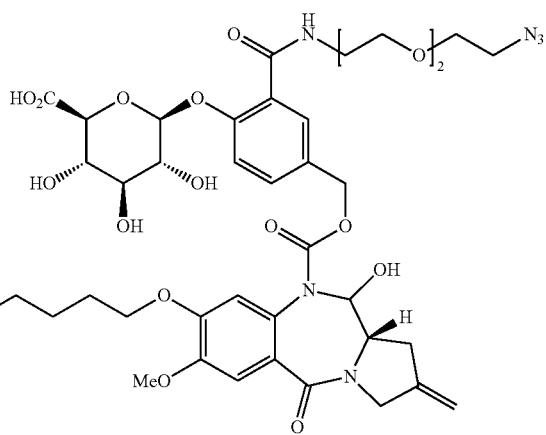
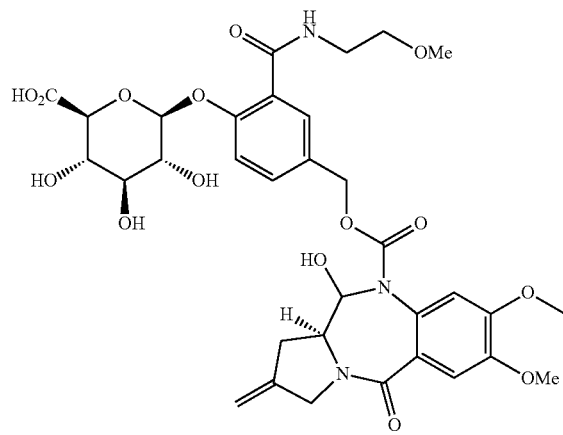
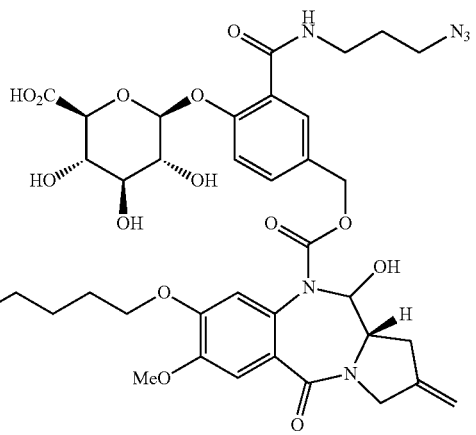

-continued
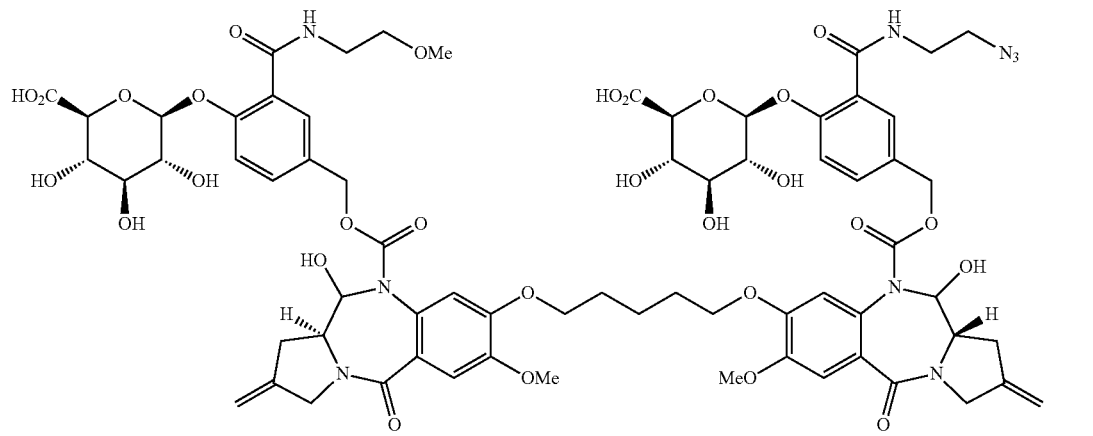
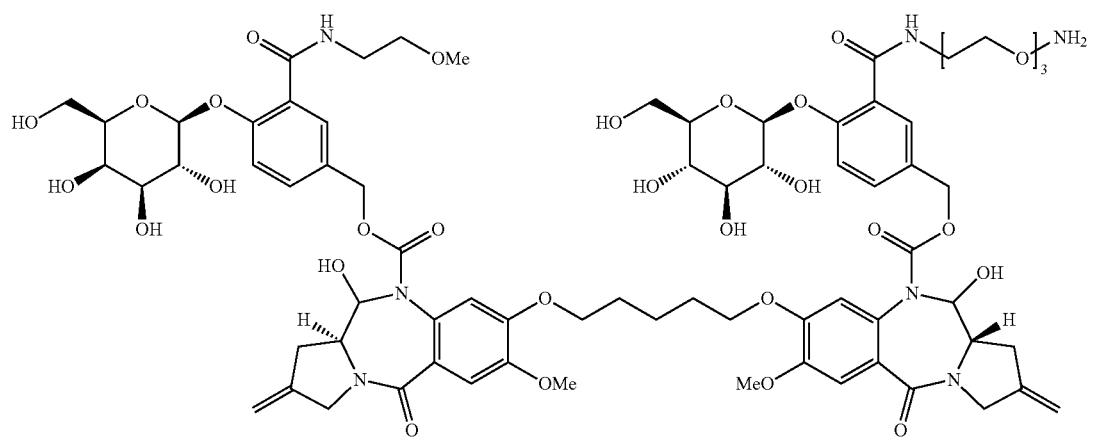
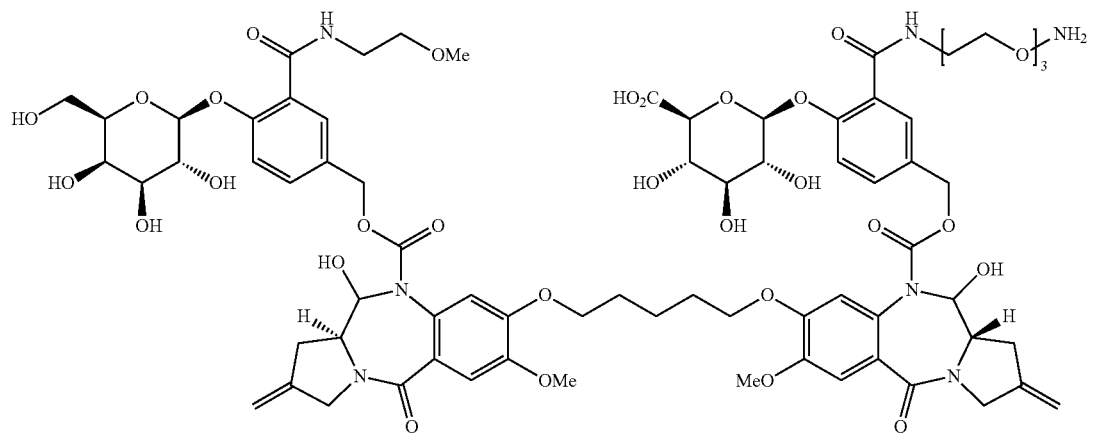

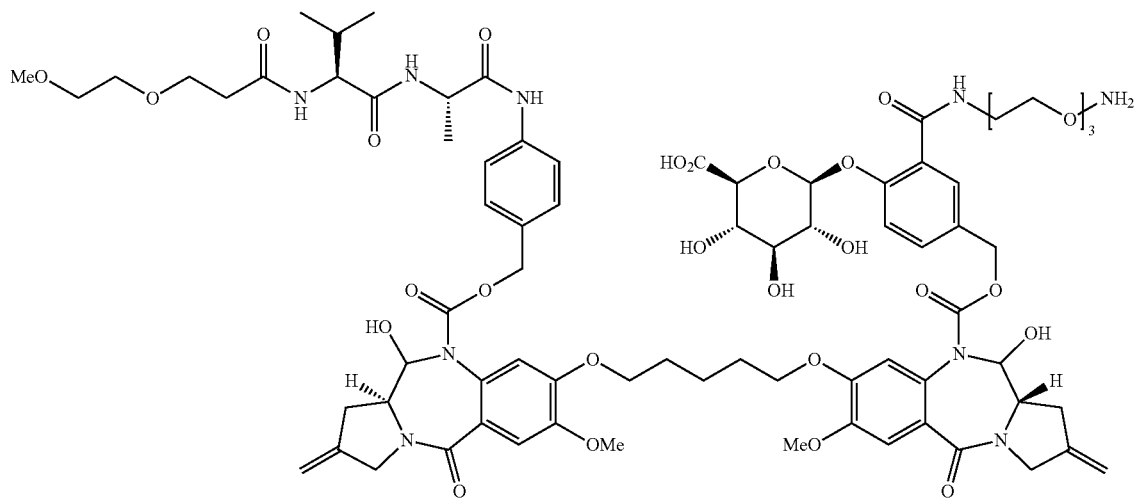
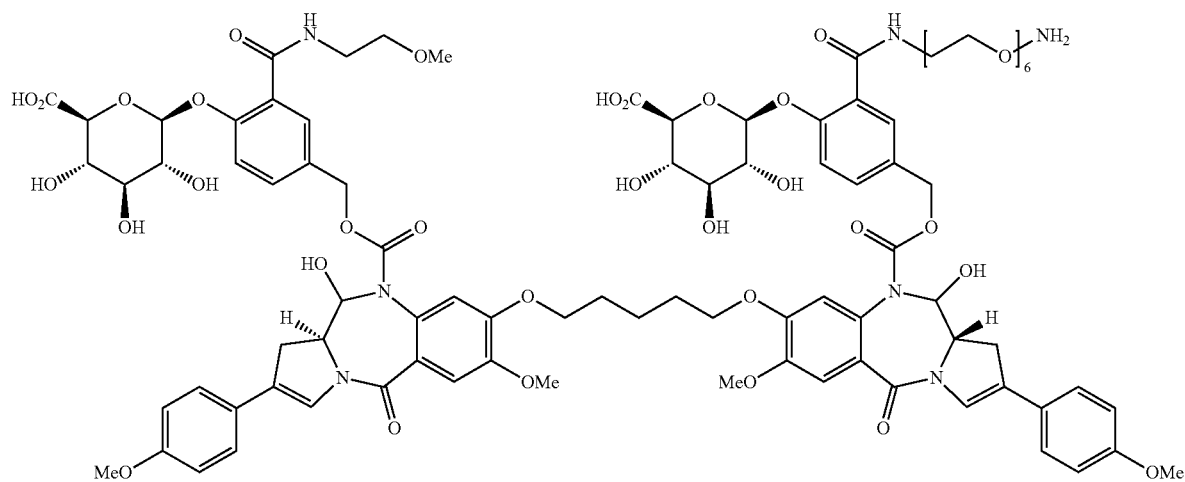
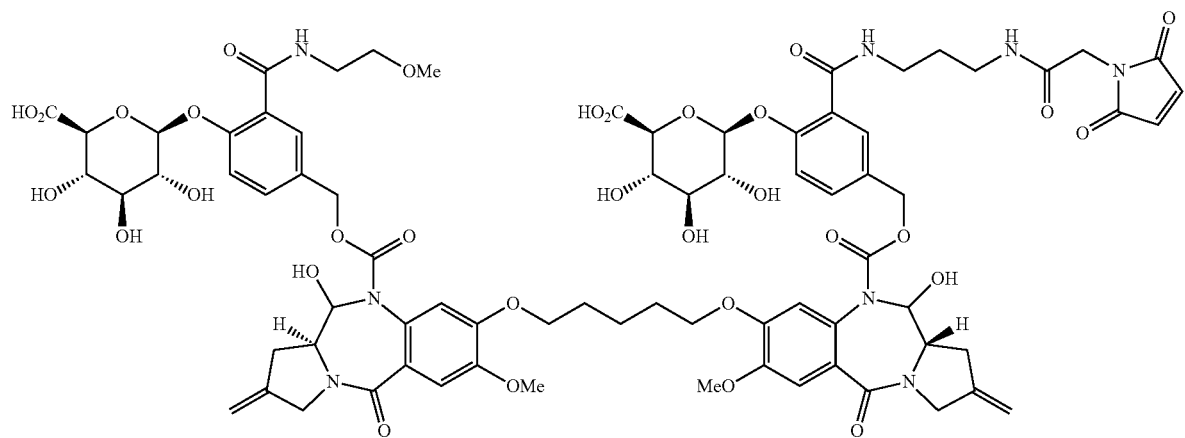

-continued
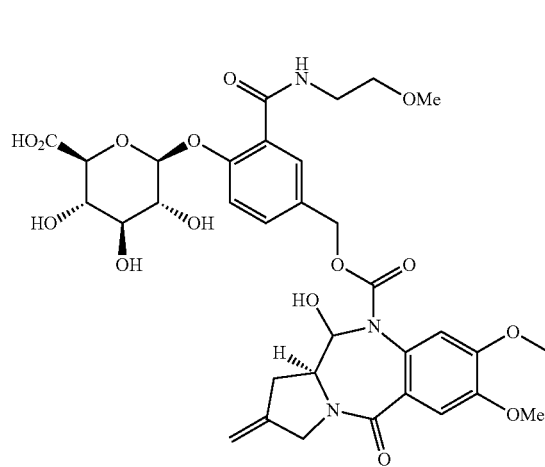
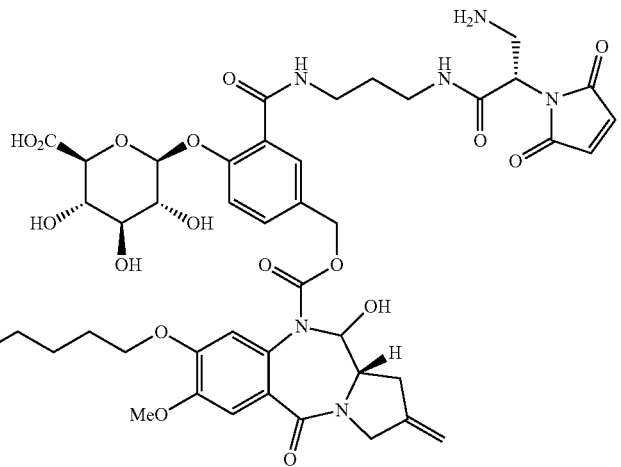
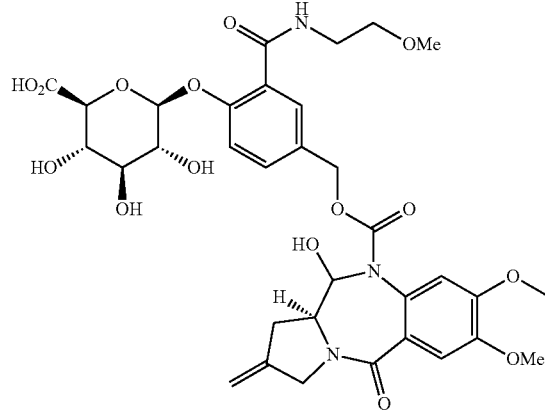
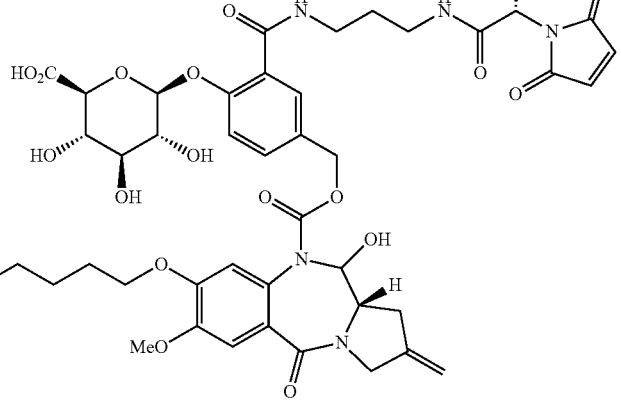
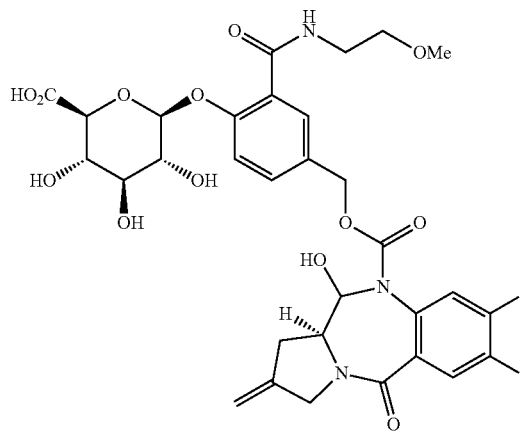
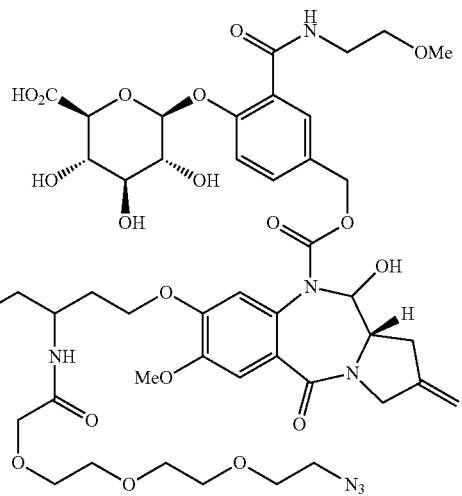

51 52
-continued
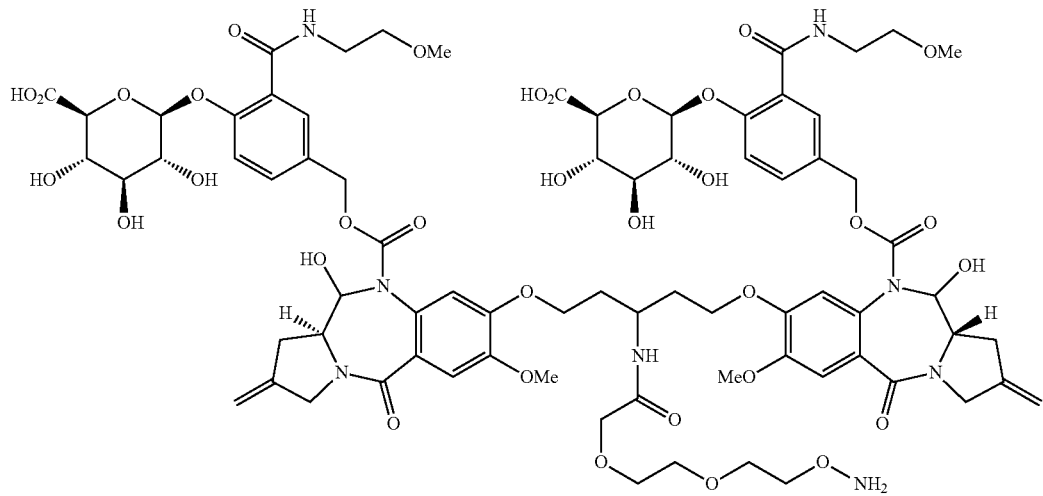
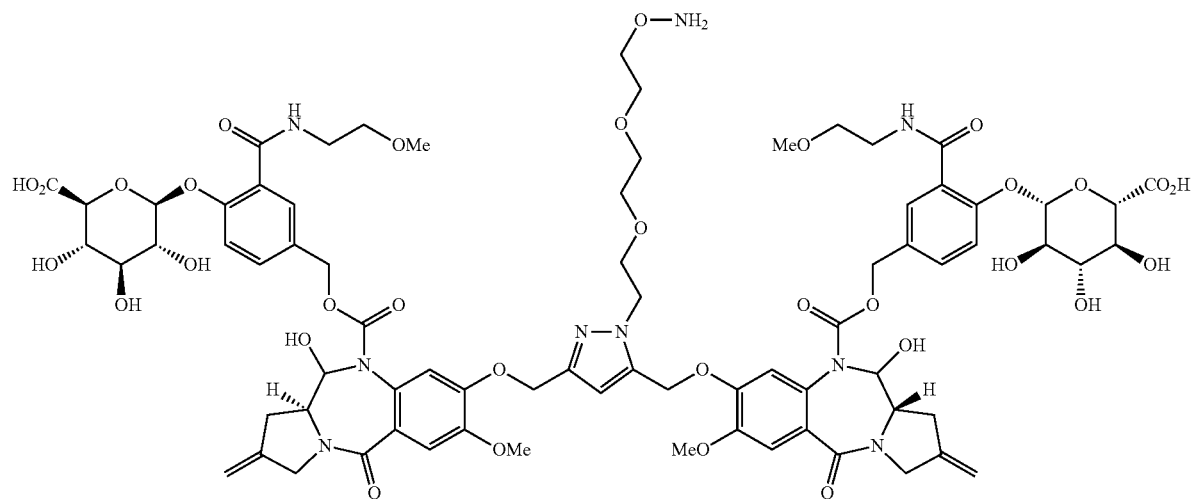
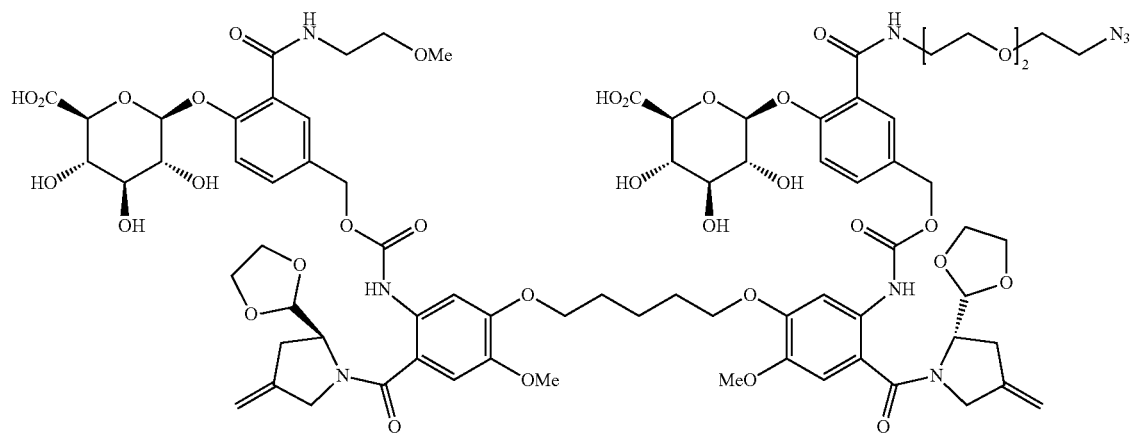

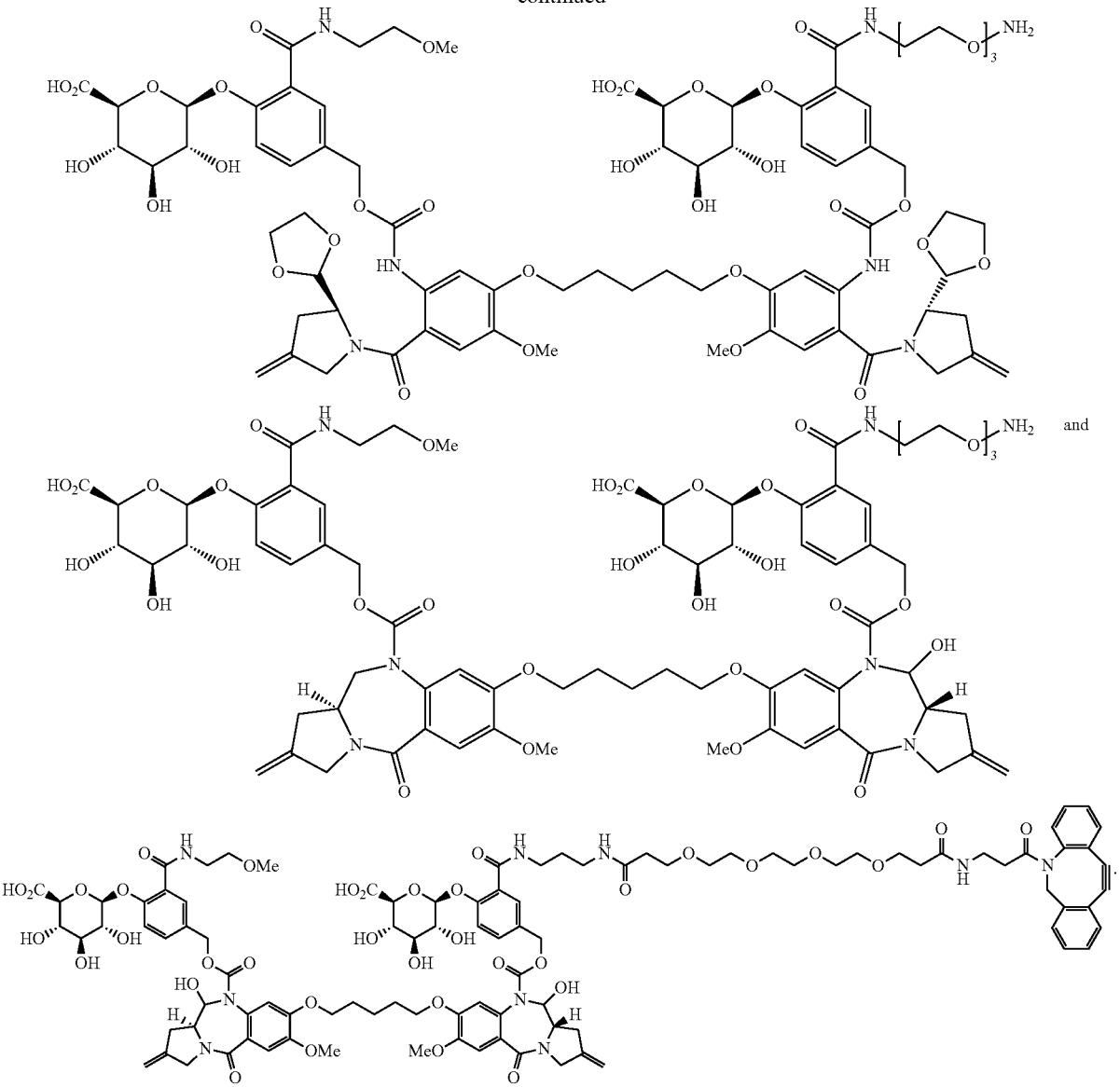

In another aspect, the present disclosure provides pharmaceutical compositions comprising an antibody drug conjugate as described herein, optionally further comprising a therapeutically effective amount of a chemotherapeutic agent.

In yet another aspect, the present disclosure provides methods of treating cancer, comprising administering an antibody-drug conjugate of the disclosure or a pharmaceutical composition thereof. In some such embodiments, the cancer is selected from leukemia, lymphoma, breast cancer, colon cancer, ovarian cancer, bladder cancer, prostate cancer, glioma, lung cancer, bronchial cancer, colorectal cancer, pancreatic cancer, esophageal cancer, liver cancer, urinary bladder cancer, kidney cancer, renal pelvis cancer, oral cavity cancer, pharynx cancer, uterine corpus cancer, or melanoma.

In yet another aspect, the present disclosure provides methods of treating autoimmune diseases or an inflammatory diseases, comprising administering an antibody drug conjugate of the disclosure or a pharmaceutical composition thereof. In some embodiments, the autoimmune diseases or the inflammatory disease is selected from B-cell mediated autoimmune diseases or inflammatory diseases, for example, systemic lupus erythematosus (SLE), rheumatoid arthritis (RA), idiopathic thrombocytopenic purpura (ITP), Waldenstrom's hypergammaglobulinaemia, Sjogren's syndrome, multiple sclerosis (MS), or lupus nephritis.

Anti-CD19 Antibodies

Exemplary anti-CD19 antibodies include the antibodies referred to herein as 5F5, 7F11, 9G8, F6, 7F1, and 10D8, or any fragments, variants, multimeric versions, or bispecifics thereof. Similarly, the anti-CD19 antibody may be an antibody or any fragment, variant, multimeric version, or bispecific variant thereof that binds to the same epitope as 5F5, 7F11, 9G8, F6, 7F1, and 10D8. These antibodies or any fragments, variants, multimeric versions, or bispecifics thereof are respectively referred to herein as "huCD19" antibodies. The huCD19 antibodies of the disclosure include fully human monoclonal antibodies, as well as humanized monoclonal antibodies and chimeric antibodies, or any fragments, variants, multimeric versions, or bispecifics thereof. These antibodies show specificity for human CD19, and they have been shown to modulate, e.g., block, inhibit, reduce, antagonize, neutralize or otherwise interfere with at least one biological function or activity of CD19.

Biological function or activities of CD19 include, by way of non-limiting example, functioning as a B cell co-receptor with CD21 and/or CD81, binding, when in the activated, phosphorylated state, to one or more Src-family kinases; and/or recruitment of PI-3 kinase. The antibodies are considered to completely modulate, block, inhibit, reduce, antagonize, neutralize or otherwise interfere with at least one functional activity of CD19 when the level of functional activity of CD19 in the presence of the antibody is decreased by at least 95%, e.g., by 96%, 97%, 98%, 99% or 100% as compared to the level of functional activity of CD19 in the absence of binding with an antibody described herein. The antibodies are considered to partially modulate, block, inhibit, reduce, antagonize, neutralize or otherwise interfere with at least one functional activity of CD19 when the level of functional activity of CD19 in the presence of the antibody is decreased by less than 95%, e.g., 10%, 20%, 25%, 30%, 40%, 50%, 60%, 75%, 80%, 85% or 90% as compared to the level of functional activity of CD19 in the absence of binding with an antibody described herein.

Each of the huCD19 monoclonal antibodies or any fragment, variant, multimeric version, or bispecific variant thereof described herein includes a heavy chain variable region (VH) and a light chain variable region (VL), as shown in the amino acid and corresponding nucleic acid sequences listed below. The CDR sequences, according to IMGT, are boxed in each of the VH and VL sequences below.

The 5F5 antibody includes a heavy chain variable region (VH) (SEQ ID NO: 2) encoded by the nucleic acid sequence shown in SEQ ID NO: 1, and a light chain variable region (VL) (SEQ ID NO: 4) encoded by the nucleic acid sequence shown in SEQ ID NO: 3:

```
>5F5_VH
                                             (SEQ ID NO: 2)
EVQLVQSGAEVKKPGESLKISCKGSGYSFTSYWIGWVRQMPGKGLEWMGI

IYPGDSDTRYSPSFQGQVTISADKSISTAYLQWSSLKASDTAMYYCARGI

SGIYNLHGFDIWGQGTLVTVSS

>5F5_VH
                                             (SEQ ID NO: 1)
GAGGTGCAGCTGGTGCAGTCTGGAGCAGAGGTGAAAAAGCCCGGGGAGTC

TCTGAAGATCTCCTGTAAGGGTTCTGGATACAGCTTTACCAGCTACTGGA

TCGGCTGGGTGCGCCAGATGCCCGGGAAAGGCCTGGAGTGGATGGGGATC

ATCTATCCTGGTGACTCTGATACCAGATACAGCCCGTCCTTCCAAGGCCA

GGTCACCATCTCAGCCGACAAGTCCATCAGCACCGCCTACCTTCAGTGGA

GCAGCCTGAAGGCCTCGGACACCGCCATGTATTACTGTGCGAGAGGTATA

AGTGGGATCTACAATTTACACGGTTTTGATATCTGGGGCCAGGGAACCCT

GGTCACAGTCTCGAGC
```

```
>5F5_VL
                                             (SEQ ID NO: 4)
DIQMTQSPSSLSASVGDRVTITCRASQSISSYLNWYQQKPGKAPKLLIYA

ASSLQSGVPSRFSGSGSGTDFTLTISSLQPEDFATYYCQQASLDSPLTFG

QGTKVEIK

>5F5_VL
                                             (SEQ ID NO: 3)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGGCGAGCTTGGACAGCCCGTTGACCTTCGGC

CAAGGGACCAAGGTGGAAATCAAA
```

The 7F11 antibody includes a heavy chain variable region (VH) (SEQ ID NO: 6) encoded by the nucleic acid sequence shown in SEQ ID NO: 5, and a light chain variable region (VL) (SEQ ID NO: 8) encoded by the nucleic acid sequence shown in SEQ ID NO: 7:

```
>7F11_VH
                                             (SEQ ID NO: 6)
EVQLVQSGAEVKKPGESLKISCKGSGYSFTSYWIGWVRQMPGKGLEWMGI

IYPGDSDTRYSPSFQGQVTISADKSISTAYLQWSSLKASDTAMYYCARGV

SGIYNLHGFDIWGQGTLVTVSS

>7F11_VH
                                             (SEQ ID NO: 5)
GAGGTGCAGCTGGTGCAGTCTGGAGCAGAGGTGAAAAAGCCCGGGGAGTC

TCTGAAGATCTCCTGTAAGGGTTCTGGATACAGCTTTACCAGCTACTGGA

TCGGCTGGGTGCGCCAGATGCCCGGGAAAGGCCTGGAGTGGATGGGGATC

ATCTATCCTGGTGACTCTGATACCAGATACAGCCCGTCCTTCCAAGGCCA

GGTCACCATCTCAGCCGACAAGTCCATCAGCACCGCCTACCTTCAGTGGA

GCAGCCTGAAGGCCTCGGACACCGCCATGTATTACTGTGCGAGAGGTGTA

AGTGGGATCTACAATTTACACGGTTTTGATATCTGGGGCCAGGGAACCCT

GGTCACAGTCTCGAGC

>7F11_VL
                                             (SEQ ID NO: 8)
DIQMTQSPSSLSASVGDRVTITCRASQSISSYLNWYQQKPGKAPKLLIY

AASSLQSGVPSRFSGSGSGTDFTLTISSLQPEDFATYYCQQGMWDNPFTF

GQGTKVEIK

>7F11_VL
                                             (SEQ ID NO: 7)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG
```

The 9G8 antibody includes a heavy chain variable region (VH) (SEQ ID NO: 6) encoded by the nucleic acid sequence shown in SEQ ID NO: 39, and a light chain variable region (VL) (SEQ ID NO: 10) encoded by the nucleic acid sequence shown in SEQ ID NO: 9:

```
>9G8_VH
                                            (SEQ ID NO: 6)
EVQLVQSGAEVKKPGESLKISCKGSGYSFTSYWIGWVRQMPGKGLEWMGI

IYPGDSDTRYSPSFQGQVTISADKSISTAYLQWSSLKASDTAMYYCARGV

SGIYNLHGFDIWGQGTLVTVSS

>9G8_VH
                                           (SEQ ID NO: 39)
GAGGTGCAGCTGGTGCAGTCTGGAGCAGAGGTGAAAAAGCCCGGGGAGTC

TCTGAAGATCTCCTGTAAGGGTTCTGGATACAGCTTTACCAGCTACTGGA

TCGGCTGGGTGCGCCAGATGCCCGGGAAAGGCCTGGAGTGGATGGGGATC

ATCTATCCTGGTGACTCTGATACCAGATACAGCCCGTCCTTCCAAGGCCA

GGTCACCATCTCAGCCGACAAGTCCATCAGCACCGCCTACCTTCAGTGGA

GCAGCCTGAAGGCCTCGGACACCGCCATGTATTACTGTGCGAGAGGTGTA

AGTGGGATCTACAATTTACACGGTTTCGATATCTGGGGCCAGGGAACCCT

GGTCACAGTCTCGAGC

>9G8_VL
                                           (SEQ ID NO: 10)
DIQMTQSPSSLSASVGDRVTITCRASQSISSYLNWYQQKPGKAPKLLIYA

ASSLQSGVPSRFSGSGSGTDFTLTISSLQPEDFATYYCQQGRFGSPFTFG

QGTKVEIK

>9G8_VL
                                            (SEQ ID NO: 9)
GACATCCAGATGACCCAGTCTCCATCCTCCCTGTCTGCATCTGTAGGAGA

CAGAGTCACCATCACTTGCCGGGCAAGTCAGAGCATTAGCAGCTATTTAA

ATTGGTATCAGCAGAAACCAGGGAAAGCCCCTAAGCTCCTGATCTATGCT

GCATCCAGTTTGCAAAGTGGGGTCCCATCAAGGTTCAGTGGCAGTGGATC

TGGGACAGATTTCACTCTCACCATCAGCAGTCTGCAACCTGAAGATTTTG

CAACTTACTACTGTCAGCAGGGCAGGTTCGGGTCCCCGTTCACCTTCGGC

CAAGGGACCAAGGTGGAAATCAAA
```

The F6 antibody includes a heavy chain variable region (VH) (SEQ ID NO: 12) encoded by the nucleic acid sequence shown in SEQ ID NO: 11, and a light chain variable region (VL) (SEQ ID NO: 14) encoded by the nucleic acid sequence shown in SEQ ID NO: 13:

```
>F6_VH
                                           (SEQ ID NO: 12)
EVQLVQSGAEVKKPGESLKISCKGSGYSFTSYWIGWVRQMPGKGLEWMGI

IYPGDSDTRYSPSFQGQVTISADKSISTAYLQWSSLKASDTAMYYCARVW

YYDFWSGADAFDIWGQGTLVTVSS

>F6_VH
                                           (SEQ ID NO: 11)
GAGGTGCAGCTGGTGCAGTCTGGAGCAGAGGTGAAAAAGCCCGGGGAGTC

TCTGAAGATCTCCTGTAAGGGTTCTGGATACAGCTTTACCAGCTACTGGA

TCGGCTGGGTGCGCCAGATGCCCGGGAAAGGCCTGGAGTGGATGGGGATC

ATCTATCCTGGTGACTCTGATACCAGATACAGCCCGTCCTTCCAAGGCCA

GGTCACCATCTCAGCCGACAAGTCCATCAGCACCGCCTACCTTCAGTGGA

GCAGCCTGAAGGCCTCGGACACCGCCATGTATTACTGTGCGAGAGTCTGG

TATTACGATTTTTGGAGTGGGGCCGATGCTTTTGATATCTGGGGCCAGGG

AACCCTGGTCACAGTCTCGAGC

>F6_VL
                                           (SEQ ID NO: 14)
EIVMTQSPATLSVSPGERATLSCRASQSVSSNLAWYQQKPGQAPRLLIYG

ASTRATGIPARFSGSGSGTEFTLTISSLQSEDFAVYYCQQGSLEAPQTFG

QGTKVEIK

>F6_VL
                                           (SEQ ID NO: 13)
GAAATAGTGATGACGCAGTCTCCAGCCACCCTGTCTGTGTCTCCAGGGGA

AAGAGCCACCCTCTCCTGCAGGGCCAGTCAGAGTGTTAGCAGCAACTTAG

CCTGGTACCAGCAGAAACCTGGCCAGGCTCCCAGGCTCCTCATCTATGGT

GCATCCACCAGGGCCACTGGTATCCCAGCCAGGTTCAGTGGCAGTGGGTC

TGGGACAGAGTTCACTCTCACCATCAGCAGCCTGCAGTCTGAAGATTTTG

CAGTTTATTACTGTCAGCAGGGCAGCTTGGAGGCGCCGCAGACCTTCGGC

CAAGGGACCAAGGTGGAAATCAAA
```

The 7F1 antibody includes a heavy chain variable region (VH) (SEQ ID NO: 16) encoded by the nucleic acid sequence shown in SEQ ID NO: 15, and a light chain variable region (VL) (SEQ ID NO: 18) encoded by the nucleic acid sequence shown in SEQ ID NO: 17:

```
>7F1_VH
                                           (SEQ ID NO: 16)
EVQLVQSGAEVKKPGESLKISCKGSGYSFTSYWIGWVRQMPGKGLEWMGI

IYPGDSDTRYSPSFQGQVTISADKSISTAYLQWSSLKASDTAMYYCARGD

YWTGFAYWGQGTLVTVSS

>7F1_VH
                                           (SEQ ID NO: 15)
GAGGTGCAGCTGGTGCAGTCTGGAGCAGAGGTGAAAAAGCCCGGGGAGTC

TCTGAAGATCTCCTGTAAGGGTTCTGGATACAGCTTTACCAGCTACTGGA

TCGGCTGGGTGCGCCAGATGCCCGGGAAAGGCCTGGAGTGGATGGGGATC

ATCTATCCTGGTGACTCTGATACCAGATACAGCCCGTCCTTCCAAGGCCA

GGTCACCATCTCAGCCGACAAGTCCATCAGCACCGCCTACCTGCAGTGGA

GCAGCCTGAAGGCCTCGGACACCGCCATGTATTACTGTGCGAGAGGTGAT

TATTGGACTGGTTTTGCTTATTGGGGCCAGGGAACCCTGGTCACAGTCTC

GAGC
```

```
>7F1_VL
                                          (SEQ ID NO: 18)
QSVLTQPPSVSAAPGQKVTISCSGSSSNIGNNYVSWYQQLPGTAPKLLIY

DNNKRPSGIPDRFSGSKSGTSATLGITGLQTGDEADYYCGTWDLGWNSVF

GGGTKLTVL

>7F1_VL
                                          (SEQ ID NO: 17)
CAGTCTGTGTTGACGCAGCCGCCCTCAGTGTCTGCGGCCCCAGGACAGAA

GGTCACCATCTCCTGCTCTGGAAGCAGCTCCAACATTGGGAATAATTATG

TATCCTGGTACCAGCAGCTCCCAGGAACAGCCCCCAAACTCCTCATTTAT

GACAATAATAAGCGACCCTCAGGGATTCCTGACCGATTCTCTGGCTCCAA

GTCTGGCACGTCAGCCACCCTGGGCATCACCGGACTCCAGACTGGGGACG

AGGCCGATTATTACTGCGGAACATGGGATCTGGGCTGGAACTCGGTGTTC

GGCGGAGGGACCAAGCTGACCGTCCTA
```

The 10D8 antibody includes a heavy chain variable region (VH) (SEQ ID NO: 20) encoded by the nucleic acid sequence shown in SEQ ID NO: 19, and a light chain variable region (VL) (SEQ ID NO: 22) encoded by the nucleic acid sequence shown in SEQ ID NO: 21:

```
>10D8_VH
                                          (SEQ ID NO: 20)
QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCARDR

GYDYVWGSYRYGAFDIWGQGTLVTVSS

>10D8_VH
                                          (SEQ ID NO: 19)
CAGGTGCAGCTGGTGCAGTCTGGGGCTGAGGTGAAGAAGCCTGGGTCCTC

GGTGAAGGTCTCCTGCAAGGCTTCTGGAGGCACCTTCAGCAGCTATGCTA

TCAGCTGGGTGCGACAGGCCCCTGGACAAGGGCTTGAGTGGATGGGAGGG

ATCATCCCTATCTTTGGTACAGCAAACTACGCACAGAAGTTCCAGGGCAG

AGTCACGATTACCGCGGACGAATCCACGAGCACAGCCTACATGGAGCTGA

GCAGCCTGAGATCTGAGGACACGGCCGTGTATTACTGTGCGAGAGATCGG

GGGTATGATTACGTTTGGGGGAGTTATCGTTATGGTGCCTTTGATATCTG

GGGCCAGGGAACCCTGGTCACAGTCTCGAGC

>10D8_VL
                                          (SEQ ID NO: 22)
QSALTQPASVSGSPGQSITISCTGTSSDVGGYNYVSWYQQHPGKAPKLMI

YEVSNRPSGVSNRFSGSKSGNTASLTISGLQAEDEADYYCSSYDVWVPHM

VFGGGTKLTVL

>10D8_VL
                                          (SEQ ID NO: 21)
CAGTCTGCCCTGACTCAGCCTGCCTCCGTGTCTGGGTCTCCTGGACAGTC

GATCACCATCTCCTGCACTGGAACCAGCAGTGACGTTGGTGGTTATAACT

ATGTCTCCTGGTACCAACAGCACCCAGGCAAAGCCCCCAAACTCATGATT

TATGAGGTCAGTAATCGGCCCTCAGGGGTTTCTAATCGCTTCTCTGGCTC

CAAGTCTGGCAACACGGCCTCCCTGACCATCTCTGGGCTCCAGGCTGAGG

ACGAGGCTGATTATTACTGCAGCTCATATGATGTCTGGGTCCCGCACATG

GTGTTCGGCGGAGGGACCAAGCTGACCGTCCTA
```

In some embodiments, the anti-CD19 antibody sequences presented herein or antigen binding fragments thereof are used to produce a monovalent antibody. The monovalent antibodies of the disclosure include a common heavy chain sequence, one arm that specifically recognizes CD19, and a second arm referred to herein as a dummy arm. The dummy arm includes an amino acid sequence that does not bind or otherwise cross-react with a human protein. In some embodiments, the dummy arm includes an amino acid sequence that does not bind or otherwise cross-react with a human protein that is found in whole blood. In some embodiments, the dummy arm includes an amino acid sequence that does not bind or otherwise cross-react with a human protein that is found in solid tissue. Preferably, the monovalent antibodies are specific for at least human CD19. In some embodiments, the monovalent antibodies that recognize human CD19 are also cross-reactive for at least one other non-human CD19 protein, such as, by way of non-limiting example, non-human primate CD19, e.g., cynomolgus monkey CD19, and/or rodent CD19.

In some embodiments, the anti-CD19 antibody sequence or an antigen binding fragment thereof is used with a second antibody sequence or an antigen binding fragment thereof that binds a target other than CD19 to produce a bispecific antibody referred to herein as an "anti-CD19 bispecific antibody."

While antibody sequences below are provided herein as examples, it is to be understood that these sequences can be used to generate bispecific antibodies using any of a variety of art-recognized techniques. Examples of bispecific formats include but are not limited to fully human bispecific antibodies that include a common heavy chain, a kappa-type light chain, and a lambda-type light chain (PCT Publication No. WO 2012/023053), bispecific IgG based on Fab arm exchange (Gramer et al., 2013 MAbs. 5(6)); the CrossMab format (Klein C et al., 2012 MAbs 4(6)); multiple formats based on forced heterodimerization approaches such as SEED technology (Davis J H et al., 2010 Protein Eng Des Sel. 23(4):195-202), electrostatic steering (Gunasekaran K et al., J Biol Chem. 2010 285(25):19637-46.) or knob-into-hole (Ridgway J B et al., Protein Eng. 1996 9(7):617-21.) or other sets of mutations preventing homodimer formation (Von Kreudenstein T S et al., 2013 MAbs. 5(5):646-54.); fragment based bispecific formats such as tandem scFv (such asBiTEs) (Wolf E et al., 2005 Drug Discov. Today 10(18):1237-44.); bispecific tetravalent antibodies (Pörtner L M et al., 2012 Cancer Immunol Immunother. 61(10):1869-75.); dual affinity retargeting molecules (Moore P A et al., 2011 Blood. 117(17):4542-51), diabodies (Kontermann R E et al., Nat Biotechnol. 1997 15(7):629-31).

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, Mass. (2000).

Unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, or any fragments, variants, multimeric versions, or bispecifics thereof, including, e.g., polyclonal, monoclonal, chimeric, dAb (domain antibody), single chain, $F_ab$, $F_{ab'}$ and $F_{(ab')2}$ fragments, scFvs, and an $F_ab$ expression library. The antibody may be any of the five major classes of immunoglobulins: IgA, IgD, IgE, IgG, and IgM, or subclasses (isotypes) thereof (for example, IgG1, IgG2, IgG3, IgG4, IgA1, and IgA2), based on the identity of its heavy chain constant domains, referred to as alpha, delta, epsilon, gamma, and mu, respectively. The different classes of immunoglobulins have different and well-known subunit structures and three-dimensional configurations. The term "antibody" does not refer to molecules that do not share homology with an immunoglobulin sequence. For example, the term "antibody" as used herein does not include "repebodies".

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antibody fragment" refers to a portion of an intact antibody and refers to antigenic determining variable regions of an intact antibody. Examples of antibody fragments include Fab, Fab', F(ab')$_2$, Fd, and Fv fragments, linear antibodies, single chain antibodies, and multispecific antibodies formed from antibody fragments.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen-binding site capable of immunoreacting with a particular epitope of the antigen characterized by a unique binding affinity for it. The term "monoclonal antibody" refers to a homogeneous antibody population involved in the highly specific recognition and binding of a single antigenic determinant or epitope. This contrasts with polyclonal antibodies that typically include different antibodies directed against a variety of different antigenic determinants. The term "monoclonal antibody" includes antibody fragments (such as Fab, Fab', F(ab')$_2$, Fd, Fv), single chain (scFv) mutants, fusion proteins including an antibody portion, and any other modified immunoglobulin molecule including an antigen recognition site as well as both intact and full-length monoclonal antibodies, but are not limited thereto. Additionally, "monoclonal antibody" refers to such antibodies made in any number of methods, including but not limited to hybridoma, phage selection, recombinant expression, and transgenic animals.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

An antibody "specifically binds" to an epitope or antigenic molecule, which means that the antibody interacts or associates more frequently, more rapidly, with greater duration, with greater affinity, or with some combination of the foregoing to an epitope or antigenic molecule than alternative substances, including unrelated proteins. In specific embodiments, "specifically binds" means, for instance, that an antibody binds to a protein with a $K_D$ of about 0.1 mM or less, but more usually, less than about 1 µM. In specific embodiments, "specifically binds" means that an antibody binds to a protein at times with a $K_D$ of about 0.1 µM or less, and at other times, with a $K_D$ of about 0.01 µM or less. Because of the sequence identity between homologous proteins in different species, specific binding may include an antibody recognizing a particular protein in more than one species. It is understood that an antibody or binding residue that specifically binds to a first target may or may not specifically bind to a second target. As described above, "specific binding" does not necessarily require (although it may include) exclusive binding, that is, binding to a single target. Generally, but not necessarily, the term binding used herein means specific binding.

The term "humanized antibody" refers to forms of non-human (e.g., murine) antibodies that are specific immunoglobulin chains, chimeric immunoglobulins, or fragments thereof that contain minimal non-human (e.g., murine) sequences. In general, humanized antibodies are human immunoglobulins in which residues from complementary determining region (CDR) are replaced by residues from CDR of a non-human species (e.g., mouse, rat, rabbit, and hamster) having the desired specificity, affinity, and capability (see, e.g., Jones et al., Nature, 321:522-525 (1986); Riechmann et al., Nature, 332:323-327 (1988); Verhoeyen et al., Science, 239:1534-1536 (1988)). In some instances, Fv framework region (FR) residues of a human immunoglobulin are replaced with the corresponding residues in an antibody from a non-human species having a desired specificity, affinity, and/or binding capability. The humanized antibody may be further modified by the substitution of additional residues either in the Fv framework region and/or within the replaced non-human residues to refine and optimize antibody specificity, affinity, and/or binding capability. In general, a humanized antibody includes substantially all of at least one, and typically two or three, variable domains containing all or substantially all of the CDRs that correspond to the non-human immunoglobulin whereas all or substantially all of the framework regions (FRs) have those of a human immunoglobulin consensus sequence. The humanized antibody may also include at least a portion of an immunoglobulin constant region or domain (Fc), typically that of a human immunoglobulin. Examples of methods used to generate humanized antibodies are described in U.S. Pat. No. 5,225,539, hereby incorporated by reference.

The term "human antibody" as used herein refers to an antibody encoded by a human nucleotide sequence or an antibody having an amino acid sequence corresponding to an antibody produced by a human using any suitable technique. This definition of the human antibody includes intact full-length antibodies and/or fragments thereof.

The term "chimeric antibody" refers to an antibody wherein an amino acid sequence of an immunoglobulin molecule is derived from two or more species, one of which is preferably human. In general, variable regions of both light and heavy chains correspond to variable regions of antibodies derived from one species of mammals (e.g., mouse, rat, rabbit, etc) with the desired specificity, affinity, and capability, while constant regions are homologous to the sequences in antibodies derived from another species (usually human), e.g., to avoid eliciting an immune response in that species.

The antibodies, including fragments/derivatives thereof and monoclonal antibodies, may be obtained using any suitable technique (see, e.g., McCafferty et al., Nature 348:552-554 (1990); Clackson et al., Nature 352:624-628; Marks et al., J. Mol. Biol. 222:581-597 (1991); Marks et al., Bio/Technology 10:779-783 (1992); Waterhouse et al., Nucleic Acids Res. 21:2265-2266 (1993); Morimoto et al., J Biochemical & Biophysical Methods 24:107-117 (1992); Brennan et al., Science 229:81(1985); Carter et al., Bio/Technology 10:163-167 (1992); Kohler et al., Nature 256: 495 (1975); Kilpatrick et al., Hybridoma 16(4):381-389 (1997); Wring et al., J. Pharm. Biomed. Anal. 19(5):695-707 (1999); Bynum et al., Hybridoma 18(5):407-411 (1999); Jakobovits et al., Proc. Natl. Acad. Sci. USA, 90:2551 (1993); Jakobovits et al., Nature, 362:255-258 (1993); Bruggemann et al., Year Immuno. 7:33 (1993); Barbas et al., Proc. Nat. Acad. Sci. USA 91:3809-3813 (1994); Schier et al., Gene 169:147-155 (1995); Yelton et al., J. Immunol. 155:1994-2004 (1995); Jackson et. al., J. Immunol. 154(7): 3310-9 (1995); Hawkins et al., J. Mol. Biol. 226:889-896 (1992), U.S. Pat. Nos. 4,816,567, 5,514,548, 5,545,806, 5,569,825, 5,591,669, 5,545,807; PCT Patent Application Publication No. WO 97/17852, each of which is hereby incorporated by reference in its entirety).

In certain preferred embodiments, the antibody does not specifically bind to CD19 or EGFR (epidermal growth factor receptor). In other embodiments, the antibody may be an anti-CD19 or EGFR antibody.

When the antibody comprises at least one light chain and at least one heavy chain, at least one light chain of the antibody, or at least one heavy chain of the antibody, or both may comprise an amino acid region having an amino acid motif capable of being recognized by an isoprenoid transferase. As an antibody may comprise four polypeptide chains (e.g., two heavy chains and two light chains), an antibody may comprise four amino acid motifs, each of which can be used to conjugate an active agent to the antibody via a linker. Thus, an antibody-drug conjugate may comprise 4 linkers, each conjugated to an active agent, e.g., each conjugated to the C-terminus of a different chain of the antibody. Accordingly, an antibody-drug conjugate may comprise at least one linker and at least one active agent. An antibody-drug conjugate may comprise at least two linkers, and an antibody-drug conjugate may comprise at least two active agents. An antibody-drug conjugate may comprise multiple linkers. An antibody-drug conjugate may comprise multiple active agents. In an antibody-drug conjugate that includes 2 or more active agents, the active agents may all be the same, may all be different, or may be present in any mixture or ratio.

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity Immunological binding properties of selected polypeptides can be quantified using any suitable method. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is the to specifically bind to its target, when the equilibrium binding constant ($K_d$) is ≤1 µM, e.g., ≤100 nM, preferably ≤10 nM, and more preferably 1 nM, as measured by suitable assays, such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence. Polynucleotides in accordance with the disclosure include the nucleic acid molecules encoding the heavy chain immunoglobulin molecules, and nucleic acid molecules encoding the light chain immunoglobulin molecules described herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules, and the light chain immunoglobulin molecules described herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means a polymeric boron of nucleotides of at least 10 bases in length, either ribonucleotides or deoxynucleotides or a modified form of either type of nucleotide. The term includes single and double stranded forms of DNA.

As used herein, the twenty conventional amino acids and their abbreviations follow conventional usage. See Immunology—A Synthesis (2nd Edition, E. S. Golub and D. R. Gren, Eds., Sinauer Associates, Sunderland Mass. (1991)). Stereoisomers (e.g., D-amino acids) of the twenty conventional amino acids, unnatural amino acids such as α-,α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, and most preferably at least 99 percent sequence identity.

Preferably, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present disclosure, providing that the variations in the amino acid sequence maintain at least 75%, more preferably at least 80%, 90%, 95%, and most preferably 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Preferred amino- and carboxy-termini of fragments or analogs occur near boundaries of functional domains. Structural and functional domains can be identified by comparison of the nucleotide and/or amino acid sequence data to public or proprietary sequence databases. Preferably, computerized comparison methods are used to identify sequence motifs or predicted protein conformation domains that occur in other proteins of known structure and/or function. Many methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, Calif. (1985).

The term "agent" is used herein to denote a chemical compound (such as an organic or inorganic compound, a mixture of chemical compounds), a biological macromolecule (such as a nucleic acid, an antibody, including parts thereof as well as humanized, chimeric and human antibodies and monoclonal antibodies, a protein or portion thereof, e.g., a peptide, a lipid, a carbohydrate), or an extract made from biological materials such as bacteria, plants, fungi, or animal (particularly mammalian) cells or tissues. Agents include, for example, agents whose structure is known, and those whose structure is not known. The ability of such agents to inhibit AR or promote AR degradation may render them suitable as "therapeutic agents" in the methods and compositions of this disclosure.

A "patient," "subject," or "individual" are used interchangeably and refer to either a human or a non-human animal. These terms include mammals, such as humans, primates, livestock animals (including bovines, porcines, etc.), companion animals (e.g., canines, felines, etc.) and rodents (e.g., mice and rats).

"Treating" a condition or patient refers to taking steps to obtain beneficial or desired results, including clinical results. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample. The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount.

"Administering" or "administration of" a substance, a compound or an agent to a subject can be carried out by any suitable method or route. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

As used herein, the phrase "conjoint administration" refers to any form of administration of two or more different therapeutic agents such that the second agent is administered while the previously administered therapeutic agent is still effective in the body (e.g., the two agents are simultaneously effective in the patient, which may include synergistic effects of the two agents). For example, the different therapeutic compounds can be administered either in the same formulation or in separate formulations, either concomitantly or sequentially. Thus, an individual who receives such treatment can benefit from a combined effect of different therapeutic agents.

The term "therapeutically effective amount" means a single dose or a composition administered in a multiple dose schedule that is effective for the treatment or prevention of a disease or disorder. The term "therapeutically effective amount" with regard to cancer or tumor means an amount that may decrease the number of cancer cells; decrease a size of cancer cells; inhibit cancer cells from intruding into peripheral systems or decrease the intrusion; inhibit cancer cells from spreading to other systems or decrease the spreading; inhibit cancer cells from growing; and/or ameliorate at least one symptom related to the cancer. In the treatment of cancer, the effectiveness of a drug may be assessed by time to tumor progression (TTP) and/or response rate (RR).

The term "pharmaceutically acceptable salts" used herein includes organic salts and inorganic salts. Examples thereof include hydrochloride, hydrobromide, hydroiodide, sulfate, citrate, acetate, oxalate, chloride, bromide, iodide, nitrate, bisulfate, phosphate, acidic phosphate, isonicotinate, lactate, salicylate, acidic citrate, tartrate, oleate, tannate, pantonate, bitartrate, ascorbate, succinate, maleate, gentisinate, fumarate, gluconate, glucoronate, saccharate, formate, benzoate, glutamate, methane sulfonate, ethane sulfonate, benzene sulfonate, p-toluene sulfonate, and pamoate (that is, 1,1'-methylenebis-(2-hydroxy-3-naphthoate)). The pharmaceutically acceptable salt may include another molecule (for example, acetate ions, succinate ions, and/or other counter ions).

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present disclosure can be selected by one of ordinary skilled person in the art to result chemically stable compounds which can be readily synthesized by any suitable method, such as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—CH$_2$—O-alkyl, —OP(O)(O-alkyl)$_2$ or —CH$_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, trifluoromethoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen (e.g., fluoro), a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x\text{-}y}$" when used in conjunction with a chemical moiety, such as, acyl, acyloxy, alkyl, alkenyl, alkynyl, or alkoxy is meant to include groups that contain from x to y carbons in the chain. For example, the term "$C_{x\text{-}y}$ alkyl" refers to substituted or unsubstituted saturated hydrocarbon groups, including straight-chain alkyl and branched-chain alkyl groups that contain from x to y carbons in the chain, including haloalkyl groups. Preferred haloalkyl groups include trifluoromethyl, difluoromethyl, 2,2,2-trifluoroethyl, and pentafluoroethyl. $C_0$ alkyl indicates a hydrogen where the group is in a terminal position, a bond if internal. The terms "$C_{2\text{-}y}$ alkenyl" and "$C_{2\text{-}y}$ alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

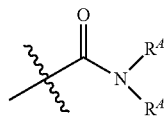

wherein each $R^A$ independently represent a hydrogen or hydrocarbyl group, or two $R^A$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

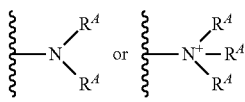

wherein each $R^A$ independently represents a hydrogen or a hydrocarbyl group, or two $R^A$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 6- or 10-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

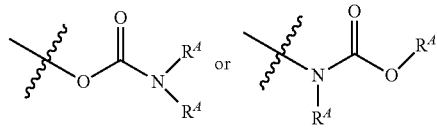

wherein each $R^A$ independently represent hydrogen or a hydrocarbyl group, such as an alkyl group, or both $R^A$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "carbocyclylalkyl", as used herein, refers to an alkyl group substituted with a carbocycle group.

The term "carbonate" is art-recognized and refers to a group $—OCO_2—R^A$, wherein $R^A$ represents a hydrocarbyl group.

The term "carboxy", as used herein, refers to a group represented by the formula $—CO_2H$.

The term "ester", as used herein, refers to a group $—C(O)OR^A$ wherein $R^A$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo. The term "dihalo", when referring to a substitution, refers to two halogens bound to a single carbon atom.

The terms "hetaralkyl" and "heteroaralkyl", as used herein, refers to an alkyl group substituted with a hetaryl group.

The term "heteroalkyl", as used herein, refers to a saturated or unsaturated chain of carbon atoms and at least one heteroatom. In certain embodiments, no two heteroatoms in a heteroalkyl are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is hetero aromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, tetrahydropyran, tetrahydrofuran, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a $=O$ or $=S$ substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a $=O$ substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_{1-6}$ alkyl, $C_{3-6}$ cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —$OSO_3H$, or a pharmaceutically acceptable salt thereof.

The term "sulfonamide" is art-recognized and refers to the group represented by the general formulae

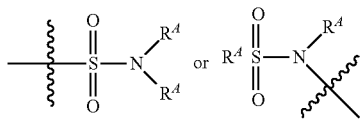

wherein each $R^A$ independently represents hydrogen or hydrocarbyl, such as alkyl, or both $R^A$ taken together with the intervening atom(s) complete a heterocycle having from 4 to 8 atoms in the ring structure.

The term "sulfoxide" is art-recognized and refers to the group —S(O)—$R^A$, wherein $R^A$ represents a hydrocarbyl.

The term "sulfonate" is art-recognized and refers to the group $SO_3H$, or a pharmaceutically acceptable salt thereof.

The term "sulfone" is art-recognized and refers to the group —$S(O)_2$—$R^A$, wherein RA represents a hydrocarbyl.

The term "thioalkyl", as used herein, refers to an alkyl group substituted with a thiol group.

The term "thioester", as used herein, refers to a group —$C(O)SR^A$ or —$SC(O)R^A$ wherein $R^A$ represents a hydrocarbyl.

The term "thioether", as used herein, is equivalent to an ether, wherein the oxygen is replaced with a sulfur.

The term "urea" is art-recognized and may be represented by the general formula

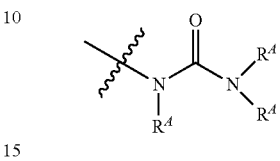

wherein each $R^A$ independently represents hydrogen or a hydrocarbyl, such as alkyl, or any occurrence of $R^A$ taken together with another and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, $3^{rd}$ Ed., 1999, John Wiley & Sons, N.Y. and Harrison et al., *Compendium of Synthetic Organic Methods*, Vols. 1-8, 1971-1996, John Wiley & Sons, N.Y. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable salt" or "salt" is used herein to refer to an acid addition salt or a basic addition salt which is suitable for or compatible with the treatment of patients.

The term "pharmaceutically acceptable acid addition salt" as used herein means any non-toxic organic or inorganic salt of any base compounds. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono or di-acid salts can be formed, and such salts may exist in either a hydrated, solvated or substantially anhydrous form. In general, the acid addition salts are more soluble in water and various hydrophilic organic solvents, and generally demonstrate higher melting points in comparison to their free base forms. The selection of the appropriate salt will be known to one skilled in the art. Other non-pharmaceutically acceptable salts, e.g., oxalates, may be used, for example, in the isolation of compounds for laboratory use, or for subsequent conversion to a pharmaceutically acceptable acid addition salt.

The term "pharmaceutically acceptable basic addition salt" as used herein means any non-toxic organic or inorganic base addition salt of any acid compounds. Illustrative inorganic bases which form suitable salts include lithium, sodium, potassium, calcium, magnesium, or barium hydroxide. Illustrative organic bases which form suitable salts include aliphatic, alicyclic, or aromatic organic amines such as methylamine, trimethylamine and picoline or ammonia. The selection of the appropriate salt will be known to a person skilled in the art.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Prodrug" or "pharmaceutically acceptable prodrug" refers to a compound that is metabolized, for example hydrolyzed or oxidized, in the host after administration to form a biologically active molecule. Typical examples of prodrugs include compounds that have biologically labile or cleavable (protecting) groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. Examples of prodrugs using ester or phosphoramidate as biologically labile or cleavable (protecting) groups are disclosed in U.S. Pat. Nos. 6,875,751, 7,585,851, and 7,964,580, the disclosures of which are incorporated herein by reference. The present disclosure includes within its scope, prodrugs of the active agents described herein. Conventional procedures for the selection and preparation of suitable prodrugs are described, for example, in "Design of Prodrugs" Ed. H. Bundgaard, Elsevier, 1985.

The phrase "pharmaceutically acceptable carrier" as used herein means a pharmaceutically acceptable material, composition or vehicle, such as a liquid or solid filler, diluent, excipient, solvent or encapsulating material useful for formulating a drug for medicinal or therapeutic use. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "Log of solubility", "LogS" or "logS" as used herein is used in the art to quantify the aqueous solubility of a compound. The aqueous solubility of a compound significantly affects its absorption and distribution characteristics. A low solubility often goes along with a poor absorption. LogS value is a unit stripped logarithm (base 10) of the solubility measured in mol/liter.

As used herein, "substantially pure" means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present.

Generally, a substantially pure composition will comprise more than about 80 percent of all macromolecular species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single macromolecular species.

Isoprenoid Transferase Recognizing Antibodies

The antibodies described herein may comprise an amino acid motif, preferably at a C-terminus of the antibody, e.g., that is recognized by an isoprenoid transferase; and the thioether bond may comprise a sulfur atom of a cysteine of the amino acid motif. The amino acid motif may be a sequence selected from CXX, CXC, XCXC, XXCC, and CYYX, wherein C represents cysteine; Y, independently for each occurrence, represents an aliphatic amino acid; and X, independently for each occurrence, represents glutamine, glutamate, serine, cysteine, methionine, alanine, or leucine. In preferred embodiments, the thioether bond comprises a sulfur atom of a cysteine of the amino acid motif.

In some embodiments, the amino acid motif is a sequence CYYX, and Y, independently for each occurrence, represents alanine, isoleucine, leucine, methionine, or valine. For example, the amino acid motif may be CVIM or CVLL.

In preferred embodiments, at least one of the seven amino acids preceding the amino acid motif is glycine. In preferred embodiments, at least three of the seven amino acids preceding the amino acid motif are each independently selected from glycine and proline. In some embodiments, each of the one, two, three, four, five, six, seven, eight, nine, or ten amino acids preceding the amino acid motif is glycine, preferably seven. In certain preferred embodiments, at least three of the seven amino acids preceding the amino acid motif are each independently selected from glycine, aspartic acid, arginine, and serine.

In some embodiments, the antibody comprises the amino acid sequence GGGGGGGCVIM, preferably at a C-terminus.

In preferred embodiments, the antibody comprises an amino acid motif capable of being recognized by an isoprenoid transferase. For example, at least one C-terminus of the antibody may comprise an amino acid motif capable of being recognized by an isoprenoid transferase (e.g., as a substrate, for example, prior to forming the antibody-drug conjugate, or as a product of an isoprenoid transferase, for example, after forming the antibody-drug conjugate). The antibody may further comprise a spacer, such as an amino acid or a stretch of amino acids that links a peptide chain of the antibody to the amino acid motif. The spacer may consist of 1 to 20 consecutive amino acids, preferably 7-20 amino acids. In some embodiments, glycine and proline are preferred amino acids for the spacer, and may be used in any combination, such as a series of at least about 1, 2, 3, 4, 5, 6, 7, 8, 9, or 10 glycines, or a series of about 1, 2, 3, 4, 5, 6, 7, 8, 9, or 10 glycines. In other embodiments the amino acid motif are each independently selected from glycine, aspartic acid, arginine, and serine. The antibody may comprise an addition or deletion at a carboxy terminus, e.g., relative to a form of the antibody not included in an ADC.

Examples of isoprenoid transferases include farnesyl protein transferase (FTase) and geranylgeranyl transferase (GGTase), which can catalyze the transfer of a farnesyl or geranylgeranyl group to at least one C-terminal cysteine of a target protein. A GGTase may be classified as either GGTase I or GGTase II. FTase and GGTase I may recognize a CAAX motif, and GGTase II may recognize a XXCC, XCXC, or CXX motif, wherein C represents cysteine, A represents an aliphatic amino acid (e.g., isoleucine, valine, methionine, leucine), and each X independently represents, for example, glutamine, glutamate, serine, cysteine, methionine, alanine, or leucine (see Nature Rev. Cancer, 5(5):405-12 (2005); Nature Chemical Biology 17:498-506 (2010); Lane K T, Bees L S, J. Lipid Research, 47:681-699 (2006); Kasey P J, Seabra M C, J. Biological Chemistry, 271(10): 5289-5292 (1996), each of which is hereby incorporated by reference in its entirety).

The antibody-drug conjugates according to the present disclosure may comprise an amino acid motif, such as CYYX, XXCC, XCXC, or CXX, preferably CYYX (wherein, C represents cysteine, Y represents an aliphatic amino acid, such as leucine, isoleucine, valine, and/or methionine, and X represents an amino acid that determines a substrate specificity of the isoprenoid transferase, such as glutamine, glutamate, serine, cysteine, methionine, alanine, and/or leucine).

Isoprenoid transferases from various sources may be used. For example, the isoprenoid transferase may be obtained from a human, animal, plant, bacteria, virus, or other source. In some embodiments, a naturally occurring isoprenoid transferase is used. In some embodiments, a naturally-modified or artificially-modified isoprenoid transferase may be used. For example, the isoprenoid transferase may comprise one or more amino acid substitutions, additions, and/or deletions, and/or the isoprenoid transferase may be modified by the addition of at least one of Histidine-tag, GST, GFP, MBP, CBP, Isopeptag, BCCP, Myc-tag, Calmodulin-tag, FLAG-tag, HA-tag, Maltose binding protein-tag, Nus-tag, Glutathione-S-transferase-tag, Green fluorescent protein-tag, Thioredoxin-tag, S-tag, Softag 1, Softag 3, Strep-tag, SBP-tag, Ty-tag, and the like.

Isoprenoid transferases recognize an isosubstrate and/or a substrate. The term isosubstrate refers to a substrate analog comprising a chemical modification. Isoprenoid transferases can alkylate a specific amino acid motif (for example, a CAAX motif) at the C-terminus of an antibody (see, e.g., Duckworth, B P et al., ChemBioChem, 8:98 (2007); Uyen T T et al., ChemBioChem, 8:408 (2007); Labadie, G R et al., J. Org. Chem., 72(24):9291 (2007); Wollack, J W et al., ChemBioChem, 10:2934 (2009), each of which is hereby incorporated by reference). A functionalized antibody may be produced using an isoprenoid transferase and an isosubstrate, which may alkylate a C-terminal cysteine.

The isosubstrate may be, for example, the compound of formula:

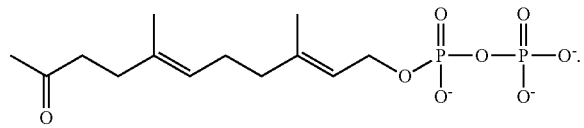

The cysteine of a C-terminal CAAX motif may be bound to an isosubstrate using an isoprenoid transferase. In some embodiments, part of the motif, e.g., AAX, may subsequently be removed by a protease, e.g., leaving only the cysteine to which the isoprenoid is bound. The cysteine may optionally be methylated at the carboxyl terminus, e.g., by an enzyme (see, e.g., Bell, I M, J. Med. Chem., 47(8):1869 (2004)), which is hereby incorporated by reference).

The antibody-drug conjugates of the disclosure may be prepared using any suitable method, including molecular biology and cell biology methods. For example, transient or stable transfection methods may be used. Genetic sequences encoding a specific amino acid motif capable of being recognized by an isoprenoid transferase may be inserted into a plasmid vector, of which many suitable vectors are known, using standard PCR and/or ligation technologies so as to express an antibody having the specific amino acid motif at a C-terminus thereof. An antibody having at least one amino acid motif capable of being recognized by the isoprenoid transferase may thus be expressed in a suitable host, e.g., a CHO cell or in *E. coli*.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and any suitable method may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

The active agent may be a drug, toxin, affinity ligand, detection probe, or combination of any of the foregoing. The active agent may be an immunomodulatory compound, an anticancer agent, an antiviral agent, an antibacterial agent, an antifungal agent, an antiparasitic agent, or a combination thereof. In some embodiments, the active agent may be chemotherapeutic agents and toxins, as disclosed herein. For example, in some embodiments, the active agent may be amanitin, auristatin, calicheamicin, camptothecin, cryptophycin, daunomycin, dolastatin, doxorubicin, duocarmycin, epothilone, esperamicin, geldanamycin, maytansinoid, methotrexate, monomethyl auristatin E ("MMAE"), monomethyl auristatin F ("MMAF"), pyrrolobenzodiazepine, rhizoxin, SG2285, tubulysin, vindesine, toxoid, or a derivative of any one of the foregoing. In some embodiments, at least one active agent may be taltobulin. In some embodiments, at least one active agent may be azonafide. In some embodiments, the active agent may be a pyrrolobenzodiazepine dimer, as disclosed herein.

In some embodiments, the active agent is a chemotherapeutic agent or a toxin. The active agent may be selected from erlotinib; bortezomib; fulvestrant; sutent; letrozole; imatinib mesylate; PTK787/ZK 222584; oxaliplatin; 5-fluorouracil; leucovorin; rapamycin (Sirolimus); lapatinib; lonafarnib; sorafenib; gefitinib; AG1478; AG1571; alkylating agents (for example, thiotepa or cyclophosphamide); alkyl sulfonate (for example, busulfan, improsulfan, or piposulfan); aziridine (for example, benzodopa, carboquone, meturedopa, or uredopa); ethyleneimine, methylmelamine, altretamine, triethylenemelamine, triethylenephosphoramide, triethylenethiophosphoramide, trimethylolmelamine; acetogenins (for example, bullatacin or bullatacinone); camptothecin; a derivative or metabolite of camptothecin (e.g., SN-38); topotecan; bryostatin; callystatin; CC-1065 (including its adozelesin, carzelesin, or bizelesin synthetic analogs); cryptophycins (for example, cryptophycin 1 or cryptophycin 8); dolastatin; duocarmycin (including synthetic analogs, e.g., KW-2189 and CB1-TM1); eleutherobin; pancratistatin; sarcodictyin; spongistatin; nitrogen mustard (for example, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, or uracil mustard); nitrousurea (for example, carmustine, chlorozotocin, fotemustine, lomustine, nimustine, or ranimnustine); antibiotics (for example, enediyne antibiotics such as calicheamycin selected from calicheamycin gamma II and calicheamycin omega II, or dynemicin including dynemicin A); bisphosphonate (for example, clodronate; esperamicin, neocarzinostatin chromophore, or related chromoprotein enediyne antibiotic chromophores, aclacinomysins, actinomycin, anthramycin, azaserine, bleomycins, cactinomycin, carabicin, carninomycin, carzinophilin, chromomycins, dactinomycin, daunorubicin, detorubicin, 6-diazo-5-oxo-L-norleucine, doxorubicin (for example, morpholino-doxorubicin, cyanomorpholino-doxorubicin, 2-pyrrolino-doxorubicin, liposomal doxorubicin, or deoxydoxorubicin), epirubicin, esorubicin, marcellomycin, mitomycins (for example, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, or zorubicin); antimetabolites (for example, 5-fluorouracil); folic acid analogs (for example, denopterin, methotrexate, pteropterin, or trimetrexate); purine analogs (for example, fludarabine, 6-mercaptopurine, thiamiprine, or thiguanine); pyrimidine analogs (for example, ancitabine, azacitidine, 6-azauridine, carmofur, cytarabine, dideoxyuridine, doxifluridine, enocitabine, or floxuridine); androgens (for example, calusterone, dromostanolone propionate, epitiostanol, mepitiostane), or testolactone); anti-adrenals (for example, aminoglutethimide, mitotane, or trilostane); folic acid replenisher (for example, folinic acid); aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; epothilone; etoglucid; gallium nitrate; hydroxyurea; lentinan; lonidainine; maytansinoids (for example, maytansine or ansamitocins); trichothecenes (particularly T-2 toxin, verracurin A, roridin A, or anguidine); mitoguazone; mitoxantrone; mopidanmol; nitraerine; pentostatin; phenamet; pirarubicin; losoxantrone; 2-ethylhydrazide; procarbazine; polysaccharide K complex; razoxane; rhizoxin; sizofiran; spirogermanium; tenuazonic acid; triaziquone; 2,2',2"-trichlorotriethylamine; trichothecenes (particularly, T-2 toxin, verracurin A, roridin A, and anguidine); urethane; vindesine; dacarbazine; mannomustine; mitobronitol; mitolactol; pipobroman; gacytosine; arabinoside; cyclophosphamide; thiotepa; taxoids (for example, paclitaxel), ABRAXANE™ cremophor-free, albumin-engineered nanoparticle formulation of paclitaxel, doxetaxel; chlorambucil; gemcitabine; 6-thioguanine; mercaptopurine; platinum analog (for example, cisplatin or carboplatin); vinblastine; platinum; etoposide, ifosfamide; mitoxantrone; vincristine; vinorelbine; novantrone; teniposide; edatrexate; daunomycin; aminopterin; xeloda; ibandronate; CPT-11; topoisomerase inhibitor (RFS 2000); difluoromethylornithine; retinoid (for example, retinoic acid); capecitabine, and pharmaceutically acceptable salts, solvates, acids, or derivatives thereof, but is not necessarily limited thereto.

The active agent may be selected from (i) anti-hormonal agents that act to regulate or inhibit hormone action on tumors such as anti-estrogens and selective estrogen receptor modulators, including, for example, tamoxifen, raloxifene, droloxifene, 4-hydroxytamoxifen, trioxifene, keoxifene, LY117018, onapristone, and toremifene; (ii) aromatase inhibitors that inhibit aromatase enzyme, which regulates estrogen production in the adrenal glands, for example, 4(5)-imidazoles, aminoglutethimide, megestrol acetate, exemestane, letrozole, and anastrozole; (iii) anti-androgens such as flutamide, nilutamide, bicalutamide, leuprolide, and goserelin; as well as troxacitabine (a 1,3-dioxolane nucleoside cytosine analog); (iv) aromatase inhibitors; (v) protein kinase inhibitors; (vi) lipid kinase inhibitors; (vii) antisense oligonucleotides, particularly those that inhibit expression of genes in signaling pathways implicated in adherent cells, for example, PKC-alpha, Raf, H-Ras; (viii) ribozyme, for example, VEGF inhibitor such as ribozyme and HER2 expression inhibitors; (ix) vaccines such as a gene therapy vaccine; ALLOVECTIN® vaccine, LEUVECTIN vaccine, VAXID vaccine; PROLEUKIN®r1L-2; LURTOTECAN® topoisomerase 1 inhibitor; ABARELIX® rmRH; (x) an anti-angiogenic agent such as Bevacizumab; (xi) an affinity ligand, wherein the affinity ligand is a substrate, an inhibitor, a stimulating agent, a neurotransmitter, a radioisotope, or a combination of any of the foregoing; (xii) a radioactive label, $^{32}P$, $^{35}S$, a fluorescent dye, an electron dense reagent, an enzyme, biotin, streptavidin, dioxigenin, a hapten, an immunogenic protein, a nucleic acid molecule with a sequence complementary to a target, or a combination of any of the foregoing; (xii) an immunomodulatory compound, an anti-cancer agent, an anti-viral agent, an anti-bacterial agent, an anti-fungal agent, and an anti-parasitic agent, or a combination of any of the foregoing; (xiv) tamoxifen, raloxifene, droloxifene, 4-hydroxytamoxifen, trioxifene, keoxifene, LY117018, onapristone, or toremifene; (xv) 4(5)-imidazoles, aminoglutethimide, megestrol acetate, exemestane, letrozole, or anastrozole; (xvi) flutamide, nilutamide, bicalutamide, leuprolide, goserelin, or troxacitabine; (xvii) an aromatase inhibitor; (xvii) a protein kinase inhibitor; (xix) a lipid kinase inhibitor; (xx) an antisense oligonucleotide; (xxi) a ribozyme; (xxii) a vaccine; (xxiii) an anti-angiogenic agent; and (xxiv) pharmaceutically acceptable salts, solvates, acids, or derivatives thereof.

In some embodiments, the least one active agent is taltobulin or azonafide.

In some embodiments, the active agent is amanitin, auristatin, calicheamicin, camptothecin, camptothecin derivatives and metabolites (SN-38), cryptophycin, daunomycin, dolastatin, doxorubicin, duocarmycin, epothilone, esperamicin, geldanamycin, maytansinoid, methotrexate, monomethyl auristatin E ("MMAE"), monomethyl auristatin F ("MMAF"), pyrrolobenzodiazepine, rhizoxin, SG2285, tubulysin, vindesine, toxoid, or a derivative of any one of the foregoing. In certain embodiments, active agent is amanitin, MMAE, or MMAF, or a derivative of any one of the foregoing.

In addition, cytokines may be used as the active agent. Cytokines are small cell-signaling protein molecules that are secreted by numerous cells and are a category of signaling molecules used extensively in intercellular communication. The cytokines include monokines, lymphokines, traditional polypeptide hormones, and the like. Examples of the cytokines include growth hormone (for example, human growth hormone, N-methionyl human growth hormone, or bovine growth hormone); parathyroid hormone; thyroxine; insulin; proinsulin; relaxin; prorelaxin; glycoprotein hormone (for example, follicle stimulating hormone (FSH), thyroid stimulating hormone (TSH), or luteinizing hormone (LH)); hepatic growth factor; fibroblast growth factor; prolactin; placental lactogen; tumor necrosis factor-α, tumor necrosis factor-β; mullerian-inhibiting substance; mouse gonadotropin-associated peptide; inhibin; activin; vascular endothelial growth factor; integrin, thrombopoietin (TPO); nerve growth factor (for example, NGF-β); platelet-growth factor; transforming growth factor (TGF) (for example, TGF-α or TGF-β); insulin-like growth factor-I, insulin-like growth factor-II; erythropoietin (EPO); osteoinductive factor; interferon (for example, interferon-α, interferon-β, or interferon-γ); colony stimulating factor (CSF) (for example, macrophage-CSF (M-CSF), granulocyte-macrophage-CSF (GM-CSF), or granulocyte-CSF (G-CSF)); interleukin (IL) (for example, IL-1, IL-1α, IL-2, IL-3, IL-4, IL-5, IL-6, IL-7, IL-8, IL-9, IL-10, IL-11, or IL-12); tumor necrosis factor (TNF) (for example, TNF-α or TNF-β); and polypeptide factor (for example, LIF or kit ligand), but are not limited thereto. Further, the term "cytokine" also includes cytokines from natural sources or recombinant cell cultures and biologically active equivalents of the native sequence cytokines.

The term "toxin" refers to substances that are poisonous to living cells or organisms. Toxins may be small molecules, peptides or proteins capable of causing cell dysfunction or cell death after contact with or absorption by body tissue, e.g., through an interaction with one or more biological macromolecules such as enzymes or cell receptors. Toxins include plant toxins and animal toxins. Examples of animal toxins include diphtheria toxin, botulinum toxin, tetanus toxin, dysentery toxin, cholera toxin, tetrodotoxin, brevetoxin, and ciguatoxin, but are not limited thereto. Examples of plant toxins include ricin and AM-toxin, but are not limited thereto.

Examples of small molecule toxins include auristatin, tubulysin, geldanamycin (Kerr et al., 1997, Bioconjugate Chem. 8(6):781-784), maytansinoid (EP 1391213, ACR 2008, 41, 98-107), calicheamicin (U.S. Patent Publication No. 2009/0105461, Cancer Res. 1993, 53, 3336-3342), daunomycin, doxorubicin, methotrexate, vindesine, SG2285 (Cancer Res. 2010, 70(17), 6849-6858), dolastatin, dolastatin analogs, auristatin (U.S. Pat. No. 5,635,483), cryptophycin, camptothecin, a derivative or metabolite of camptothecin, (e.g., SN-38), rhizoxin derivative, CC-1065 analog or derivative, duocarmycin, enediyne antibiotic, esperamicin, epothilone, pyrrolobenzodiazepine (PBD) derivatives, amanitin, derivatives of amanitin, α-amanitin, aplidine, azonafide, and toxoid, but are not limited thereto. Toxins may exhibit cytotoxicity and cell growth-inhibiting activity by tubulin binding, DNA binding, topoisomerase suppression, and the like.

"Detectable moiety" or a "label" refers to a composition detectable by spectroscopic, photochemical, biochemical, immunochemical, radioactive, or chemical means. For example, useful labels include $^{32}P$, $^{35}S$, fluorescent dyes, electron-dense reagents, enzymes (for example, enzymes commonly used in an ELISA), biotin-streptavidin, dioxigenin, haptens, and proteins for which antisera or monoclonal antibodies are available, or nucleic acid molecules with a sequence complementary to a target. The detectable moiety often generates a measurable signal, such as a radioactive, chromogenic, or fluorescent signal, that may be used to quantify the amount of bound detectable moiety in a sample. Quantitation of the signal may be achieved, for example, by scintillation counting, densitometry, flow cytometry, ELISA, or direct analysis by mass spectrometry of intact or subsequently digested peptides (one or more peptide may be assessed).

The term "probe" as used herein refers to a material that may (i) provide a detectable signal, (ii) interact a first probe or a second probe to modify a detectable signal provided by the first or second probe, such as fluorescence resonance energy transfer (FRET), (iii) stabilize an interaction with an antigen or a ligand or increase binding affinity; (iv) affect electrophoresis mobility or cell-intruding activity by a physical parameter such as charge, hydrophobicity, etc., or (v) control ligand affinity, antigen-antibody binding, or ionic complex formation.

The active agent may be an immunomodulatory compound, an anticancer agent, an antiviral agent, an antibacterial agent, an antifungal agent, an antiparasitic agent, or a combination thereof.

An immunomodulatory compound may be selected from aminocaproic acid, azathioprine, bromocriptine, chlorambucil, chloroquine, cyclophosphamide, cyclosporine, cyclosporine A, danazol, dehydroepiandrosterone, dexamethasone, etanercept, hydrocortisone, hydroxychloroquine, infliximab, meloxicam, methotrexate, mycophenylate mofetil, prednisone, sirolimus, and tacrolimus. An anticancer agent may be selected from 1-methyl-4-phenylpyridinium ion, 5-ethynyl-1-beta-D-ribofuranosylimidazole-4-carboxamide (EICAR), 5-fluorouracil, 9-aminocamptothecin, actinomycin D, asparaginase, bicalutamide, bis-chloroethylnitrosourea (BCNU), bleomycin, bleomycin A2, bleomycin B2, busulfan, camptothecin, a derivative or metabolite of camptothecin, e.g., SN-38, carboplatin, carmustine, CB1093, chlorambucil, cisplatin, crisnatol, cyclophosphamide, cytarabine, cytosine arabinoside, cytoxan, dacarbazine, dactinomycin, daunorubicin, decarbazine, deferoxamine, demethoxy-hypocrellin A, docetaxel, doxifluridine, doxorubicin, EB1089, epirubicin, etoposide, floxuridine, fludarabine, flutamide, gemcitabine, goserelin, hydroxyurea, idarubicin, ifosfamide, interferon-α, interferon-γ, irinotecan, KH1060, leuprolide acetate, lomustine, lovastatin, megestrol, melphalan, mercaptopurine, methotrexate, mitomycin, mitomycin C, mitoxantrone, mycophenolic acid, nitrogen mustard, nitrosourea, paclitaxel, peplomycin, photosensitizer Pe4, phthalocyanine, pirarubicin, plicamycin, procarbazine, raloxifene, raltitrexed, revlimid, ribavirin, staurosporine, tamoxifen, teniposide, thalomid, thapsigargin, thioguanine, tiazofurin, topotecan, treosulfan, trimetrexate, tumor necrosis factor, velcade, verapamil, verteporfin, vinblastine, vincristine, vinorelbine, and zorubicin. An antiviral agent may be selected from pencicyclovir, valacyclovir, gancicyclovir, foscarnet, ribavirin, idoxuridine, vidarabine, trifluridine, acyclovir, famcicyclovir, amantadine, rimantadine, cidofovir, antisense oligonucleotide, immunoglobulin, and interferon. An antibacterial agent may be selected from chloramphenicol, vancomycin, metronidazole, trimethoprin, sulfamethazole, quinupristin, dalfopristin, rifampin, spectinomycin, and nitrofurantoin. The antifungal agent may be selected from amphotericin B, candicidin, filipin, hamycin, natamycin, nystatin, rimocidin, bifonazole, butoconazole, clotrimazole, econazole, fenticonazole, isoconazole, ketoconazole, luliconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, tolnaftate, undecylenic acid, crystal violet, balsam of peru, ciclopirox olamine, piroctone olamine, zinc pyrithione, and selenium sulfide. An antiparasitic agent may be selected from mebendazole, pyrantel pamoate, thiabendazole, diethylcarbamazine, ivermectin, niclosamide, praziquantel, albendazole, rifampin, amphotericin B, melarsoprol, eflornithine, metronidazole, tinidazole, and miltefosine.

The antibody may comprise an amino acid motif selected from Ab-HC-(G)$_z$CVIM, Ab-HC-(G)$_z$CVLL, Ab-LC-(G)$_z$CVIM, and Ab-LC-(G)$_z$CVLL, Ab-HC-(G)$_z$CVIM/LC-(G)$_z$CVIM, Ab-HC-(G)$_z$CVLL/LC-(G)$_z$CVIM, Ab-HC-(G)$_z$CVIM/LC-(G)$_z$CVLL, and Ab-HC-(G)$_z$CVLL/LC-(G)$_z$CVLL, wherein Ab represents an antibody (e.g., as disclosed herein), Ab-HC- represents a heavy chain of an antibody (e.g., the heavy chains disclosed herein), Ab-LC- represents a light chain of an antibody (e.g., the light chains disclosed herein), G represents a glycine, C represents cysteine, V represents valine, I represents isoleucine, M represents methionine, L represents leucine, and z is an integer from 0 to 20, preferably from 1 to 10.

General Method for Preparing Antibodies

Various procedures known within the art may be used for the production of polyclonal or monoclonal antibodies directed against a given target, such as, for example, CD19, a tumor associated antigen or other target, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

In some embodiments, the antibodies of the disclosure are monoclonal antibodies. Monoclonal antibodies are generated, for example, by using the procedures set forth in the Examples provided herein. Antibodies are also generated, e.g., by immunizing BALB/c mice with combinations of cell transfectants expressing high levels of a given target on their surface. Hybridomas resulting from myeloma/B cell fusions are then screened for reactivity to the selected target.

Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986) pp. 59-103) Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the disclosure can be readily isolated and sequenced using conventional procedures (e.g., by using oligonucleotide probes that are capable of binding specifically to genes encoding the heavy and light chains of murine antibodies). The hybridoma cells of the disclosure serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the disclosure, or can be substituted for the variable domains of one antigen-combining site of an antibody of the disclosure to create a chimeric bivalent antibody.

Monoclonal antibodies of the disclosure include humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')$_2$ or other antigen-binding subsequences of antibodies) that are principally comprised of the sequence of a human immunoglobulin, and contain minimal sequence derived from a non-human immunoglobulin. Humanization is performed, e.g., by following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539). In some instances, Fv framework residues of the human immunoglobulin are replaced by corresponding non-human residues. Humanized antibodies also comprise, e.g., residues which are found neither in the recipient antibody nor in the imported CDR or framework sequences. In general, the humanized antibody includes substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also includes at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Fully human antibodies are antibody molecules in which the entire sequence of both the light chain and the heavy chain, including the CDRs, arise from human genes. Such antibodies are termed "human antibodies", or "fully human antibodies" herein. Monoclonal antibodies can be prepared by using trioma technique; the human B-cell hybridoma technique (see Kozbor, et al., 1983 Immunol Today 4: 72); and the EBV hybridoma technique to produce monoclonal antibodies (see Cole, et al., 1985 In: MONOCLONAL ANTIBODIES AND CANCER THERAPY, Alan R. Liss, Inc., pp. 77-96). Monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. An example of such a nonhuman animal is a mouse termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

An example of a method of producing a nonhuman host, exemplified as a mouse, lacking expression of an endogenous immunoglobulin heavy chain is disclosed in U.S. Pat. No. 5,939,598. It can be obtained by a method, which includes deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen and a correlative method for selecting an antibody that binds specifically to the relevant epitope with high affinity are disclosed in PCT publication WO 99/53049.

The antibody can be expressed by a vector containing a DNA segment encoding the single chain antibody described above.

These can include vectors, liposomes, naked DNA, adjuvant-assisted DNA. gene gun, catheters, etc. Vectors include chemical conjugates such as described in WO 93/64701, which has targeting moiety (e.g., a ligand to a cellular surface receptor), and a nucleic acid binding moiety (e.g., polylysine), viral vector (e.g., a DNA or RNA viral vector), fusion proteins such as described in PCT/US 95/02140 (WO 95/22618) which is a fusion protein containing a target moiety (e.g., an antibody specific for a target cell) and a nucleic acid binding moiety (e.g., a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g., infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g., adenovirus, HSV) to a desired location. Additionally, the particles can be delivered by intracerebroventricular (icy) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266:292-305 (1994)). Other methods that can be used include catheters, intravenous, parenteral, intraperitoneal and subcutaneous injection, and oral or other suitable routes of administration.

Bispecific antibodies are antibodies that have binding specificities for at least two different antigens. In the present case, one of the binding specificities is for a target such as CD19 or any fragment thereof. The second binding target is any other antigen, and advantageously is a cell-surface protein or receptor or receptor subunit.

Many methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13 May 1993, and in Traunecker et al., EMBO J., 10:3655-3659 (1991).

Bispecific and/or monovalent antibodies of the disclosure can be made using any of a variety of art-recognized techniques, including those disclosed in application WO 2012/023053, filed Aug. 16, 2011, the contents of which are hereby incorporated by reference in their entirety. The methods described in WO 2012/023053 generate bispecific antibodies that are identical in structure to a human immunoglobulin. This type of molecule is composed of two copies of a unique heavy chain polypeptide, a first light chain variable region fused to a constant Kappa domain and second light chain variable region fused to a constant Lambda domain Each combining site displays a different antigen specificity to which both the heavy and light chain contribute. The light chain variable regions can be of the Lambda or Kappa family and are preferably fused to a Lambda and Kappa constant domains, respectively. This is preferred in order to avoid the generation of non-natural polypeptide junctions. However it is also possible to obtain bispecific antibodies of the disclosure by fusing a Kappa light chain variable domain to a constant Lambda domain for a first specificity and fusing a Lambda light chain variable domain to a constant Kappa domain for the second specificity. The bispecific antibodies described in WO 2012/023053 are referred to as IgGκλ antibodies or "κλ bodies," a new fully human bispecific IgG format. This κλ-body format allows the affinity purification of a bispecific antibody that is undistinguishable from a standard IgG molecule with characteristics that are undistinguishable from a standard monoclonal antibody and, therefore, favorable as compared to previous formats.

An essential step of the method is the identification of two antibody Fv regions (each composed by a variable light chain and variable heavy chain domain) having different antigen specificities that share the same heavy chain variable domain. Numerous methods have been described for the generation of monoclonal antibodies and fragments thereof. (See, e.g., Antibodies: A Laboratory Manual, Harlow E, and Lane D, 1988, Cold Spring Harbor Laboratory Press, Cold Spring Harbor, N.Y., incorporated herein by reference). Fully human antibodies are antibody molecules in which the sequence of both the light chain and the heavy chain, including the CDRs 1 and 2, arise from human genes. The CDR3 region can be of human origin or designed by synthetic means. Such antibodies are termed "human antibodies", or "fully human antibodies" herein. Human monoclonal antibodies can be prepared by using the trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

Monoclonal antibodies are generated, e.g., by immunizing an animal with a target antigen or an immunogenic fragment, derivative or variant thereof. Alternatively, the animal is immunized with cells transfected with a vector containing a nucleic acid molecule encoding the target antigen, such that the target antigen is expressed and associated with the surface of the transfected cells. A variety of suitable techniques for producing xenogenic non-human animals are well-known in the art. For example, see U.S. Pat. Nos. 6,075,181 and 6,150,584, which is hereby incorporated by reference in its entirety.

Alternatively, the antibodies are obtained by screening a library that contains antibody or antigen binding domain sequences for binding to the target antigen. This library is prepared, e.g., in bacteriophage as protein or peptide fusions to a bacteriophage coat protein that is expressed on the surface of assembled phage particles and the encoding DNA sequences contained within the phage particles (i.e., "phage displayed library").

Hybridomas resulting from myeloma/B cell fusions are then screened for reactivity to the target antigen. Monoclonal antibodies are prepared, for example, using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

Although not strictly impossible, the serendipitous identification of different antibodies having the same heavy chain variable domain but directed against different antigens is highly unlikely. Indeed, in most cases the heavy chain contributes largely to the antigen binding surface and is also the most variable in sequence. In particular the CDR3 on the heavy chain is the most diverse CDR in sequence, length and structure. Thus, two antibodies specific for different antigens will almost invariably carry different heavy chain variable domains.

The methods disclosed in application WO 2012/023053 overcomes this limitation and greatly facilitates the isolation of antibodies having the same heavy chain variable domain by the use of antibody libraries in which the heavy chain variable domain is the same for all the library members and thus the diversity is confined to the light chain variable domain. Such libraries are described, for example, in applications WO 2010/135558 and WO 2011/084255, each of which is hereby incorporated by reference in its entirety. However, as the light chain variable domain is expressed in conjunction with the heavy variable domain, both domains can contribute to antigen binding. To further facilitate the process, antibody libraries containing the same heavy chain variable domain and either a diversity of Lambda variable light chains or Kappa variable light chains can be used in parallel for in vitro selection of antibodies against different antigens. This approach enables the identification of two antibodies having a common heavy chain but one carrying a Lambda light chain variable domain and the other a Kappa light chain variable domain that can be used as building blocks for the generation of a bispecific antibody in the full immunoglobulin format of the disclosure. The bispecific antibodies of the disclosure can be of different Isotypes and their Fc portion can be modified in order to alter the bind properties to different Fc receptors and in this way modify the effectors functions of the antibody as well as it pharmacokinetic properties. Numerous methods for the modification of the Fc portion have been described and are applicable to antibodies of the disclosure. (see for example Strohl, W R Curr Opin Biotechnol 2009 (6):685-91; U.S. Pat. No. 6,528,624; PCT/US2009/0191199 filed Jan. 9, 2009). The methods of the disclosure can also be used to generate bispecific antibodies and antibody mixtures in a F(ab') 2 format that lacks the Fc portion.

The common heavy chain and two different light chains are co-expressed into a single cell to allow for the assembly of a bispecific antibody of the disclosure. If all the polypeptides get expressed at the same level and get assembled equally well to form an immunoglobulin molecule then the ratio of monospecific (same light chains) and bispecific (two different light chains) should be 50%. However, it is likely that different light chains are expressed at different levels and/or do not assemble with the same efficiency. Therefore, a means to modulate the relative expression of the different polypeptides is used to compensate for their intrinsic expression characteristics or different propensities to assemble with the common heavy chain. This modulation can be achieved via promoter strength, the use of internal ribosome entry sites (IRES) featuring different efficiencies or other types of regulatory elements that can act at transcriptional or translational levels as well as acting on mRNA stability. Different promoters of different strength could include CMV (Immediate-early Cytomegalovirus virus promoter); EF1-1α (Human elongation factor 1α-subunit promoter); Ubc (Human ubiquitin C promoter); SV40 (Simian virus 40 promoter). Different IRES have also been described from mammalian and viral origin. (See e.g., Hellen C U and Sarnow P. Genes Dev 2001 15: 1593-612). These IRES can greatly differ in their length and ribosome recruiting efficiency. Furthermore, it is possible to further tune the activity by introducing multiple copies of an IRES (Stephen et al. 2000 Proc Natl Acad Sci USA 97: 1536-1541). The modulation of the expression can also be achieved by multiple sequential transfections of cells to increase the copy number of individual genes expressing one or the other light chain and thus modify their relative expressions. The Examples provided herein demonstrate that controlling the relative expression of the different chains is critical for maximizing the assembly and overall yield of the bispecific antibody.

The co-expression of the heavy chain and two light chains generates a mixture of three different antibodies into the cell culture supernatant: two monospecific bivalent antibodies and one bispecific bivalent antibody. The latter has to be purified from the mixture to obtain the molecule of interest. The method described herein greatly facilitates this purification procedure by the use of affinity chromatography media that specifically interact with the Kappa or Lambda light chain constant domains such as the CaptureSelect Fab Kappa and CaptureSelect Fab Lambda affinity matrices (BAC BV, Holland). This multi-step affinity chromatography purification approach is efficient and generally applicable to antibodies of the disclosure. This is in sharp contrast to specific purification methods that have to be developed and optimized for each bispecific antibodies derived from quadromas or other cell lines expressing antibody mixtures. Indeed, if the biochemical characteristics of the different antibodies in the mixtures are similar, their separation using standard chromatography technique such as ion exchange chromatography can be challenging or not possible at all.

Other suitable purification methods include those disclosed in US2013/0317200, the contents of which are hereby incorporated by reference in their entirety.

In other embodiments of producing bispecific antibodies, antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface includes at least a part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the disclosure. Alternatively, an anti-antigenic arm of an immunoglobulin molecule can be combined with an arm which binds to a triggering molecule on a leukocyte such as a T-cell receptor molecule (e.g., CD2, CD3, CD28, or B7), or Fc receptors for IgG (FcγR), such as FcγRI (CD64), FcγRII (CD32) and FcγRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate antibodies are also within the scope of the present disclosure. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the disclosure with respect to effector function, so as to enhance, e.g., the effectiveness of the antibody in treating cancer and/or other diseases and disorders associated with aberrant CD19 expression and/or activity. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

Conjugated Antibodies

The disclosure also pertains to conjugated antibodies, also referred to herein as immunoconjugates, comprising an antibody or antigen-binding fragment thereof conjugated to a cytotoxic agent such as a toxin (e.g., an enzymatically active toxin of bacterial, fungal, plant, or animal origin, or fragments thereof), or a radioactive isotope (i.e., a radioconjugate).

In some embodiments, the toxin is a microtubule inhibitor or a derivative thereof. In some embodiments, the toxin is a dolastatin or a derivative thereof. In some embodiments, the toxin is auristatin E, AFP, MMAF, MMAE, MMAD, DMAF, or DMAE. In some embodiments, the toxin is a maytansinoid or maytansinoid derivative. In some embodiments, the toxin is DM1 or DM4. In some embodiments, the toxin is a nucleic acid damaging toxin. In some embodiments, the toxin is a duocarmycin or derivative thereof. In some embodiments, the toxin is a calicheamicin or a derivative thereof. In some embodiments, the agent is a pyrrolobenzodiazepine or a derivative thereof.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$In, $^{90}$Y, and $^{186}$Re.

Conjugates of the antibody and cytotoxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis-(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun 133:1335-2549 (1984); Jansen et al., Immunological Reviews 62:185-216 (1982); and Vitetta et al., Science 238:1098 (1987).

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pyridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide]hexanoate (Pierce Chem. Co. Cat. #2165-G); and (v) sulfo-NHS (N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody can be prepared by any suitable methods, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257: 286-288 (1982) via a disulfide-interchange reaction.

Use of Anti-CD19 Antibodies

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the disclosure, which include a conjugate of the disclosure, are used to treat or alleviate a symptom associated with a cancer, such as, by way of non-limiting example, leukemias, lymphomas, breast cancer, colon cancer, ovarian cancer, bladder cancer, prostate cancer, glioma, lung & bronchial cancer, colorectal cancer, pancreatic cancer, esophageal cancer, liver cancer, urinary bladder cancer, kidney and renal pelvis cancer, oral cavity & pharynx cancer, uterine corpus cancer, and/or melanoma The present disclosure also provides methods of treating or alleviating a symptom associated with a cancer. A therapeutic regimen can include identifying a subject, e.g., a human patient suffering from (or at risk of developing) a cancer, e.g., using standard methods.

Therapeutic formulations of the disclosure, which include a conjugate of the disclosure that recognizes CD19 and, optionally, a second target can be used to treat or alleviate a symptom associated with an autoimmune disease and/or inflammatory disease, such as, for example, B-cell mediated autoimmune diseases and/or inflammatory diseases, including by way of non-limiting example, systemic lupus erythematosus (SLE), rheumatoid arthritis (RA), idiopathic thrombocytopenic purpura (ITP), Waldenstrom's hypergammaglobulinaemia, Sjogren's syndrome, multiple sclerosis (MS), and/or lupus nephritis.

Efficaciousness of treatment can be determined in association with any suitable method for diagnosing or treating the particular immune-related disorder. Alleviation of one or more symptoms of the immune-related disorder indicates that the conjugate confers a clinical benefit.

Conjugates directed against a target such as CD19, a tumor associated antigen or other antigen may be used in methods relating to the localization and/or quantitation of these targets, e.g., for use in measuring levels of these targets within appropriate physiological samples, for use in diagnostic methods, for use in imaging the protein, and the like). For example, conjugates specific for any of these targets, or derivative, fragment, analog or homolog thereof, that contain the antibody derived antigen-binding domain, can be utilized as pharmacologically active compounds (referred to hereinafter as "Therapeutics").

A conjugate of the disclosure can be used to isolate a particular target using standard techniques, such as immunoaffinity, chromatography or immunoprecipitation. Conjugates of the disclosure can be used diagnostically to monitor protein levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Conjugates of the disclosure may be used as therapeutic agents. Such agents will generally be employed to treat or prevent a disease or pathology associated with aberrant expression or activation of a given target in a subject. A conjugate preparation, preferably one having high specificity and high affinity for its target antigen, is administered to the subject and will generally have an effect due to its binding with the target. Administration of the conjugate may abrogate or inhibit or interfere with the signaling function of the target. Administration of the conjugate may abrogate or inhibit or interfere with the binding of the target with an endogenous ligand to which it naturally binds.

A therapeutically effective amount of a conjugate of the disclosure relates generally to the amount needed to achieve a therapeutic objective. As noted above, this may be a binding interaction between the antibody and its target antigen that, in certain cases, interferes with the functioning of the target and/or the effect of an active agent conjugated to the antibody. The amount required to be administered will furthermore depend on the binding affinity of the antibody for its specific antigen and/or the potency of the active agent, and will also depend on the rate at which an administered antibody is depleted from the free volume other subject to which it is administered. Common ranges for therapeutically effective dosing of a conjugate of the disclosure may be, by way of nonlimiting example, from about 0.1 mg/kg body weight to about 50 mg/kg body weight. Common dosing frequencies may range, for example, from twice daily to once a week.

Conjugates of the disclosure can be administered for the treatment of a variety of diseases and disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement:

Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration are preferably sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, nondegradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

A conjugate according to the disclosure can be used as an agent for detecting the presence of a given target (or a protein fragment thereof) in a sample. In some embodiments, the conjugate contains a detectable label. Antibodies can be polyclonal, or more preferably, monoclonal. An intact antibody, or a fragment thereof (e.g., $F_{ab}$, scFv, or $F_{(ab)2}$) can be used. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte conjugate. For example, the antibody can be labeled with a radioactive marker whose presence and location in a subject can be detected by standard imaging techniques.

Pharmaceutical Compositions

The antibody-drug conjugate may be used to transfer the active agent to a target cell of a subject to treat the subject using any suitable method of preparing a composition. In some aspects, the disclosure relates to a composition (e.g., a pharmaceutical composition) comprising an antibody-drug conjugate as described herein.

The compositions and methods of the present disclosure may be utilized to treat an individual in need thereof. In certain embodiments, the individual is a mammal such as a human, or a non-human mammal. When administered to an animal, such as a human, the composition or the compound is preferably administered as a pharmaceutical composition comprising, for example, a compound of the disclosure and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent or to selectively target one or more cells, tissues or organs. The pharmaceutical composition can be in dosage unit form such as tablet, capsule (including sprinkle capsule and gelatin capsule), granule, lyophile for reconstitution, powder, solution, syrup, suppository, injection or the like. The composition can also be present in a transdermal delivery system, e.g., a skin patch. The composition can also be present in a solution suitable for topical administration, such as a lotion, cream, or ointment.

A pharmaceutically acceptable carrier can contain physiologically acceptable agents that act, for example, to stabilize, increase solubility or to increase the absorption of a compound such as a compound of the disclosure. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition. The preparation or pharmaceutical composition can be a selfemulsifying drug delivery system or a selfmicroemulsifying drug delivery system. The pharmaceutical composition (preparation) also can be a liposome or other polymer matrix, which can have incorporated therein, for example, a compound of the disclosure. Liposomes, for example, which comprise phospholipids or other lipids, are nontoxic, physiologically acceptable and metabolizable carriers that are relatively simple to make and administer.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A pharmaceutical composition (preparation) can be administered to a subject by any of a number of routes of administration including, for example, orally (for example, drenches as in aqueous or non-aqueous solutions or suspensions, tablets, capsules (including sprinkle capsules and gelatin capsules), boluses, powders, granules, pastes for application to the tongue); absorption through the oral mucosa (e.g., sublingually); subcutaneously; transdermally (for example as a patch applied to the skin); and topically (for example, as a cream, ointment or spray applied to the skin). The compound may also be formulated for inhalation. In certain embodiments, a compound may be simply dissolved or suspended in sterile water. Details of appropriate routes of administration and compositions suitable for same can be found in, for example, U.S. Pat. Nos. 6,110,973, 5,763,493, 5,731,000, 5,541,231, 5,427,798, 5,358,970 and 4,172,896, as well as in patents cited therein.

The formulations may conveniently be presented in unit dosage form and may be prepared by any suitable method in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an active compound, such as a compound of the disclosure, with the carrier and, optionally, one or more accessory ingredients. In general, the formulations are prepared by uniformly and intimately bringing into association a compound of the present disclosure with liquid carriers, or finely divided solid carriers, or both, and then, if necessary, shaping the product.

Formulations of the disclosure suitable for oral administration may be in the form of capsules (including sprinkle capsules and gelatin capsules), cachets, pills, tablets, lozenges (using a flavored basis, usually sucrose and acacia or tragacanth), lyophile, powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present disclosure as an active ingredient. Compositions or compounds may also be administered as a bolus, electuary or paste.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; (10) complexing agents, such as, modified and unmodified cyclodextrins; and (11) coloring agents. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions, such as dragees, capsules (including sprinkle capsules and gelatin capsules), pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions that can be used include polymeric substances and waxes. The active ingredient can also be in microencapsulated form, if appropriate, with one or more of the above-described excipients.

Liquid dosage forms useful for oral administration include pharmaceutically acceptable emulsions, lyophiles for reconstitution, microemulsions, solutions, suspensions, syrups and elixirs. In addition to the active ingredient, the liquid dosage forms may contain inert diluents commonly used in the art, such as, for example, water or other solvents, cyclodextrins and derivatives thereof, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Dosage forms for the topical or transdermal administration include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present disclosure to the body. Such dosage forms can be made by dissolving or dispersing the active compound in the proper medium. Absorption enhancers can also be used to increase the flux of the compound across the skin. The rate of such flux can be controlled by either providing a rate controlling membrane or dispersing the compound in a polymer matrix or gel.

The phrases "parenteral administration" and "administered parenterally" as used herein means modes of administration other than enteral and topical administration, usually by injection, and includes, without limitation, intravenous, intraocular (such as intravitreal), intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion. Pharmaceutical compositions suitable for parenteral administration comprise one or more active compounds in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the disclosure include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsulated matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

For use in the methods of this disclosure, active compounds can be given per se or as a pharmaceutical composition containing, for example, 0.1 to 99.5% (more preferably, 0.5 to 90%) of active ingredient in combination with a pharmaceutically acceptable carrier.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a compound at a particular target site.

Actual dosage levels of the active ingredients in the pharmaceutical compositions may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the patient being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the patient's condition, the disorder being treated, the stability of the compound, and, if desired, another type of therapeutic agent being administered with the compound of the disclosure. A larger total dose can be delivered by multiple administrations of the agent. Many methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the disclosure will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present disclosure, the active compound may be administered two or three times daily. In preferred embodiments, the active compound will be administered once daily.

The patient receiving this treatment is any animal in need, including primates, in particular humans; and other mammals such as equines, cattle, swine, sheep, cats, and dogs; poultry; and pets in general.

In certain embodiments, compounds of the disclosure may be used alone or conjointly administered with another type of therapeutic agent.

The present disclosure includes the use of pharmaceutically acceptable salts of compounds of the disclosure in the compositions and methods of the present disclosure. In certain embodiments, contemplated salts of the disclosure include, but are not limited to, alkyl, dialkyl, trialkyl or tetra-alkyl ammonium salts. In certain embodiments, contemplated salts of the disclosure include, but are not limited to, L-arginine, benenthamine, benzathine, betaine, calcium hydroxide, choline, deanol, diethanolamine, diethylamine, 2-(diethylamino)ethanol, ethanolamine, ethylenediamine, N-methylglucamine, hydrabamine, 1H-imidazole, lithium, L-lysine, magnesium, 4-(2-hydroxyethyl)morpholine, piperazine, potassium, 1-(2-hydroxyethyl)pyrrolidine, sodium, triethanolamine, tromethamine, and zinc salts. In certain embodiments, contemplated salts of the disclosure include, but are not limited to, Na, Ca, K, Mg, Zn or other metal salts. In certain embodiments, contemplated salts of the disclosure include, but are not limited to, 1-hydroxy-2-naphthoic acid, 2,2-dichloroacetic acid, 2-hydroxyethanesulfonic acid, 2-oxoglutaric acid, 4-acetamidobenzoic acid, 4-aminosalicylic acid, acetic acid, adipic acid, 1-ascorbic acid, 1-aspartic acid, benzenesulfonic acid, benzoic acid, (+)-camphoric acid, (+)-camphor-10-sulfonic acid, capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethanesulfonic acid, formic acid, fumaric acid, galactaric acid, gentisic acid, d-glucoheptonic acid, d-gluconic acid, d-glucuronic acid, glutamic acid, glutaric acid, glycerophosphoric acid, glycolic acid, hippuric acid, hydrobromic acid, hydrochloric acid, isobutyric acid, lactic acid, lactobionic acid, lauric acid, maleic acid, 1-malic acid, malonic acid, mandelic acid, methanesulfonic acid, naphthalene-1,5-disulfonic acid, naphthalene-2-sulfonic acid, nicotinic acid, nitric acid, oleic acid, oxalic acid, palmitic acid, pamoic acid, phosphoric acid, proprionic acid, 1-pyroglutamic acid, salicylic acid, sebacic acid, stearic acid, succinic acid, sulfuric acid, 1-tartaric acid, thiocyanic acid, p-toluenesulfonic acid, trifluoroacetic acid, and undecylenic acid salts.

The pharmaceutically acceptable acid addition salts can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water-soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal-chelating agents, such as citric acid, ethylenediamine tetraacetic acid (EDTA), sorbitol, tartaric acid, phosphoric acid, and the like.

Compositions may be prepared in an injectable form, either as a liquid solution or as a suspension. Solid forms suitable for injection may also be prepared, e.g., as emulsions, or with the antibody-drug conjugate encapsulated in liposomes. Antibody-drug conjugates may be combined with a pharmaceutically acceptable carrier, which includes any carrier that does not induce the production of antibodies harmful to the subject receiving the carrier. Suitable carriers typically comprise large macromolecules that are slowly metabolized, for example, proteins, polysaccharides, polylactic acids, polyglycolic acids, polymeric amino acids, amino acid copolymers, lipid aggregates, and the like.

The compositions may also contain diluents, for example, water, saline, glycerol, and ethanol. Auxiliary substances, for example, wetting or emulsifying agents, pH buffering substances, and the like may also be present therein. The compositions may be parenterally administered by injection, wherein such injection may be either subcutaneous or intramuscular injection. In some embodiments, a composition may be administered into a tumor. The composition may be inserted (e.g., injected) into a tumor. Additional formulations are suitable for other forms of administration, such as suppository or oral administration. Oral compositions may be administered as a solution, suspension, tablet, pill, capsule, or sustained release formulation.

The compositions may be administered in a manner compatible with a dose and a formulation. The composition preferably comprises a therapeutically effective amount of the antibody-drug conjugate. A dose may vary, depending on the subject to be treated, the subject's health and physical conditions, a degree of protection to be desired, and other relevant factors. The exact amount of an active ingredient (e.g., the antibody-drug conjugate) may depend on the judgment of a doctor. For example, a therapeutically effective amount of the antibody-drug conjugate or composition containing the same may be administered to a patient suffering from a cancer or tumor to treat the cancer or tumor.

The antibody-drug conjugate according to the present disclosure or the composition containing the same may be administered in the form of a pharmaceutically acceptable salt or solvate thereof. In some embodiments, the antibody-drug conjugate according to the present disclosure or the composition containing the same may be administered with a pharmaceutically acceptable carrier, a pharmaceutically acceptable excipient, and/or a pharmaceutically acceptable additive. The effective amount and the type of the pharmaceutically acceptable salt or solvate, excipient and additive may be measured using standard methods (see, e.g., Remington's Pharmaceutical Sciences, Mack Publishing Co., Easton, Pa., 18th Edition, 1990).

Exemplary solvates that may be used for pharmaceutically acceptable solvates of the antibody-drug conjugates described herein include water, isopropanol, ethanol, methanol, dimethyl sulfoxide, ethyl acetate, acetic acid, and ethanolamine.

Exemplary solvates that may be used for pharmaceutically acceptable solvates of the antibody-drug conjugates described herein include water, isopropanol, ethanol, methanol, dimethyl sulfoxide, ethyl acetate, acetic acid, and ethanol amine.

In some embodiments, the disclosure relates to a method of treating cancer in a subject, comprising administering a pharmaceutical composition comprising an antibody-drug conjugate as described herein to the subject. In preferred embodiments, the subject is a mammal. For example, the subject may be selected from rodents, lagomorphs, felines, canines, porcines, ovines, bovines, equines, and primates. In certain preferred embodiments, the subject is a human.

The conjugates of the disclosure (also referred to herein as "active compounds"), and derivatives, fragments, analogs and homologs thereof, can be incorporated into pharmaceutical compositions suitable for administration. Such compositions typically comprise the conjugate and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds can be formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to suitable methods, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

All of the above, and any other publications, patents and published patent applications referred to in this application are specifically incorporated by reference herein. In case of conflict, the present specification, including its specific definitions, will control.

The disclosure will be further described in the following examples, which do not limit the scope of the disclosure described in the claims.

Hereinafter, configurations of the present disclosure will be described in detail through Examples, but the following Examples are only to assist in understanding of the present disclosure. The scope of the present disclosure is not limited thereto. Further, unless specifically described otherwise, the reagent, solvent, and starting material described in the specification can be easily obtained from a commercial supplier.

EXEMPLIFICATION

The table below lists the abbreviations used throughout the following Examples:

| Abbreviation | Reference |
|---|---|
| Ac | acetyl |
| AcOH | acetic acid |
| aq. | aqueous |
| Bn | benzyl |
| brine | saturated aqueous sodium chloride solution |
| Boc | t-butoxycarbonyl |
| Cbz | benzyloxycarbonyl |
| DBU | 1,8-diazabicyclo[5.4.0]undec-7-ene |
| DCM | dichloromethane |
| DIC | N,N'-diisopropylcarbodiimide |
| DIPEA | N,N-diisopropylethylamine |
| DMAP | 4-(dimethylamino)pyridine |
| DMF | N,N-dimethylformamide |
| DMSO | dimethyl sulfoxide |
| EDC | N-(3-dimethylaminopropyl)-N'-ethylcarbodiimide |
| Et | ethyl |
| Et2O | diethyl ether |
| EtOAc | ethyl acetate |
| EtOH | ethanol |
| HBTU | O-(benzotriazol-1-yl)-N,N,N',N'-tetramethyluronium hexafluorophosphate |
| Hex | n-hexane |
| HOBt | 1-hydroxybenzotriazole |
| HPLC | high performance liquid chromatography |
| Me | Methyl |
| MeCN | acetonitrile |
| MeOH | methanol |
| MMAE | monomethyl auristatin E |
| MMAF | monomethyl auristatin F |
| MMAF-OMe | monomethyl auristatin F methyl ester |
| i-PrOH | isopropanol |
| PyBOP | (benzotriazol-1-yloxy)tripyrrolidinophosphonium hexafluorophosphate |
| TBAF | tetrabutylammonium fluoride |
| TBS | t-butyldimethylsilyl |
| THF | tetrahydrofuran |
| TFA | trifluoroacetic acid |
| Ts | p-toluenesulfonyl |
| wt | weight |

EXAMPLES

Example 1: Synthesis of Antibody-Drug Conjugates

Example 2: The Antibody-Drug Conjugates Disclosed Herein May be Prepared by any Suitable Method, Including Those Known in the Art. For Example See: i) WO 2018/182341, which Describes the Preparation of Pyrrolobenzodiazepine Dimers and Antibody-Drug Conjugates Therefore; ii) WO 2015/182984, which Describes the Preparation of Antibody-Drug Conjugates Comprising Glucuronic Acid Moieties; and iii) WO 2018/083535, which Describes the Preparation of Certain Anti-CD-19 Antibodies. The Contents of Each of the Aforementioned Publications are Hereby Incorporated by Reference in their Entries. Lymphocyte Binding Analysis of Anti-CD19 Antibodies The ability of various anti-CD19 antibodies of the disclosure to bind various human B lymphocyte cell lines was evaluated. In particular, the human IgG1 5F5, 7F11, 9G8, F6, 7F1, and 10D8 anti-CD19 antibodies were evaluated for their abilities to bind (i) six human B lymphocyte cell lines:

Raji, Ramos, Nalm6, Su-DHL6, Su-DHL4, and Mec2, (ii) a CD19 silenced B cell line: Raji siRNA; and a negative cell line (Jurkat). All incubations were prepared in FACS buffer (PBS, BSA 2%) at 4° C. Fc receptors on B cells were blocked with 10% mouse serum. Four doses of hIgG1 were tested: 10, 1, 0.1 and 0.01 µg/mL. Cell surface bound hIgG1 were detected with a mouse anti-human IgG Fc-PE mAb. The results of this study are shown in FIGS. 1A-1F.

As shown in FIGS. 1A-1F, all of the tested anti-CD19 antibodies bind to all of the six different B lymphocytes, although with different profiles and/or different affinities. For example, 7F1 and 10D8 bind better to Nalm6 than to Raji cells, whereas the other antibodies show the opposite binding profile. All the tested antibodies are clearly specific for CD19, and all of the tested antibodies lose the ability to bind CD19 in the CD19-silenced cell line Raji siRNA. None of the cell lines bound to the negative cell line.

Example 3: Cross-Reactivity Analysis of Anti-CD19 Antibodies

The ability of the anti-CD19 antibodies to bind human and/or cynomolgus monkey CD19 was evaluated.

Figure 2:
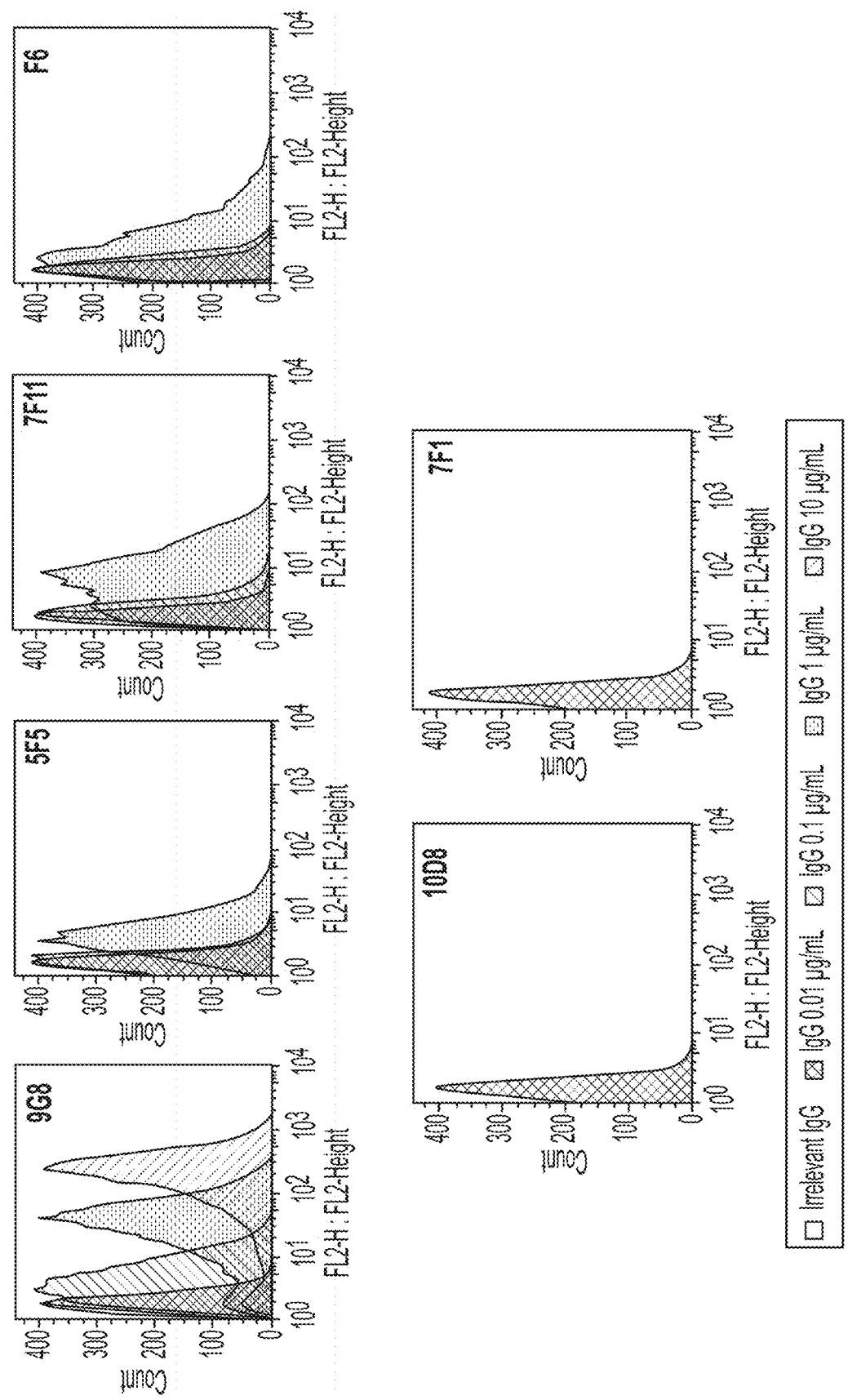
FIG. 2 is a series of graphs depicting the ability of various anti-CD19 antibodies of the disclosure to bind cynomolgus CD19 expressed by transfected CHO cells or a negative control cell line (CHO) as determined by FACS analysis.

In particular, the human IgG1 5F5, 7F11, 9G8, F6, 7F1, and 10D8 anti-CD19 antibodies were evaluated for their abilities to bind a CHO cell line transfected with cynomolgus CD19 and a negative control cell line (CHO). All incubations were prepared in FACS buffer (PBS, BSA 2%) at 4° C. Fc receptors on B cells were blocked with 10% mouse serum. Four doses of hIgG1 were tested: 10, 1, 0.1 and 0.01 µg/mL. The results of this study are shown in FIG. 2.

The 9G8 anti-CD19 antibody is clearly cross-reactive with cynomolgus CD19. The anti-CD19 antibodies 5F5, 7F11, and F6 are also slightly cross-reactive with cynomolgus as seen on the FACS overlays in FIG. 2. The anti-CD19 antibodies 7F1 and 10D8 did not bind to the transfected CHO cynoCD19 cells.

Example 4: Peripheral Blood Mononuclear Cell (PBMC) Binding Analysis of Anti-CD19 Antibodies The ability of various anti-CD19 antibodies of the disclosure to bind various peripheral blood mononuclear cells (PBMC). Human and cynomolgus PBMC from frozen aliquots in citrate buffer were tested. Two doses of the following human IgG1 anti-CD19 antibodies were tested at 30 µg/mL and 3 µg/mL: 5F5, 7F11, 9G8, F6, 10D8, 7F1, Mdx as positive control, and an anti-IP-10 antibody referred to as NI-0801 as negative control. The PBMC were labelled with anti-CD20-PE monoclonal antibody (mAb), anti-CD14-FITC mAb, and anti-CD3-PerCP mAb cross-reactive both to human and cynomolgus species. Cell surface bound hIgG1 were detected with a mouse anti-human IgG Fc-APC mAb. FACS gating was performed with the anti-CD20 mAb for the B lymphocyte population, with the anti-CD3 for the T lymphocyte population and with anti-CD14 for the monocyte population. The results of these studies are shown in FIG. 3A-3F.

Figure 3A:
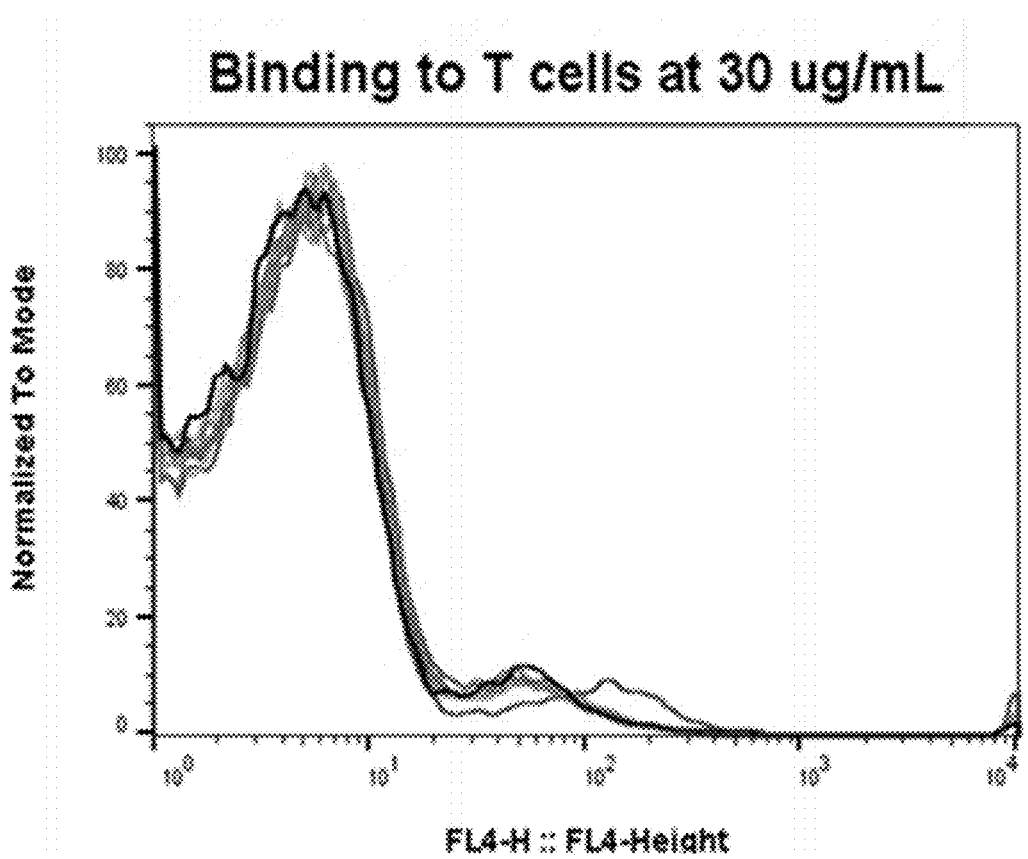
FIG. 3A shows graphs depicting the ability of various anti-CD19 antibodies of the disclosure at a concentration of 30 ug/mL or 3 ug/mL to bind to human T cells and monocytes.
Figure 3A:
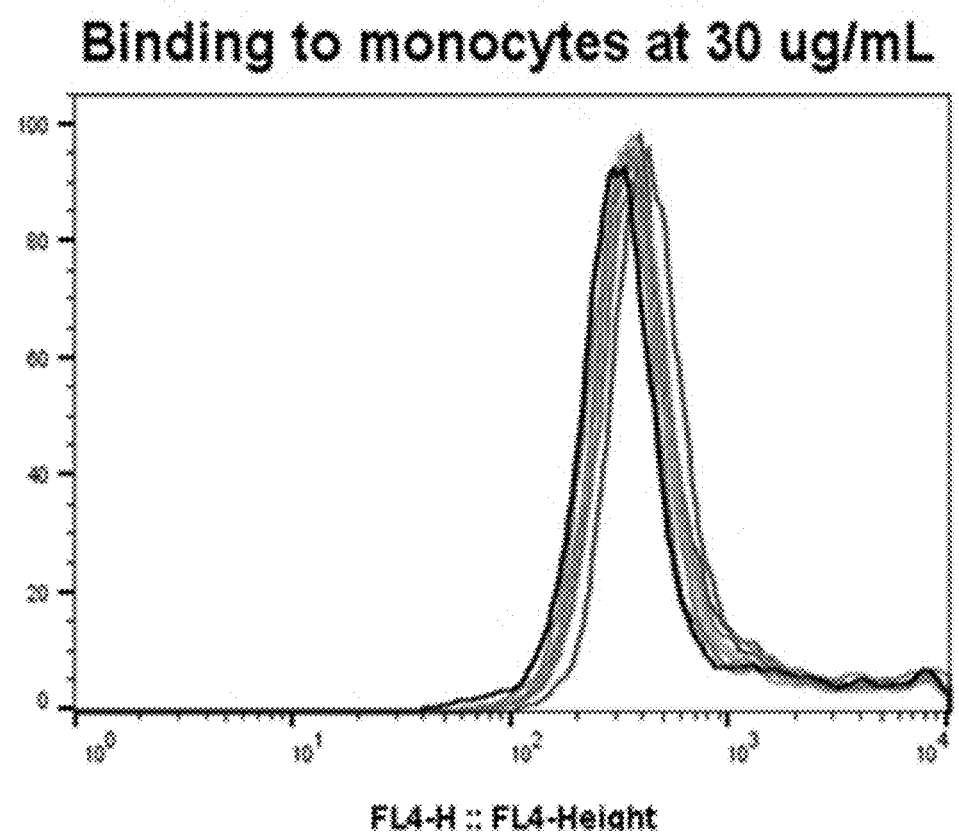
Figure 3B:
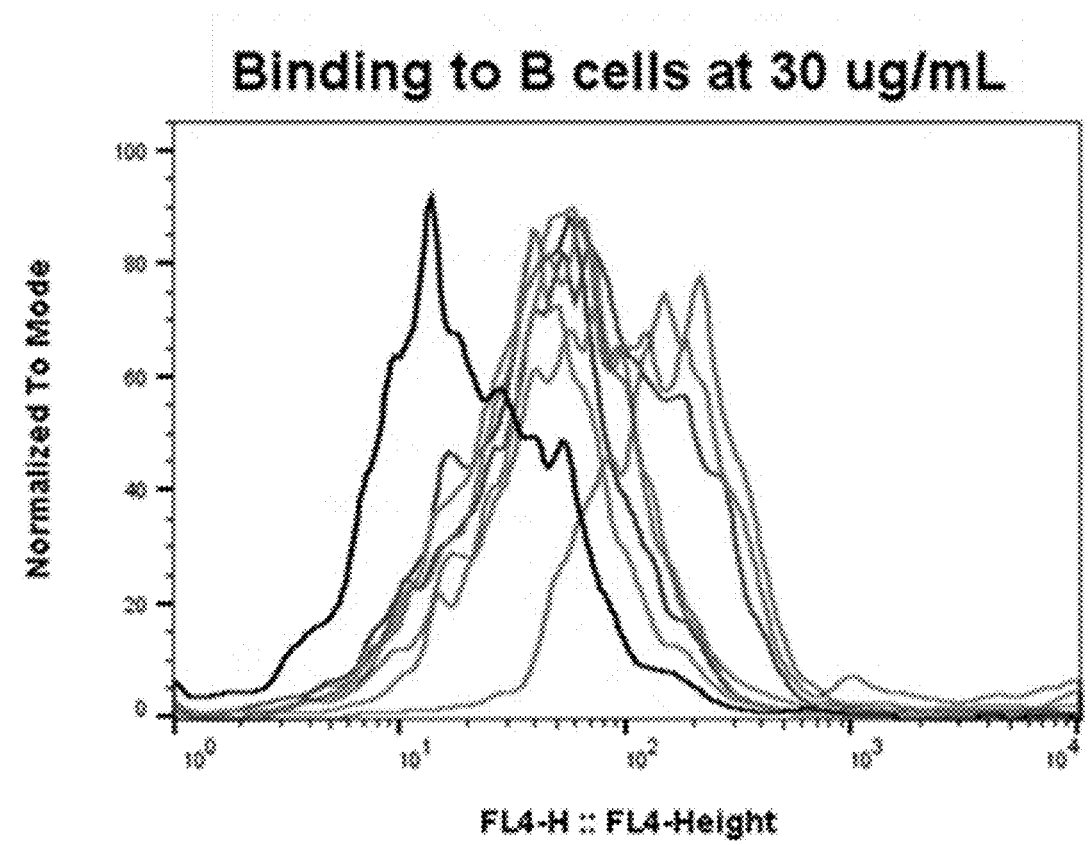
FIG. 3B shows graphs depicting the ability of various anti-CD19 antibodies of the disclosure at a concentration of 30 ug/mL or 3 ug/mL to bind to cynomolgus B cells.
Figure 3B:
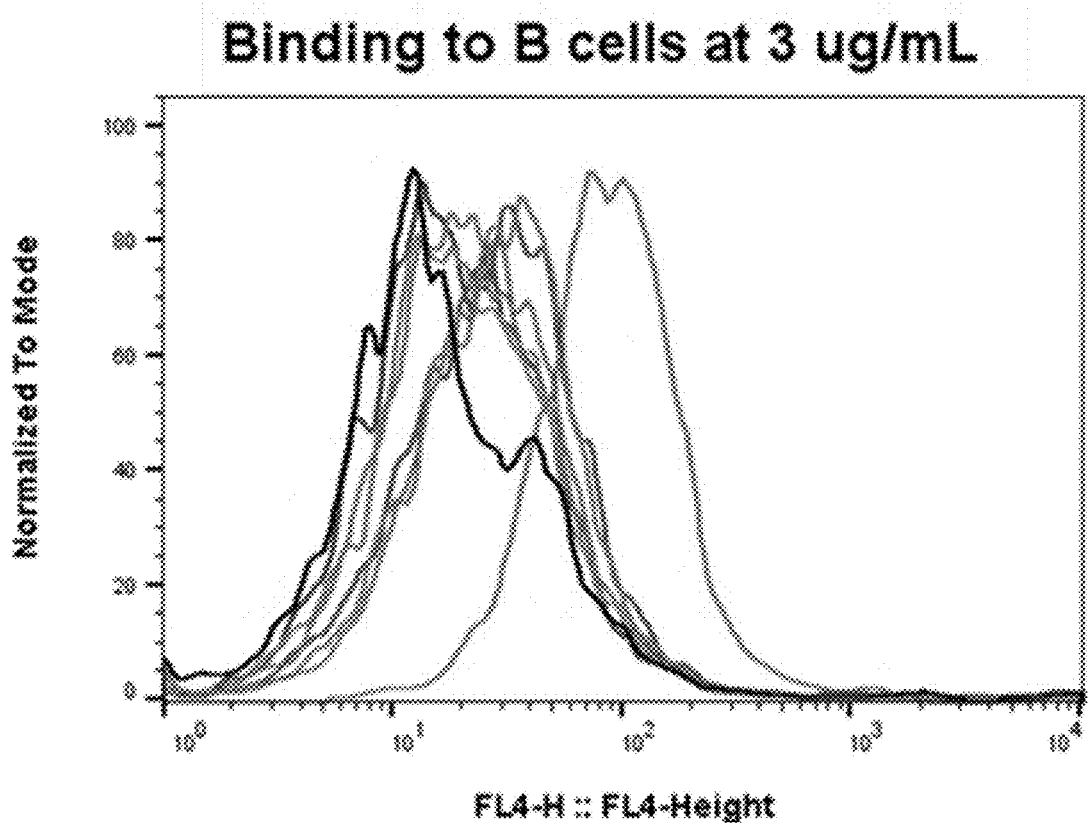
Figure 3C:
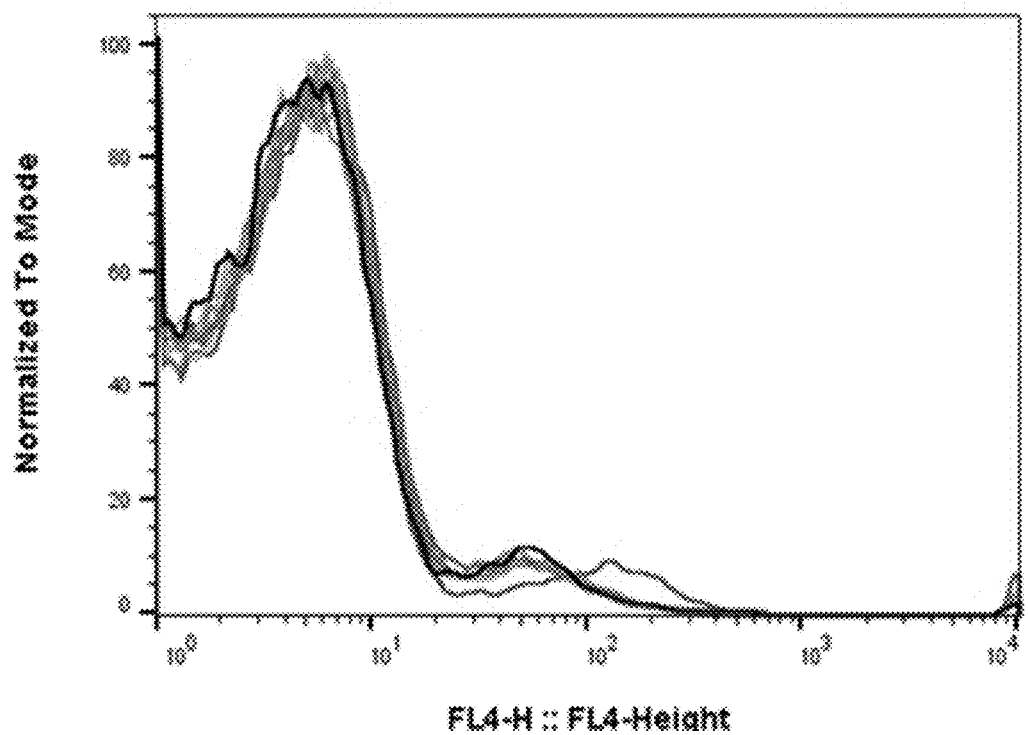
FIG. 3C shows graphs depicting the ability of various anti-CD19 antibodies of the disclosure at a concentration of 30 ug/mL or 3 ug/mL to bind to human T cells and monocytes.
Figure 3C:
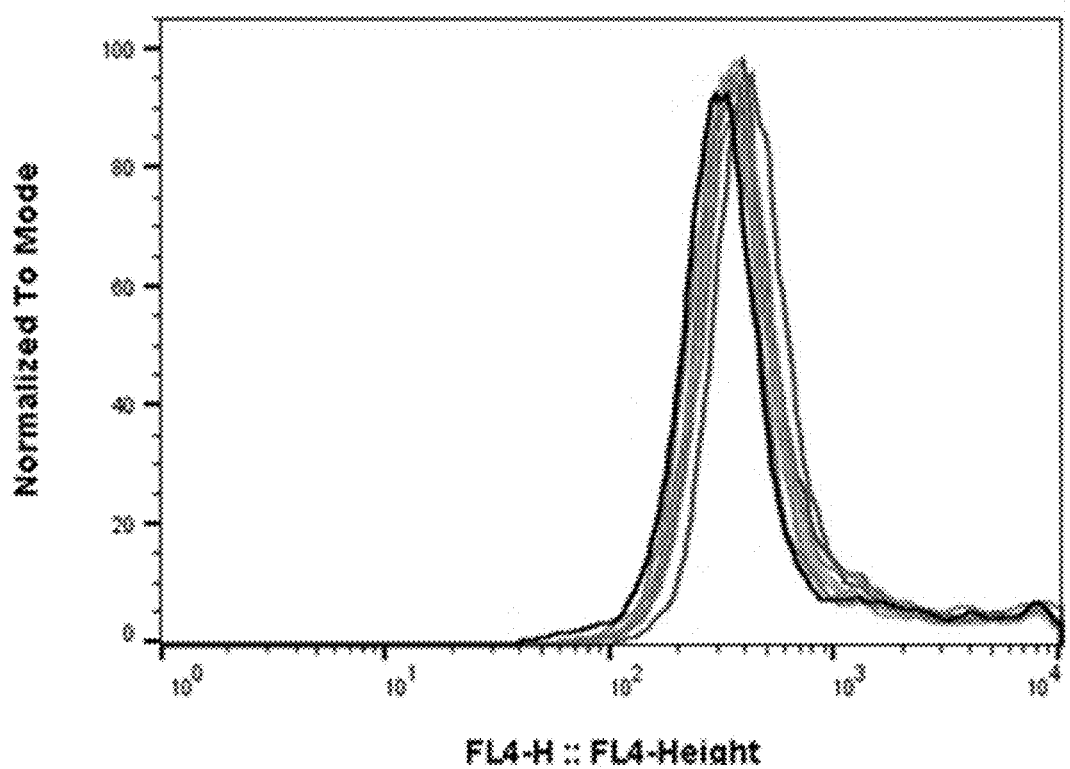
Figure 4A:
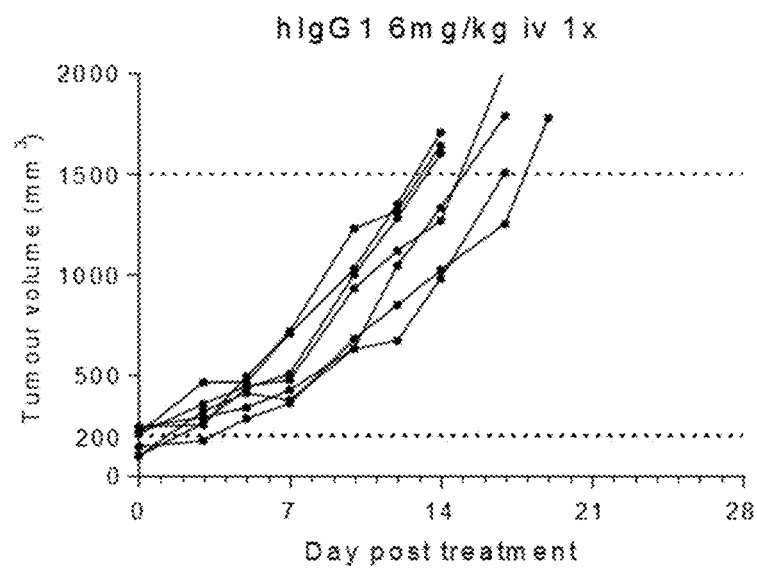
FIGS. 4A-4G show tumor volume over time in CB17-SCID mice who were implanted with Ramos cells and then treated with 9G8 anti-CD19 ADC, non-tumor specific human IgG1 anti-HER2-ADC or rituximab. Mice who were treated with the 9G8 anti-CD19 ADC exhibited regression of tumor growth.
Figure 4B:
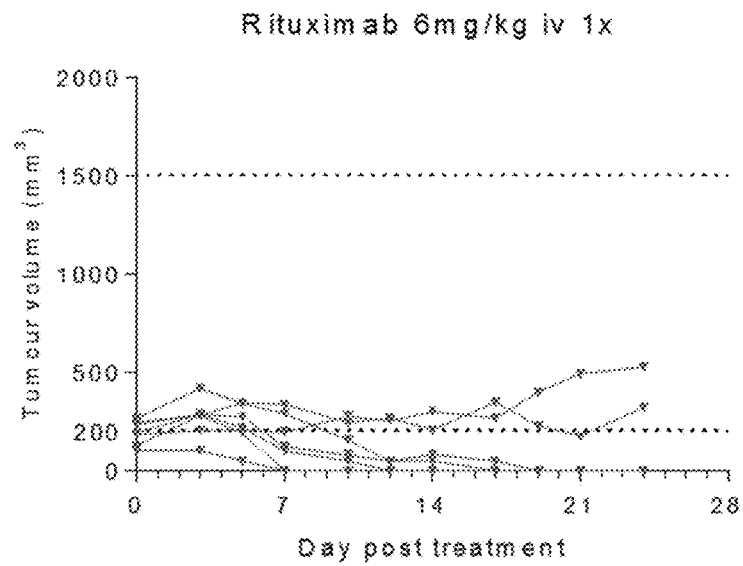
Figure 4C:
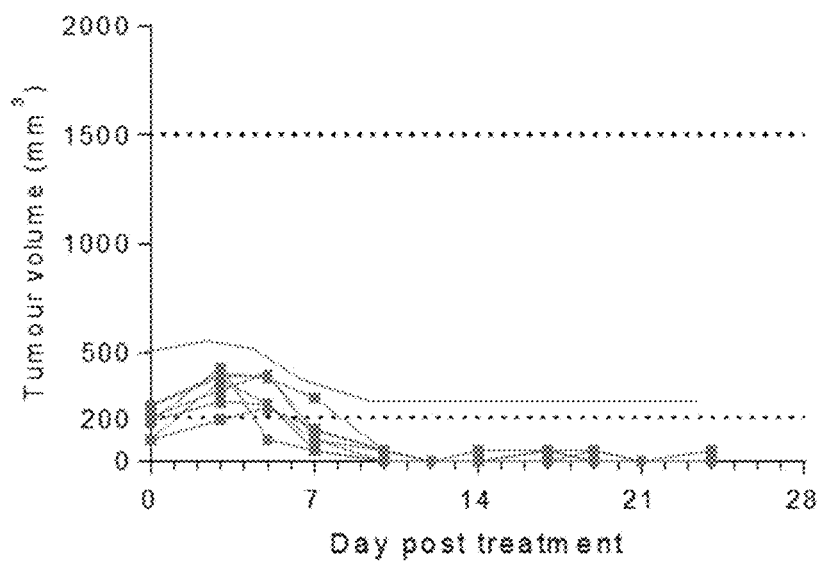
Figure 4D:
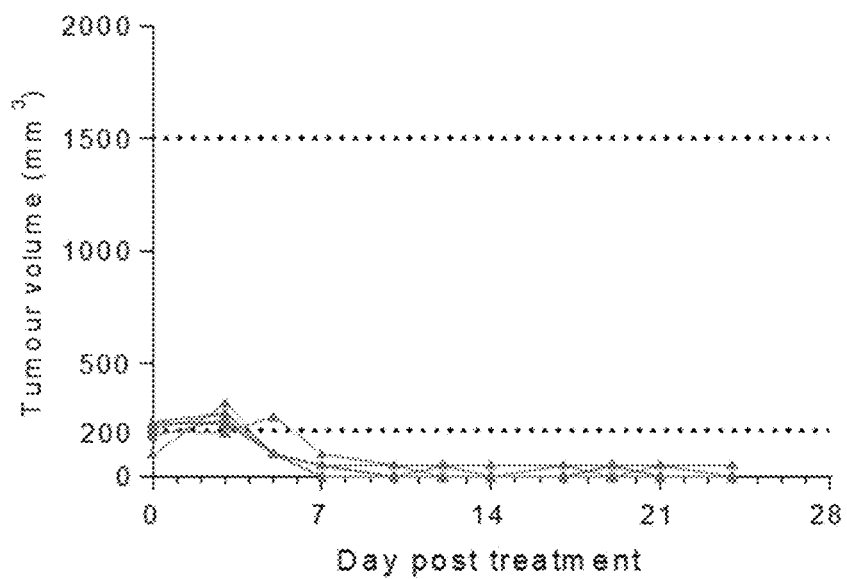
Figure 4E:
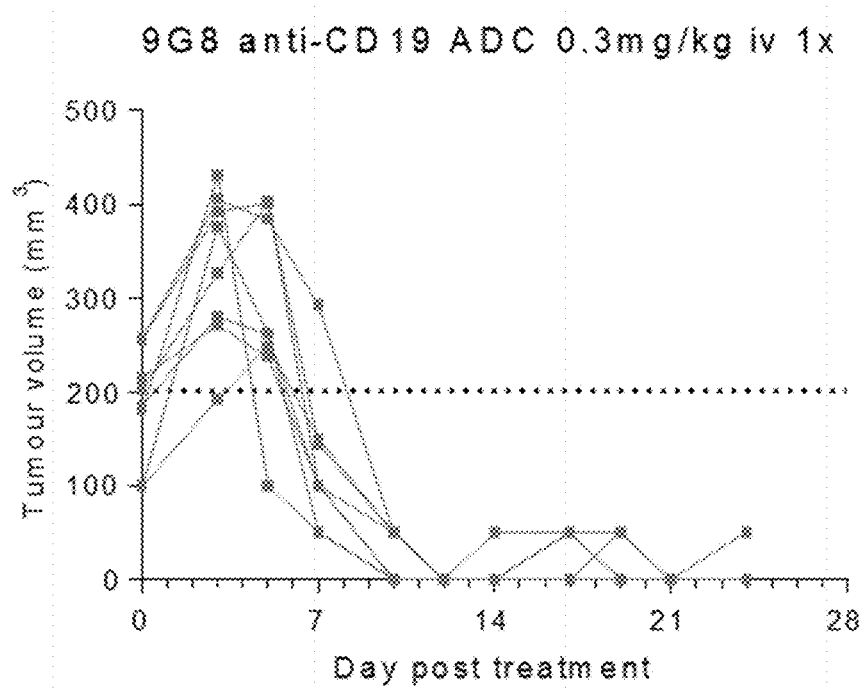
Figure 4F:
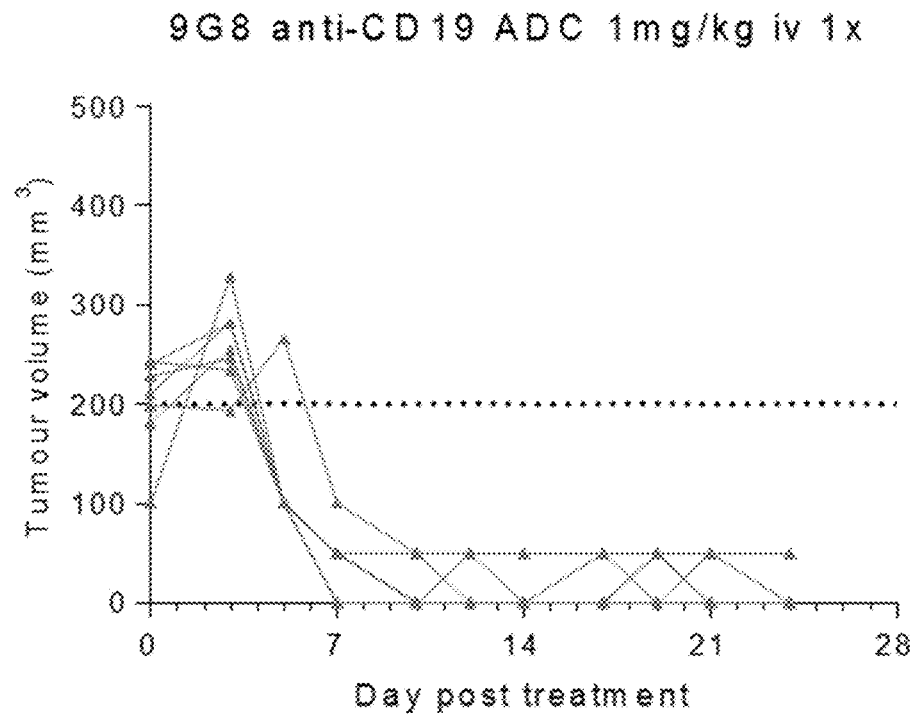
Figure 4G:
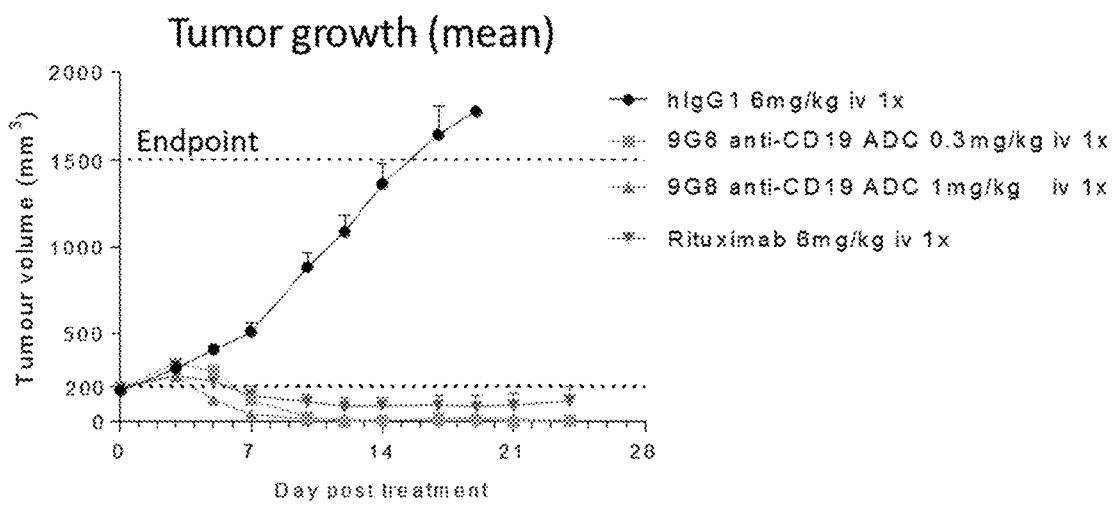
Figure 4H:
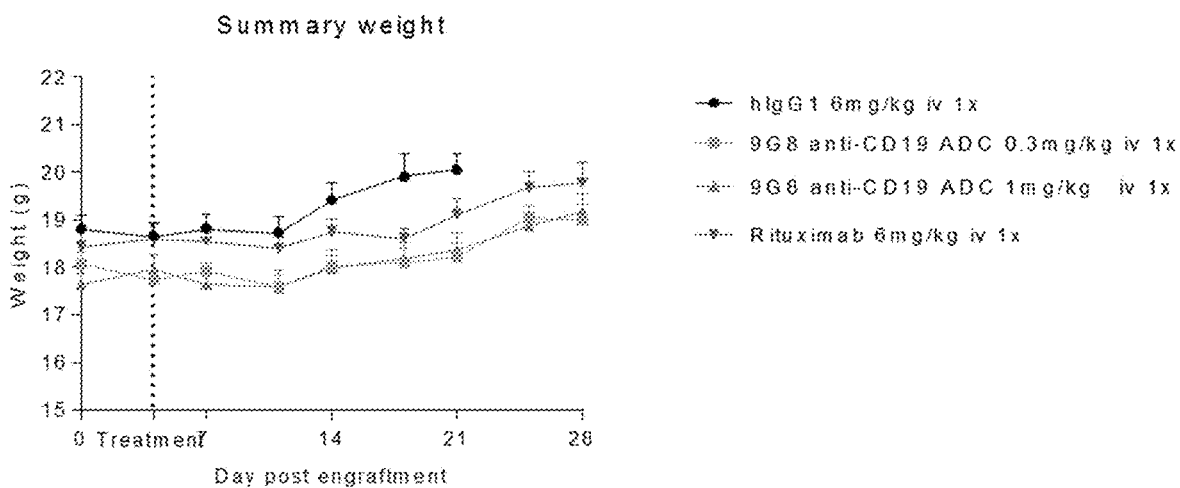
FIG. 4H shows the mean weight over time of CB17-SCID mice who were implanted with Ramos cells and then treated with human IgG1 isotype, 9G8 anti-CD19 ADC, non-tumor specific human IgG1 anti-HER2-ADC or rituximab.

As shown in FIG. 3C, none of the tested anti-CD19 antibodies bound to human PBMC CD3+ at a high dose of 30 µg/mL. All of the tested antibodies demonstrated the same binding level on monocytes as seen with the negative control NI-0801, binding due to cell surface Fc receptors. As shown in FIG. 3A, all of the tested anti-CD19 antibodies bound to human PBMC CD20+, small affinity differences can be seen at 3 µg/mL. FIG. 3C demonstrate the cross-reactivity of all the anti-CD19 antibodies. The binding is up to ten-fold higher on human than on cynomolgus PBMC, which is in the same range as seen for the positive control Mdx.

Example 5: Exemplary Xenograft Study with Anti-CD19 Antibody 9G8

Antitumor Efficacy of Anti-CD19 ADC (9G8) in Raji Non-Hodgkin Lymphoma Xenograft Model Anti-tumor activity of anti-CD19 (9G8) Antibody Drug Conjugate was evaluated in immunodeficient CB17SCID mice subcutaneously engrafted with Raji Burkitt's lymphoma cells.

CB17-SCID mice (Charles River), aged 7 weeks, were implanted subcutaneously (s.c.) in the right flank with $5 \times 10^6$ Raji cells (obtained from ATCC). Tumor volumes (calculated using the formula TV=($0.5 \times [\text{length} \times \text{width}^2]$)) were measured by digital caliper 4 days after implantation, and mice were assigned to different groups (see table below) in order to obtain homogeneous mean tumor volume between cohorts (n=7-8 mice per group. Mean tumor volume at D4: hIgG1 control 6 mg/kg: 180 mm³±63; anti CD19 ADC 0.3 mg/kg: 187 mm³±61; anti CD19 ADC 1 mg/kg: 200 mm³±49; rituximab 6 mg/kg: 194 mm³±63). The same day, mice were treated i.v. in the tail vein with a single dose of hIgG1 control (6 mg/kg), anti-CD19 ADC at 0.3 or 1 mg/kg or rituximab (6 mg/kg). Mice were then monitored for body weight 2 times a week and for tumor growth 3 times a week until the endpoint of the experiment (tumor volume=1500 mm³). Animal facility and experiments were approved by the animal research committee of Geneva canton and experiments were performed in accordance with the Swiss Federal Veterinary Office guidelines. Mice who were treated with the 9G8 anti-CD19 ADC exhibited regression of tumor growth (FIGS. 4A-4H).

Antitumor Efficacy of Anti-CD19 ADC (9G8) in Ramos Non-Hodgkin Lymphoma Xenograft Model Anti-tumor activity of anti-CD19 (9G8) Antibody Drug Conjugate was evaluated in immunodeficient CB-17 scid mice subcutaneously engrafted with Ramos Burkitt's lymphoma cells.

CB17-SCID mice (Charles River), aged 7 weeks, were implanted subcutaneously (s.c.) in the right flank with $5 \times 10^6$ Ramos cells (obtained from ATCC). Tumor volumes (calculated using the formula TV=($0.5 \times [\text{length} \times \text{width}^2]$)) were measured by digital caliper 3 times a week and mice were recruited for treatment when tumor volumes reached 200-250 mm³. Mice were assigned to different groups (see table below) in order to obtain homogeneous mean tumor volumes between cohorts (n=7-8 mice per group. Mean tumor volume: hIgG1 control 1 mg/kg, 1 inj.: 243 mm³±26; anti-CD19 CaaX 1 mg/kg, 1 inj.: 233 mm³±18; hIgG1 ADC 1 mg/kg, 1 inj.: 224 mm³±20; anti CD19 ADC 0.33 mg/kg, 1 inj.: 242 mm³±28; anti CD19 ADC 0.66 mg/kg, 1 inj.: 234 mm³±23; anti CD19 ADC 1 mg/kg, 1 inj.: 234 mm³±31; anti CD19 ADC 0.33 mg/kg 1 inj./week during 3 weeks: 251 mm³±25; rituximab 6 mg/kg, 1 inj.: 242 mm³±31). Single dose or multiple dose (only for cohort anti-CD19 ADC 0.33 mg/kg 1×/week, 3 weeks) treatments were injected i.v. in the tail vein. Mice were then monitored for body weight 3 times a week and for tumor growth 3 times a week until the endpoint of the experiment (tumor volume=1500 mm³). Animal facility and experiments were approved by the animal research committee of Geneva canton and experiments were performed in accordance with the Swiss Federal Veterinary Office guidelines.

| Group | Treatment | N | Dose | Injection frequency |
|---|---|---|---|---|
| 1 | human IgG1 isotype control | 8 | 1 mg/kg | single |
| 2 | 9G8 anti-CD19 CaaX body | 8 | 1 mg/kg | single |
| 3 | non-tumor specific human IgG1 anti-HER2-ADC | 8 | 1 mg/kg | single |
| 4 | 9G8 anti-CD19 ADC | 8 | 1 mg/kg | single |
| 5 | 9G8 anti-CD19 ADC | 8 | 0.66 mg/kg | single |
| 6 | 9G8 anti-CD19 ADC | 8 | 0.33 mg/kg | single |
| 7 | 9G8 anti-CD19 ADC | 8 | 0.33 mg/kg | 3 injections (1x/week) |
| 8 | rituximab | 8 | 6 mg/kg | single |

Figure 5A:
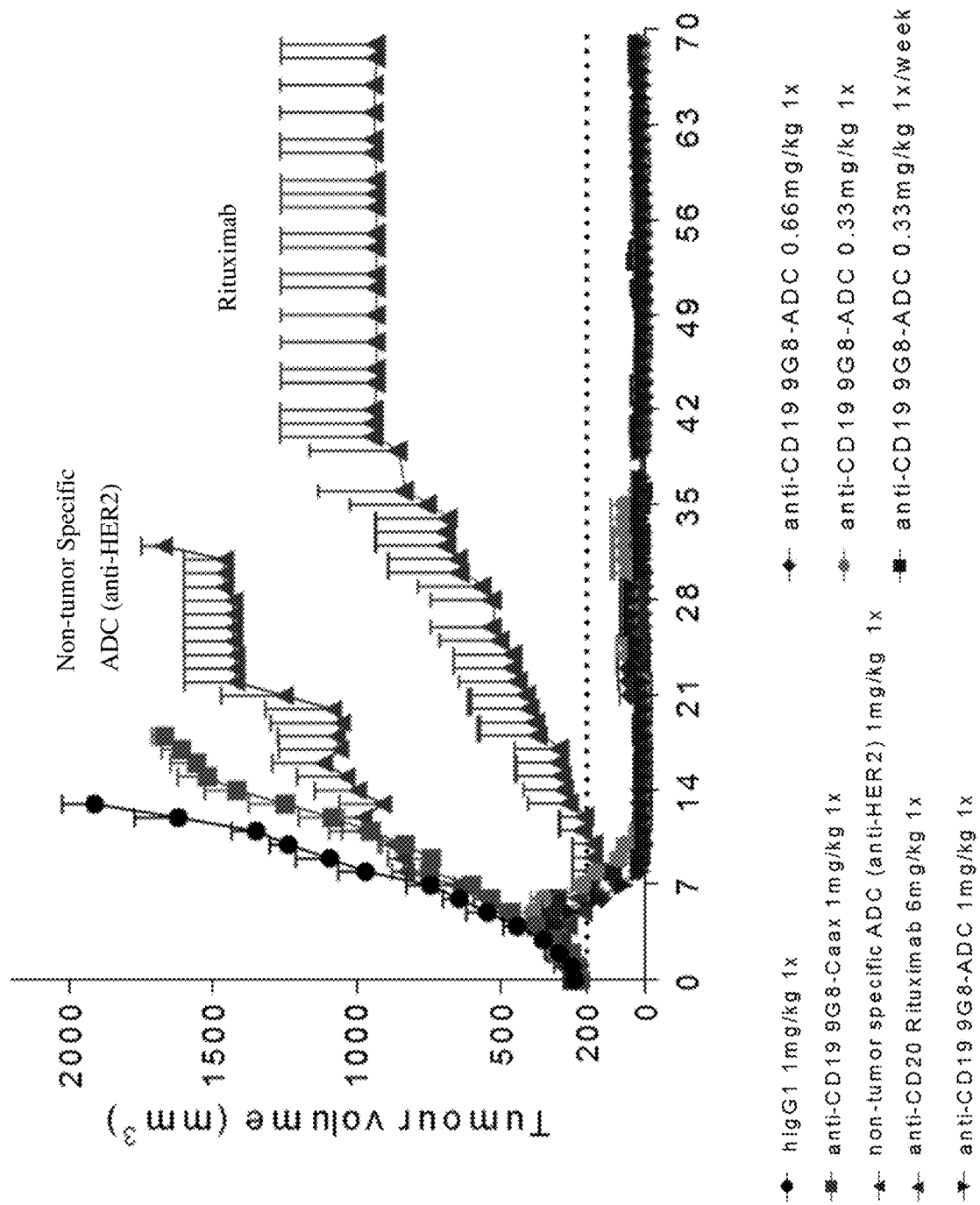
FIG. 5A shows the mean tumor volume over time of CB17-SCID mice who were implanted with Ramos cells and then treated with 9G8 anti-CD19 ADC, non-tumor specific human IgG1 anti-HER2-ADC or rituximab. Mice who were treated with the 9G8 anti-CD19 ADC displayed regression of tumor growth through day 70.
Figure 5B:
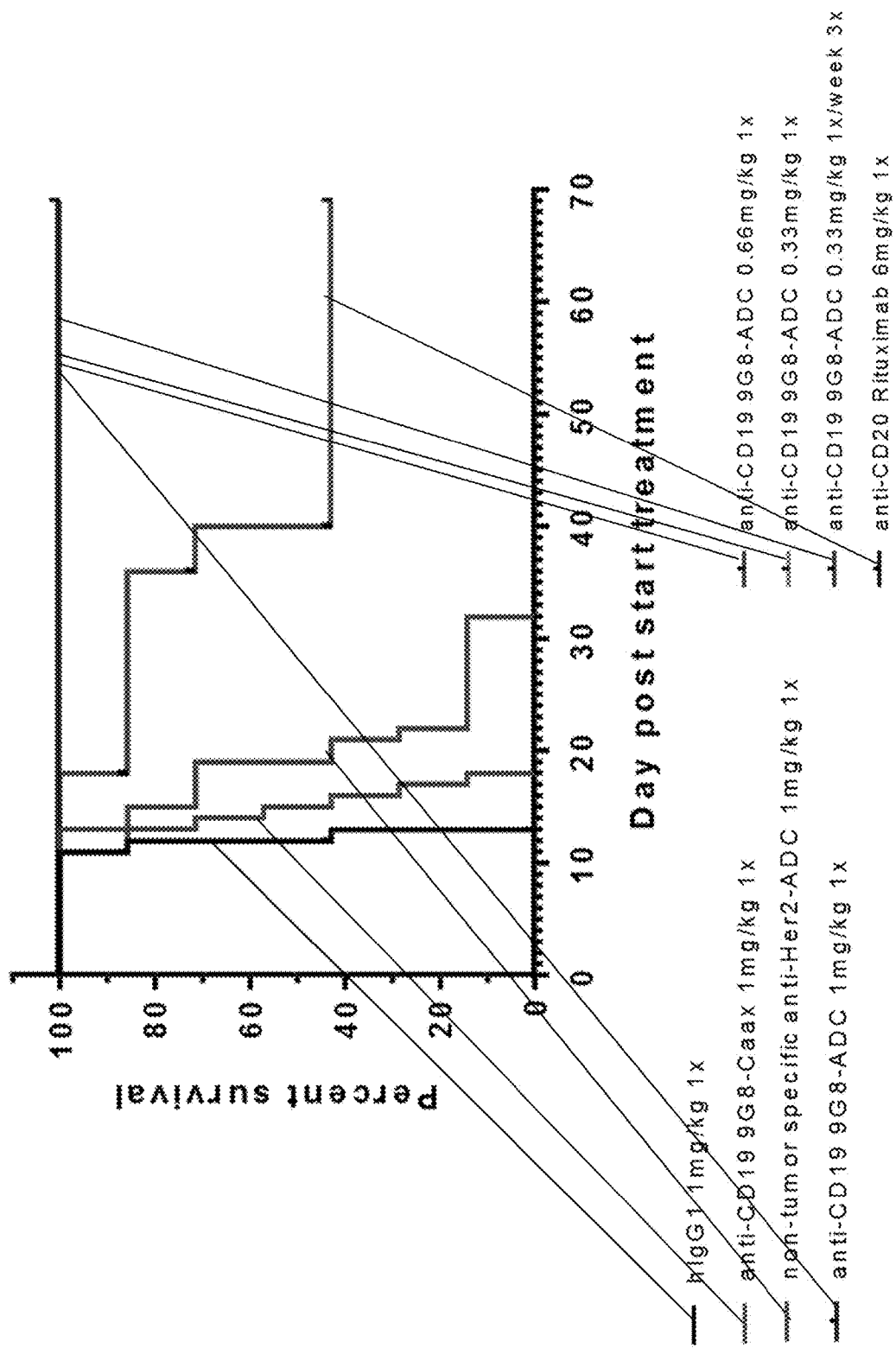
FIG. 5B shows the survival percentage of CB17-SCID mice who were implanted with Ramos cells and then treated with 9G8 anti-CD19 ADC (human IgG1 isotype, 9G8 anti-CD19 CaaX antibody), non-tumor specific human IgG1 anti-HER2-ADC or rituximab. Mice who were treated with the 9G8 anti-CD19 ADC had a 100% survival rate through day 70.
Figure 6A:
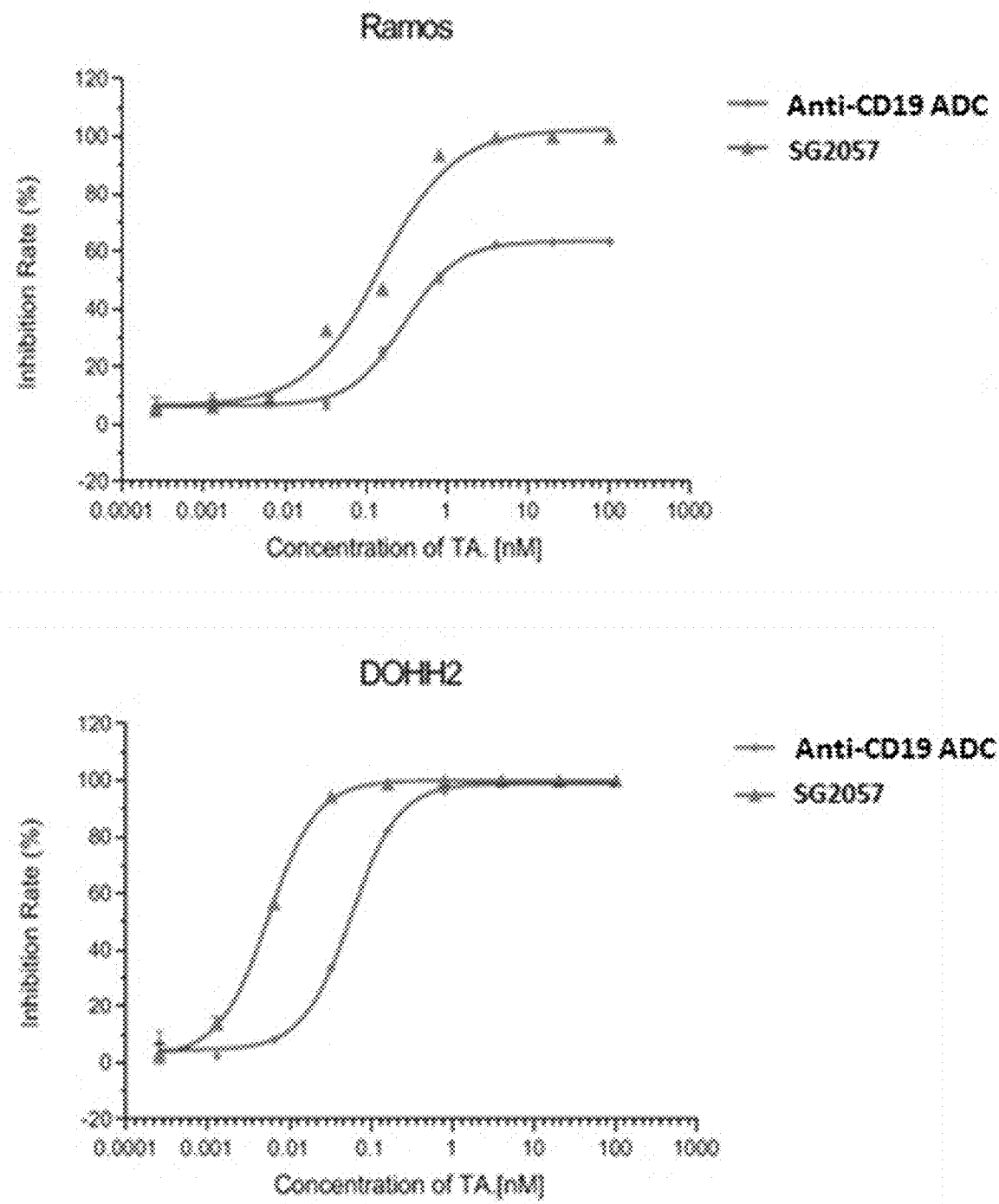
FIG. 6A shows the inhibition rate (%) of either an anti-CD19 ADC or dPBD (SG2057). The inhibition rate % of the ADC was comparable to that of dPBD.
Figure 6B:
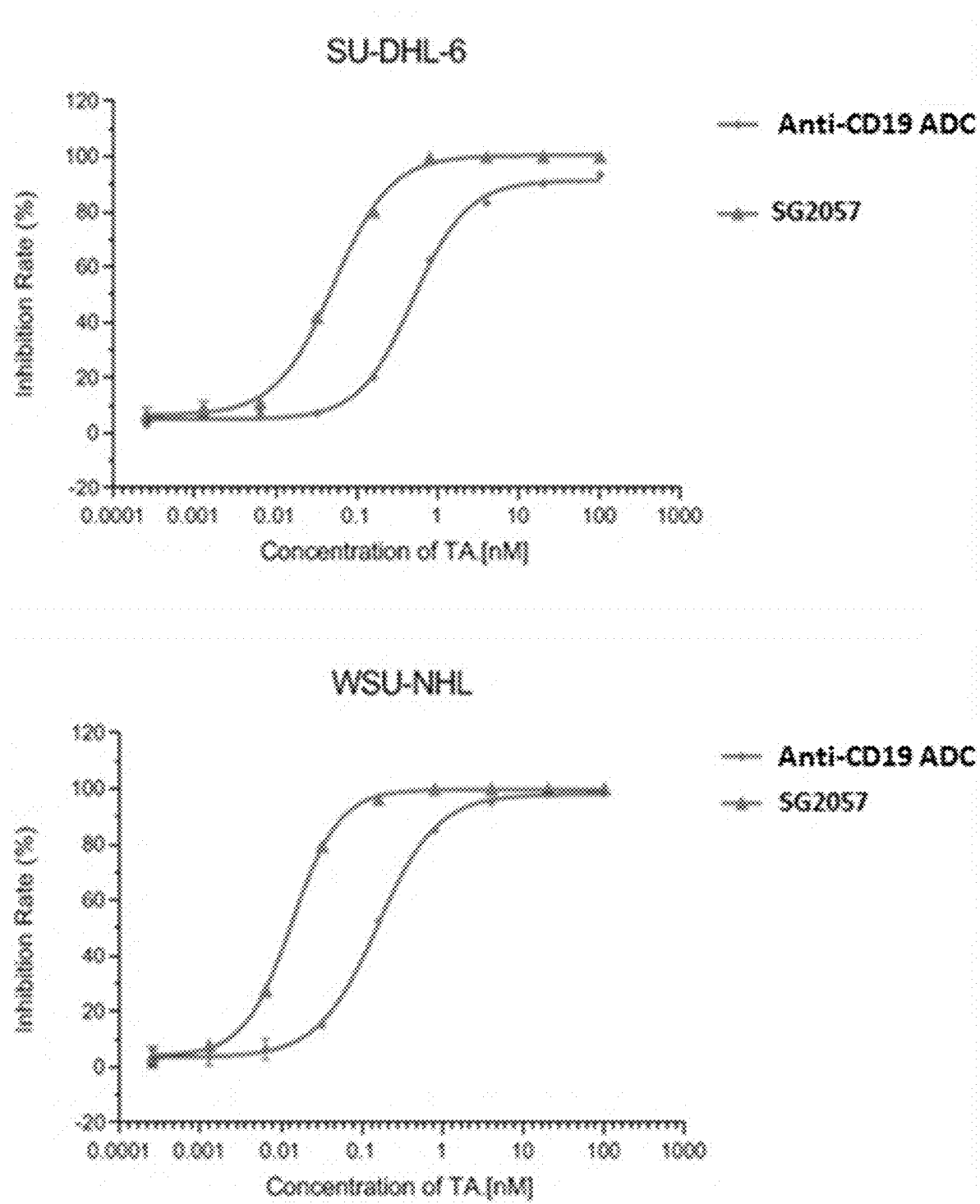
FIG. 6B shows the inhibition rate (%) of either an anti-CD19 ADC or dPBD (SG2057). The inhibition rate % of the ADC was comparable to that of dPBD.
Figure 6C:
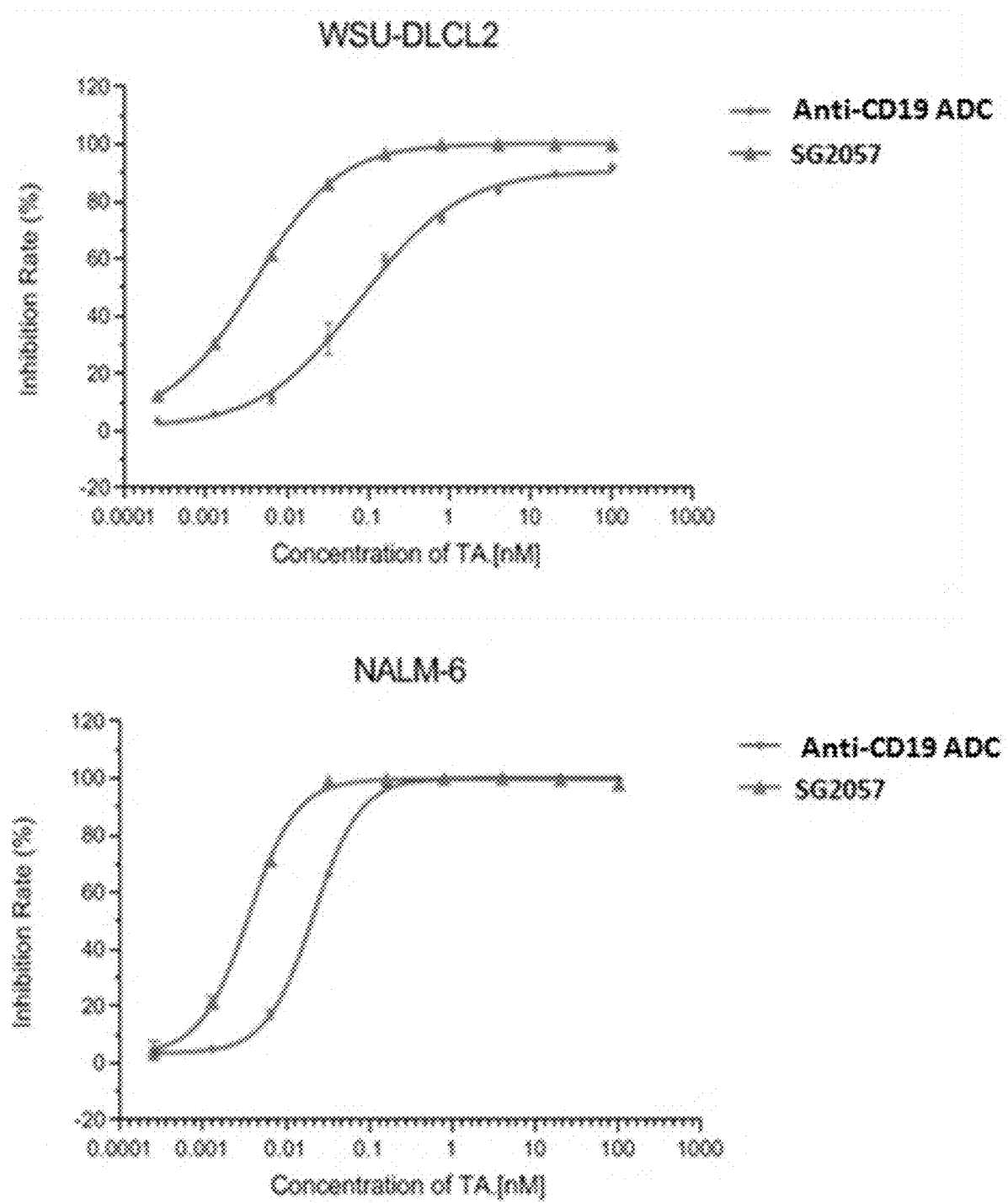
FIG. 6C shows the inhibition rate (%) of either an anti-CD19 ADC or dPBD (SG2057). The inhibition rate % of the ADC was comparable to that of dPBD.
Figure 6D:
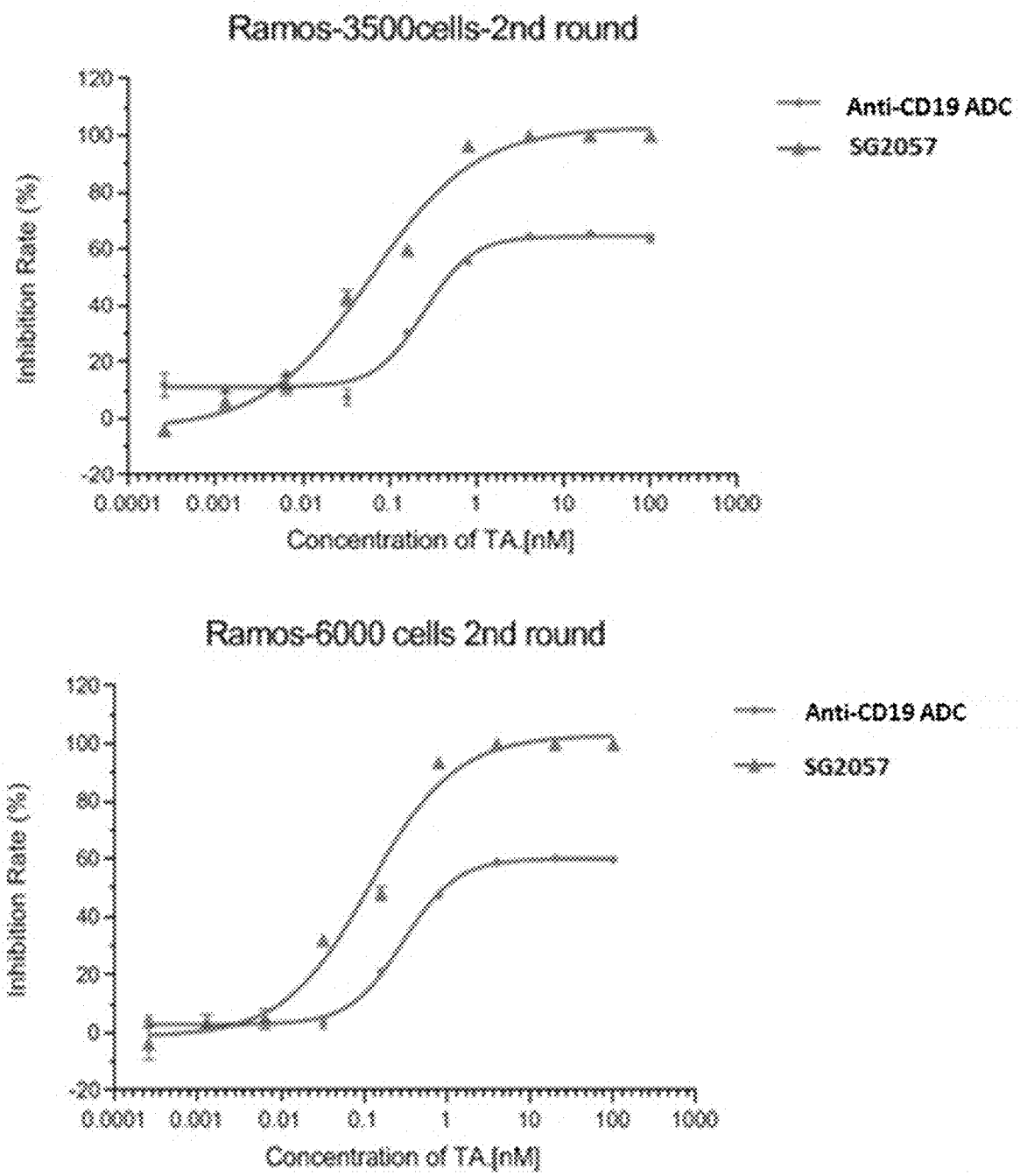
FIG. 6D shows the inhibition rate (%) of either an anti-CD19 ADC or dPBD (SG2057). The inhibition rate % of the ADC was comparable to that of dPBD.

The 9G8 anti-CD19 ADC groups displayed tumor regression through day 70, and all ice survived to day 70 (FIGS. 5A-5B). The groups who received hIgG1 isotype control, anti-CD19 9G8-Caax Ab, and non-tumor specific ADC (anti-Her2) exhibited tumor growth, and all mice within these group reached the tumor size endpoint. None survived until day 70. Of the group who were treated with rituximab, four of seven mice reached the endpoint, while three survived to day 70. No negative side effects were associated with the administration of 9G8 anti-CD19 ADC were observed.

Example 6: Exemplary In Vitro Study with Anti-CD19 Antibody 9G8

In vitro anti-tumor activity of anti-CD19 (9G8) antibody-drug conjugate was evaluated by anti-proliferation assay. Commercially available 6 B cell lymphoma cancer cell lines DOHH-2 (DSMZ, #ACC 47), NALM-6 (DSMZ, #ACC 58), Ramos (ECACC, #85030802), SU-DHL-6 (ATCC, #CRL-2959), WSU-DLCL2 (DSMZ, #ACC 575) and WSU-NHL (DSMZ, #ACC 58) were used. SG2057 was used as the drug, free toxin. Each of the cancer cell lines was seeded in a 96-well plate at 2000 to 10000 per well for the 96 hour treatment group, incubated for 2 hours, and then treated with drug and ADC at a concentration of from 0.00025 to 100 nM (5-fold times serial dilutions). After 96 hours, the number of living cells was quantified using CellTiter-Glo Luminescent cell viability assay (Promega-G7573). Inhibition rate (IR) of the drug and ADC were determined by the following formula: IR (%)=(1−(RLU compound−RLU blank)/(RLU control−RLU blank))*100%. The inhibitions of different dose of samples were calculated in Excel file, and then were used to plot inhibition curve and evaluate related parameters, such as Bottom (%), Top (%) and Relative IC50. The data were interpreted by GraphPad Prism and are shown in FIG. 6. The $IC_{50}$ for each experiment and treatment was calculated (See table below). The inhibition rate of 9G8 anti-CD19 ADC was comparable to that of dPBD free toxin (SG2057).

| Test samples | $IC_{50}$ (nM) | | | | | |
|---|---|---|---|---|---|---|
| | Ramos | SU-DHL-6 | WSU-DLCL2 | DOHH2 | WSU-NHL | NALM6 |
| Free dPBD (SG2057) | 0.15 | 0.05 | 0.004 | 0.0054 | 0.013 | 0.0035 |
| Anti-CD19 ADC | 0.30 | 0.50 | 0.080 | 0.056 | 0.15 | 0.021 |

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

We claim:

1. An antibody conjugate comprising Formula I or pharmaceutically acceptable salt or solvate thereof:

$$Ab\text{-}(X)_y \qquad \text{Formula I}$$

wherein:

Ab is an anti-CD19 antibody or antigen-binding fragment thereof, or a bispecific antibody comprising a first arm that binds CD19, wherein Ab comprises a variable heavy chain complementarity determining region 1 (CDRH1), a variable heavy chain complementarity determining region 2 (CDRH2), a variable heavy chain complementarity determining region 3 (CDRH3), a variable light chain complementarity determining region 1 (CDRL1), a variable light chain complementarity determining region 2 (CDRL2), and a variable light chain complementarity determining region 3 (CDRL3); wherein, (a) (i) CDRH1 comprises the amino acid sequence of SEQ ID NO: 23;
   (ii) CDRH2 comprises the amino acid sequence of SEQ ID NO: 24;
   (iii) CDRH3 comprises the amino acid sequence of SEQ ID NO: 25;
   (iv) CDRL1 comprises the amino acid sequence of SEQ ID NO: 32;
   (v) CDRL2 comprises the amino acid sequence of SEQ ID NO: 33; and
   (vi) CDRL3 comprises the amino acid sequence of SEQ ID NO: 34;
(b) (i) CDRH1 comprises the amino acid sequence of SEQ ID NO: 23;
   (ii) CDRH2 comprises the amino acid sequence of SEQ ID NO: 24;
   (iii) CDRH3 comprises the amino acid sequence of SEQ ID NO: 26;
   (iv) CDRL1 comprises the amino acid sequence of SEQ ID NO: 32;
   (v) CDRL2 comprises the amino acid sequence of SEQ ID NO: 33; and
   (vi) CDRL3 comprises the amino acid sequence of SEQ ID NO: 35;
(c) (i) CDRH1 comprises the amino acid sequence of SEQ ID NO: 23;
   (ii) CDRH2 comprises the amino acid sequence of SEQ ID NO: 24;
   (iii) CDRH3 comprises the amino acid sequence of SEQ ID NO: 26;
   (iv) CDRL1 comprises the amino acid sequence of SEQ ID NO: 32;
   (v) CDRL2 comprises the amino acid sequence of SEQ ID NO: 33; and
   (vi) CDRL3 comprises the amino acid sequence of SEQ ID NO: 36;
(d) (i) CDRH1 comprises the amino acid sequence of SEQ ID NO: 23;
   (ii) CDRH2 comprises the amino acid sequence of SEQ ID NO: 24;
   (iii) CDRH3 comprises the amino acid sequence of SEQ ID NO: 27;
   (iv) CDRL1 comprises the amino acid sequence of SEQ ID NO: 37;
   (v) CDRL2 comprises the amino acid sequence of SEQ ID NO: 38; and
   (vi) CDRL3 comprises the amino acid sequence of SEQ ID NO: 40;
(e) (i) CDRH1 comprises the amino acid sequence of SEQ ID NO: 23;
   (ii) CDRH2 comprises the amino acid sequence of SEQ ID NO: 24;
   (iii) CDRH3 comprises the amino acid sequence of SEQ ID NO: 28;
   (iv) CDRL1 comprises the amino acid sequence of SEQ ID NO: 41;
   (v) CDRL2 comprises the amino acid sequence of SEQ ID NO: 42; and
   (vi) CDRL3 comprises the amino acid sequence of SEQ ID NO: 43; or
(f) (i) CDRH1 comprises the amino acid sequence of SEQ ID NO: 29;

(ii) CDRH2 comprises the amino acid sequence of SEQ ID NO: 30;
(iii) CDRH3 comprises the amino acid sequence of SEQ ID NO: 31;
(iv) CDRL1 comprises the amino acid sequence of SEQ ID NO: 44;
(v) CDRL2 comprises the amino acid sequence of SEQ ID NO: 45; and
(vi) CDRL3 comprises the amino acid sequence of SEQ ID NO: 46;

and wherein each X is, independently, a chemical moiety comprising one or more active agents and a linker, wherein the linker links Ab to the active agent(s); and y is an integer between 1 to 20.

2. The antibody conjugate of claim 1, wherein Ab further comprises a combination of a variable heavy chain comprising the amino acid sequence of SEQ ID NO: 2, 6, 12, 16, or 20, and a variable light chain comprising the amino acid sequence of SEQ ID NO: 4, 8, 10, 14, 18, or 22.

3. The antibody conjugate of claim 1, wherein Ab further comprises a combination of a variable heavy chain sequence and a variable light chain sequence selected from:

(a) a variable heavy chain comprising the amino acid sequence of SEQ ID NO: 2 and a variable light chain comprising the amino acid sequence of SEQ ID NO: 4;

(b) a variable heavy chain comprising the amino acid sequence of SEQ ID NO: 6, and a variable light chain comprising the amino acid sequence of SEQ ID NO: 8;

(c) a variable heavy chain comprising the amino acid sequence of SEQ ID NO: 6 and a variable light chain comprising the amino acid sequence of SEQ ID NO: 10;

(d) a variable heavy chain comprising the amino acid sequence of SEQ ID NO: 12 and a variable light chain comprising the amino acid sequence of SEQ ID NO: 14;

(e) a variable heavy chain comprising the amino acid sequence of SEQ ID NO: 16 and a variable light chain comprising the amino acid sequence of SEQ ID NO: 18; and (f) a variable heavy chain comprising the amino acid sequence of SEQ ID NO: 20 and a variable light chain comprising the amino acid sequence of SEQ ID NO: 22.

4. The antibody conjugate of claim 1, wherein the CD19 is human CD19.

5. The antibody conjugate of claim 1, wherein Ab is a monoclonal antibody, a single chain antibody (scAb), a Fab fragment, a F(ab')$_2$ fragment, a single chain variable fragment (scFv), a scFv-Fc fragment, a multimeric antibody, or a bispecific antibody.

6. The antibody conjugate of claim 1, wherein Ab is a chimeric, humanized or fully human monoclonal antibody.

7. The antibody conjugate of claim 1, wherein Ab is an IgG isotype.

8. The antibody conjugate of claim 1, wherein Ab is an IgG1 isotype.

9. The antibody conjugate of claim 1, wherein the link between Ab and the active agent is cleavable.

10. The antibody conjugate of claim 1, wherein X is a compound of Formula II:

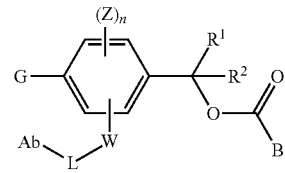

Formula II

G is a glucuronic acid moiety or

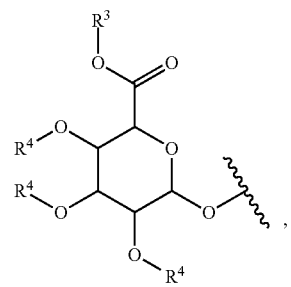

wherein $R^3$ is hydrogen or a carboxyl protecting group, and each $R^4$ is independently hydrogen or a hydroxyl protecting group;

B is an active agent;

$R^1$ and $R^2$ are each independently hydrogen, $C_{1-8}$ alkyl, or $C_{3-8}$ cycloalkyl; or W is —C(O)—, —C(O)NR'—, —C(O)O—, —SO$_2$NR'—, —P(O)R"NR'—, —SONR'—, or —PO$_2$NR'—, wherein the C, S, or P is directly bound to the phenyl ring, and R' and R" are each independently hydrogen, $C_{1-8}$ alkyl, $C_{3-8}$ cycloalkyl, $C_{1-8}$ alkoxy, $C_{1-8}$ alkylthio, mono- or di-$C_{1-8}$ alkylamino, $C_{3-20}$ heteroaryl or $C_{6-20}$ aryl;

each instance of Z is, independently, $C_{1-8}$ alkyl, halogen, cyano, or nitro;

n is an integer of 0 to 3; and

L is a linker connecting Ab and W.

11. The antibody conjugate of claim 10, wherein L satisfies at least one of the following:

(i) L includes at least one unsaturated bond;
(ii) two atoms within L are substituted with a bivalent substituent such that the substituent; with the atoms that it bridges, completes a heteroarylene;
(iii) L is a $C_{1-50}$ alkylene or 1-50 atom heteroalkylene; or
(iv) L is a $C_{1-50}$ alkylene substituted with one or more $C_{1-20}$ alkyls.

12. The antibody conjugate of claim 10, wherein L includes at least one isoprenyl unit comprising Formula III:

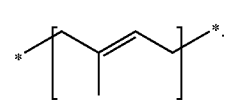

Formula III

13. The antibody conjugate of claim 10, wherein $R^3$ is hydrogen and each $R^4$ is hydrogen.

14. The antibody conjugate of claim 10, wherein n is 0.

15. The antibody conjugate of claim 10, wherein W is —C(O)—, —C(O)NR'—, or —C(O)O—.

16. The antibody conjugate of claim 10, wherein:
G is

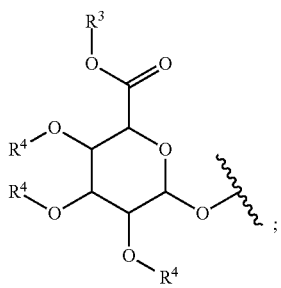

W is —C(O)NR'—, wherein C(O) is bonded to the phenyl ring and NR' is bonded to L; and
$R^1$ and $R^2$ are each hydrogen.

17. The antibody conjugate of claim 10, wherein the linker comprises a peptide and the peptide comprises at least one hydrophilic amino acid.

18. The antibody conjugate of claim 17, wherein the peptide comprises 2 to 20 amino acids.

19. The antibody conjugate of claim 10, wherein the linker is covalently bound to Ab by a thioether bond, and the thioether bond comprises a sulfur atom of a cysteine of the Ab.

20. The antibody conjugate of claim 19, wherein:
Ab comprises an amino acid motif, that is recognized by an isoprenoid transferase; and
the thioether bond comprises a sulfur atom of a cysteine of the amino acid motif.

21. The antibody conjugate of claim 11, wherein L is a 3-50 heteroalkylene comprising an oxime, wherein:
the oxygen atom of the oxime is on the side of L that is linked to W and the carbon atom of the oxime is on the side of L that is linked to Ab; or
the carbon atom of the oxime is on the side of L that is linked to W and the oxygen atom of the oxime is on the side of L that is linked to Ab.

22. The antibody conjugate of claim 10, wherein L further comprises a connection unit comprising Formula VIII or IX:

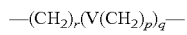 Formula VIII,

 Formula IX;

V is a single bond, —O—, —S—, —$NR^{21}$—, —C(O)$NR^{22}$—, —$NR^{23}$C(O)—, —$NR^{24}SO_2$—, or —$SO_2NR^{25}$—;
X is —O—, $C_{1-8}$ alkylene, or —$NR^{21}$—;
$R^{21}$ to $R^{25}$ are each independently hydrogen, $C_{1-6}$ alkyl, $C_{1-6}$ alkyl $C_{6-20}$ aryl, or $C_{1-6}$ alkyl $C_{3-20}$ heteroaryl;
r is an integer of 1 to 10;
p is an integer of 0 to 12;
q is an integer of 1 to 20; and
w is an integer of 1 to 20.

23. The antibody conjugate of claim 10, wherein L further comprises a binding unit formed by a 1,3-dipolar cycloaddition reaction, hetero-Diels-Alder reaction, nucleophilic substitution reaction, non-aldol type carbonyl reaction, addition to carbon-carbon multiple bond, oxidation reaction, or click reaction.

24. The antibody conjugate of claim 23, wherein the binding unit comprises Formula IV, V, VI, or VII:

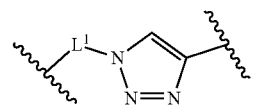 Formula IV

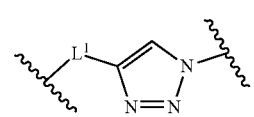 Formula V

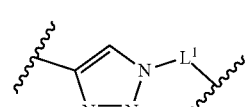 Formula VI

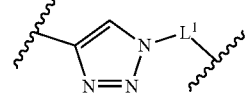 Formula VII

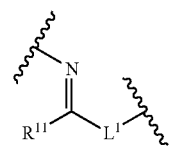

$L^1$ is a single bond or $C_{1-30}$ alkylene; and
$R^{11}$ is hydrogen or $C_{1-10}$ alkyl.

25. The antibody conjugate of claim 10, wherein the compound comprises a structure selected from:

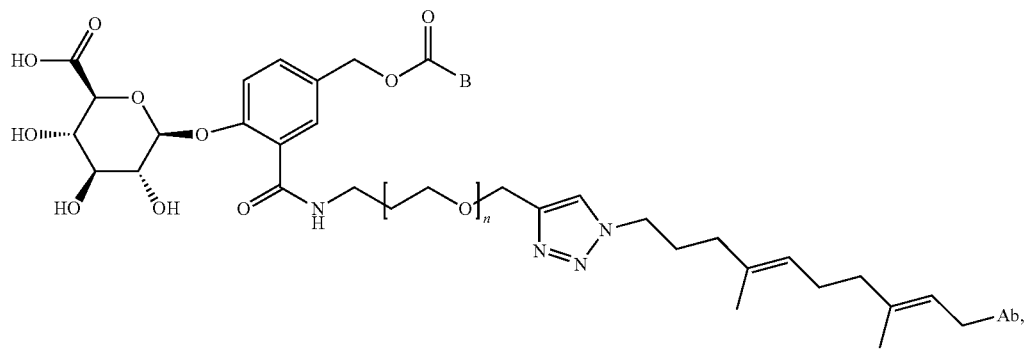

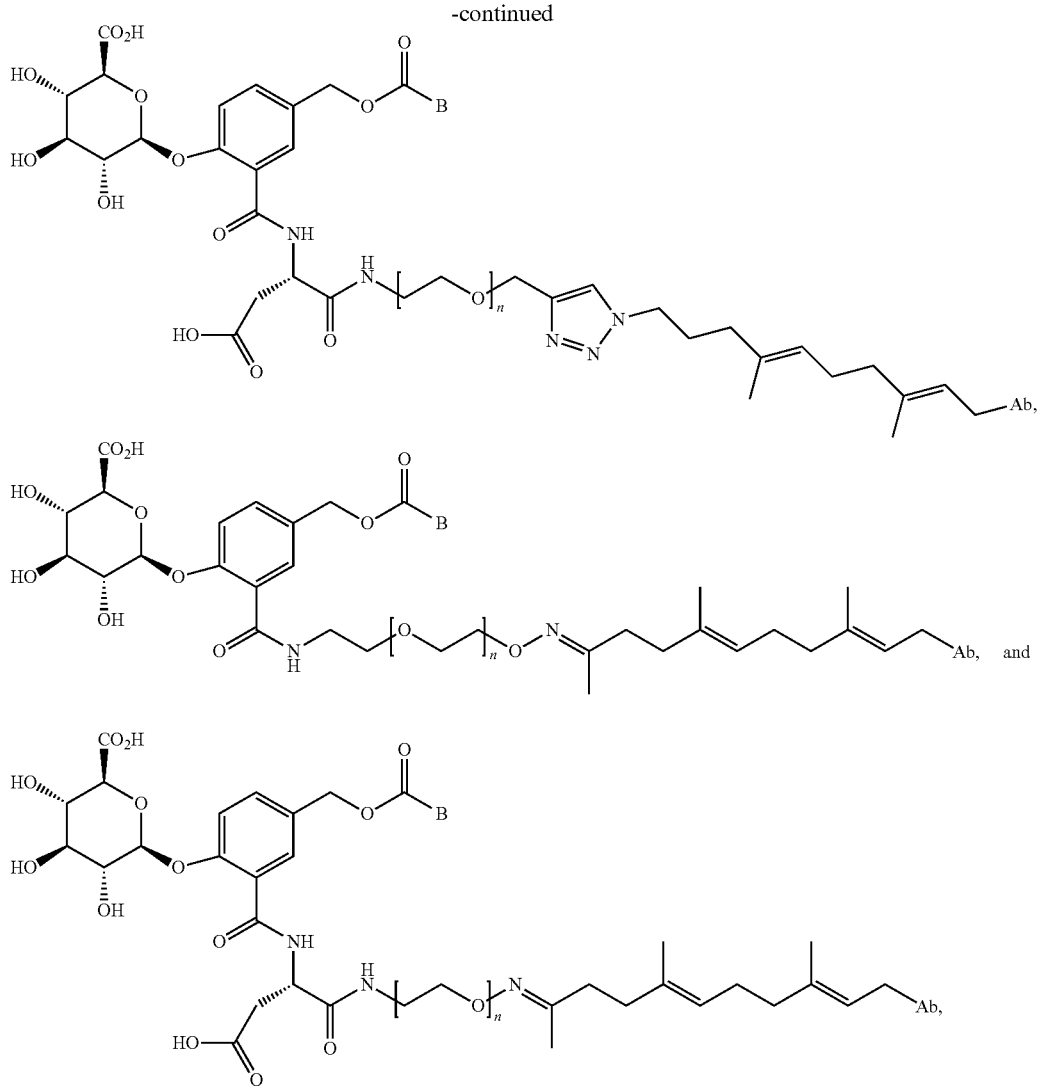

wherein n is an integer from 1 to 20.

26. The antibody conjugate of claim 10, wherein L further comprises one or more branched linkers covalently coupled to Ab, wherein:

i) each branched linker comprises a branching unit (BR) covalently coupled to Ab by a primary linker (PL);

ii) each branched linker comprises a first branch (B1), which couples a first active agent to the branching unit and comprises a secondary linker (SL) and a cleavage group (CG); and iii) each branched linker further comprises a second branch (B2), in which either a) a second active agent is covalently coupled to the branching unit by a secondary linker (SL) and a cleavage group (CG); or b) a polyethylene glycol moiety is covalently coupled to the branching unit, and wherein each cleavage group can be hydrolyzed to release the active agent from the antibody conjugate.

27. The antibody conjugate of claim 26, wherein at least one branching unit has the structure

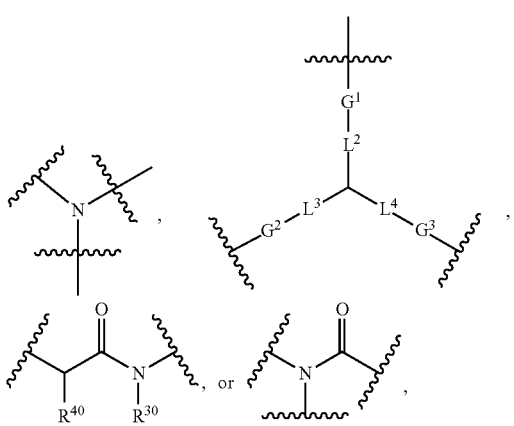

wherein $L^2$, $L^3$, $L^4$ is each independently a direct bond or —$C_nH_{2n}$— where n is a integer of 1 to 30, wherein G$^1$, G$^2$, G$^3$ is each independently a bond,

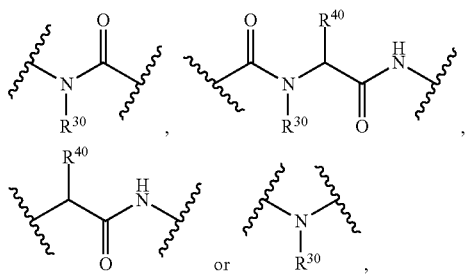

wherein R$^{30}$ is hydrogen or C$_{1-30}$ alkyl; and R$^{40}$ is a hydrogen or C$_{1-10}$ alkylene.

28. The antibody conjugate of claim 26, comprising the structure:

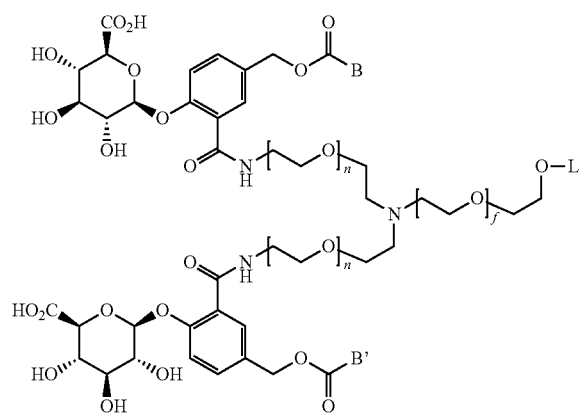

wherein:
B and B' are active agents, which may be the same or different;
n, independently for each occurrence, is an integer from 0 to 30;
f, independently for each occurrence, is an integer from 0 to 30; and
L is a linkage to the Ab.

29. The antibody conjugate of claim 28, wherein n is an integer from 1 to 20.

30. The antibody conjugate of claim 26, wherein at least one branched linker is coupled to Ab, and the branched linker is coupled to at least two active agents.

31. The antibody conjugate of claim 30, wherein two, three or four branched linkers are coupled to Ab.

32. The antibody conjugate of claim 26, wherein the conjugate comprises at least two different active agents.

33. The antibody conjugate of claim 27, wherein the branching unit is a lysine unit.

34. The antibody conjugate of claim 10, wherein the active agent is an immunomodulatory compound, an anticancer agent, an antiviral agent, an antibacterial agent, an antifungal agent, or an antiparasitic agent.

35. The antibody conjugate of claim 10, wherein the active agent is independently selected from:
(a) erlotinib, bortezomib, fulvestrant, sunitinib, letrozole, imatinib mesylate, PTK787/ZK 222584, oxaliplatin, 5-fluorouracil, leucovorin, rapamycin, lapatinib, lonafarnib, sorafenib, gefitinib, AG1478, AG1571, thiotepa, cyclophosphamide, busulfan, improsulfan, piposulfan, benzodopa, carboquone, meturedopa, uredopa, ethylenimine, altretamine, triethylenemelamine, trietylenephosphormide, triethiylenethiophosphoramide, trimethylolomelamine, bullatacin, bullatacinone, camptothecin, topotecan, bryostatin, callystatin, CC-1065, adozelesin, carzelesin, bizelesin, cryptophycin 1, cryptophycin 8, dolastatin, duocarmycin, KW-2189, CB1-TM1, eleutherobin, pancratistatin, sarcodictyin, spongistatin, chlorambucil, chlornaphazine, cholophosphamide, estramustine, ifosfamide, mechlorethamine, melphalan, novembichin, phenesterine, prednimustine, trofosfamide, uracil mustard, carmustine, chlorozotocin, fotemustine, lomustine, nimustine, ranimnustine, calicheamicin, calicheamicin gamma 1, calicheamicin omega 1, dynemicin, dynemicin A, clodronate, esperamicin, neocarzinostatin chromophore, aclacinomysins, actinomycin, anthramycin, azaserine, bleomycins, cactinomycin, carabicin, carninomycin, carzinophilin, chromomycins, dactinomycin, daunorubicin, detorubicin, 6-diazo-5-oxo-L-norleucine, doxorubicin, morpholino-doxorubicin, cyanomorpholino-doxorubicin, 2-pyrrolino-doxorubicin, liposomal doxorubicin, deoxydoxorubicin, epirubicin, esorubicin, marcellomycin, mitomycin C, mycophenolic acid, nogalamycin, olivomycins, peplomycin, potfiromycin, puromycin, quelamycin, rodorubicin, streptomigrin, streptozocin, tubercidin, ubenimex, zinostatin, zorubicin, 5-fluorouracil, denopterin, methotrexate, pteropterin, trimetrexate, fludarabine, 6-mercaptopurine, thiamiprine, thiguanine, ancitabine, azacitidine, 6-azauridine, carmofur, cytarabine, dideoxyuridine, doxifluridine, enocitabine, floxuridine, calusterone, dromostanolone propionate, epitiostanol, mepitiostane, testolactone, aminoglutethimide, mitotane, trilostane, folinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, etoglucid, gallium nitrate, hydroxyurea, lentinan, lonidainine, maytansine, ansamitocins, mitoguazone, mitoxantrone, mopidanmol, nitraerine, pentostatin, phenamet, pirarubicin, losoxantrone, 2-ethylhydrazide, procarbazine, polysaccharide-k, razoxane, rhizoxin, sizofiran, spirogermanium, tenuazonic acid, triaziquone, 2,2',2"-trichlorotriethylamine, T-2 toxin, verracurin A, roridin A, and anguidine, urethane, vindesine, dacarbazine, mannomustine, mitobronitol, mitolactol, pipobroman, gacytosine, arabinoside, cyclophosphamide, thiotepa, paclitaxel, albumin-engineered nanoparticle formulation of paclitaxel, doxetaxel, chlorambucil, gemcitabine, 6-thioguanine, mercaptopurine, cisplatin, carboplatin, vinblastine, platinum, etoposide, ifosfamide, mitoxantrone, vincristine, vinorelbine, novantrone, teniposide, edatrexate, daunomycin, aminopterin, xeloda, ibandronate, CPT-11, topoisomerase inhibitor RFS 2000, difluoromethylornithine, retinoic acid, capecitabine, or pharmaceutically acceptable salts, solvates or acids of any of the foregoing;
(b) monokine, a lymphokine, a traditional polypeptide hormone, parathyroid hormone, thyroxine, relaxin, prorelaxin, a glycoprotein hormone, follicle stimulating hormone, thyroid stimulating hormone, luteinizing hormone, hepatic growth factor fibroblast growth factor, prolactin, placental lactogen, tumor necrosis factor-α, tumor necrosis factor-β, mullerian-inhibiting substance, mouse gonadotropin-associated peptide, inhibin, activin, vascular endothelial growth factor, thrombopoietin, erythropoietin, an osteoinductive factor, an interferon, interferon-α, interferon-β, interferon-γ, a colony stimulating factor ("CSF"), macrophage-CSF, granulocyte-macrophage-CSF, granulocyte-CSF, an interleukin ("IL"), IL-1, IL-1a, IL-2, IL-3, IL-4, IL-5, IL-6, IL-7, IL-8, IL-9, IL-10, IL-11, IL-12, a tumor necrosis factor, TNF-α, TNF-β, LIF, kit ligand, or a combination of any of the foregoing;

(c) diphtheria toxin, botulium toxin, tetanus toxin, dysentery toxin, cholera toxin, amanitin, amanitin derivatives, α-amanitin, pyrrolobenzodiazepine, tetrodotoxin, brevetoxin, ciguatoxin, ricin, AM toxin, auristatin, tubulysin, geldanamycin, maytansinoid, calicheamicin, daunomycin, doxorubicin, methotrexate, vindesine, SG2285, dolastatin, cryptophycin, camptothecin, rhizoxin, CC-1065, duocarmycin, an enediyne antibiotic, esperamicin, epothilone, azonafide, aplidine, a toxoid, or a combination of any of the foregoing;

(d) an affinity ligand;

(e) a radioactive label, $^{32}P$, $^{35}S$, a fluorescent dye, an electron dense reagent, an enzyme, biotin, streptavidin, dioxigenin, a hapten, an immunogenic protein, a nucleic acid molecule with a sequence complementary to a target, or a combination of any of the foregoing;

(f) an immunomodulatory compound, an anti-cancer agent, an anti-viral agent, an anti-bacterial agent, an anti-fungal agent, and an anti-parasitic agent, or a combination of any of the foregoing;

(g) tamoxifen, raloxifene, droloxifene, 4-hydroxytamoxifen, trioxifene, keoxifene, LY117018, onapristone, or toremifene;

(h) 4(5)-imidazoles, aminoglutethimide, megestrol acetate, exemestane, letrozole, or anastrozole;

(i) flutamide, nilutamide, bicalutamide, leuprolide, goserelin, or troxacitabine;

(j) an aromatase inhibitor;

(k) a protein kinase inhibitor;

(l) a lipid kinase inhibitor;

(m) an antisense oligonucleotide;

(n) a ribozyme;

(o) a vaccine; and (p) an anti-angiogenic agent.

36. The antibody conjugate of claim 10, wherein:
Ab is an anti-CD19 antibody;
the active agent is a pyrrolobenzodiazepine dimer;
the compound connects Ab to the N10 or N'10 position of the pyrrolobenzodiazepine dimer; and
y is an integer between 1 to 20.

37. The antibody conjugate of claim 36, wherein the pyrrolobenzodiazepine dimer comprises Formula X or Formula XI:

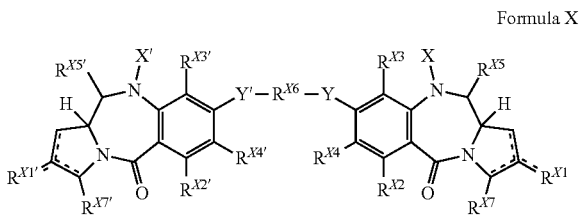

Formula X

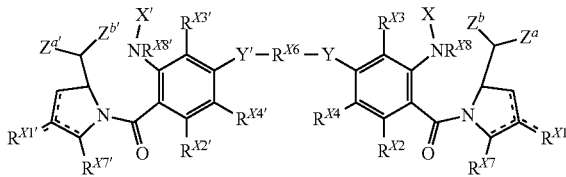

Formula XI wherein:
the dotted lines indicate the optional presence of a double bond between C1 and C2, or between C2 and C3; and between C'1 and C'2, or between C'2 or C'3;

$R^{X1}$ and $R^{X1'}$ are independently selected from H, OH, =O, =$CH_2$, CN, $R^m$, $OR^m$, =CH—$R^{m'}$=C($R^{m'}$)$_2$, O—$SO_2$—$R^m$, $CO_2R^m$, $COR^m$, halo and dihalo, $R^m$ is independently selected from $R^m$, $CO_2R^m$, $COR^m$, CHO, $CO_2H$, and halo, each $R^m$ is independently selected from $C_{1-12}$ alkyl, $C_{2-12}$ alkenyl, $C_{2-12}$ alkynyl, $C_{5-20}$ aryl, $C_{5-20}$ heteroaryl, $C_{3-6}$ cycloalkyl, 3 to 7-membered heterocyclyl, 3 to 7-membered heterocycloalkyl, and 5 to 7-membered heteroaryl;

$R^{X2}$, $R^{X2'}$, $R^{X3}$, $R^{X3'}$, $R^{X5}$, and $R^{X5'}$ are each independently selected from H, $R^m$, OH, $OR^m$, SH, $SR^m$, $NH_2$, $NHR^m$, $NR^m_2$, $NO_2$, $Me_3Sn$ and halo;

$R^{X4}$ and $R^{X4'}$ are independently selected from H, $R^m$, OH, $OR^m$, SH, $SR^m$, $NH_2$, $NHR^m$, $NR^m_2$, $NO_2$, $Me_3Sn$, halo, $C_{1-6}$ alkyl, $C_{1-6}$ alkoxy, $C_{2-6}$ alkenyl, $C_{2-6}$ alkynyl, $C_{3-6}$ cycloalkyl, 3 to 7-membered heterocycloalkyl, $C_{5-12}$ aryl, 5 to 7-membered heteroaryl, —CN, —NCO, —$OR^n$, —OC(O)$R^n$, —OC(O)$NR^nR^{n'}$, —OS(O)$R^n$, —OS(O)$_2R^n$, —$SR^n$, —S(O)$R^n$, —S(O)$_2R^n$, —S(O)$NR^nR^{n'}$, —S(O)$_2NR^nR^{n'}$, —OS(O)$NR^nR^{n'}$, —OS(O)$_2NR^nR^{n'}$, —$NR^nR^{n'}$, —$NR^nC(O)R^o$, —$NR^nC(O)OR^o$, —$NR^n(O)NR^oR^{o'}$, —$NR^n$ S(O)$R^o$, —$NR^n$ S(O)$_2R^o$, —$NR^nS(O)NR^oR^{o'}$, —$NR^nS(O)_2NR^oR^{o'}$, —C(O)$R^n$, —C(O)$OR^n$ and —C(O)$NR^nR^{n'}$;

X and X' are independently selected from H, OH, $N_3$, CN, $NO_2$, SH, $NH_2$, $ONH_2$, $NHNH_2$, halo, $C_{1-8}$ alkyl, $C_{3-8}$ cycloalkyl, $C_{1-8}$ alkoxy, $C_{1-8}$ alkylthio, $C_{3-20}$ heteroaryl, $C_{5-20}$ aryl or mono- or di-$C_{1-8}$ alkylamino;

Y and Y' are independently selected from O, S, and N(H);

$R^{X6}$ is $C_{3-12}$ alkylene, $C_{3-12}$ alkenylene, or $C_{3-12}$ heteroalkylene;

$R^{X7}$ and $R^{X7'}$ are independently selected from H, $C_{1-6}$ alkyl, $C_{2-6}$ alkenyl, $C_{2-6}$ alkynyl, $C_{3-6}$ cycloalkyl, 3 to 7-membered heterocycloalkyl, $C_{6-10}$ aryl, 5 to 7-membered heteroaryl, —$OR^r$, —OC(O)$R^r$, —OC(O)$NR'W^{r'}$, —OS(O)$R^r$, —O S(O)$_2R^r$, —$SR^r$, —S(O)$R^r$, —S(O)$_2R^r$, —S(O)$NR'R^{r'}$, —S(O)$_2NR'R^{r'}$, —OS(O)$NR'R^{r'}$, —OS(O)$_2NR'$, $R^{r'}$, —$NR'R^{r'}$, —$NR'C(O)R^s$, —$NR'C(O)OR^s$, —$NR'C(O)NR^sR^{s'}$, —$NR'S(O)R^s$, —$NR'S(O)_2R^s$, —$NR'S(O)NR^sR^{s'}$, —$NR'$ S(O)$_2NR^sR^s$, —C(O)$R^r$, —C(O)$OR^s$ or —C(O)$NR'R^r$ each $R^r$, $R^{r'}$, $R^s$, and $R^{s'}$ is independently selected from H, $C_{1-7}$ alkyl, $C_{2-7}$ alkenyl, $C_{2-7}$ alkynyl, $C_{3-13}$ cycloalkyl, 3 to 7-membered heterocycloalkyl, $C_{5-10}$ aryl, and 5 to 7-membered heteroaryl;

each $R^{X8}$ and $R^{X8'}$ is independently selected from H, $C_{1-6}$ alkyl, $C_{2-6}$ alkenyl, $C_{2-6}$ alkynyl, $C_{3-6}$ heteroalkyl, 3 to 7-membered heterocycloalkyl, $C_{5-10}$ aryl, 5 to 7-membered heteroaryl, —S(O)$R^m$, —S(O)$_2R^m$, —S(O)$NR^mR^{m'}$, —S(O)$_2NR^mR^{m'}$, —$NR^mR^{m'}$, —$NR^mC(O)R^m$, —$NR^mC(O)OR^n$, —$NR^mC(O)NR'R^{r'}$, —$NR^mS$ (O)R''', —NR''' S(O)$_2$R'', —NR'''S(O)NR''R''', —NR'''S(O)$_2$NR''R''', —C(O)R''', —C(O)OR''', and —C(O)NR'''R''';

$Z^a$ is selected from OR$^{X12a}$, NR$^{X12a}$R$^{X12a}$, or SR$^{X12a}$;
$Z^b$ is selected from OR$^{X13a}$, N$^{R13a}$R$^{X13a}$, or SR$^{X13a}$;
$Z^{a'}$ is selected from OR$^{X12a'}$, NR$^{X12a'}$R$^{X12a'}$, or SR$^{X12a'}$;
$Z^{b'}$ is selected from OR$^{X13a'}$, NR$^{X13a'}$R$^{X13a'}$, or SR$^{X13a'}$;
each of R$^{X12a}$, R$^{X12a'}$, R$^{X13a'}$, and R$^{X13a'}$ is independently selected from absent, H, C$_{1-6}$ alkyl, C$_{2-6}$ alkenyl, C$_{2-6}$ alkynyl, C$_{3-6}$ cycloalkyl, 3 to 7-membered heterocycloalkyl, C$_{5-10}$ aryl, 5 to 7-membered heteroaryl, —C(O)R$^{X15a}$, —C(O)OR$^{X15a}$, and —C(O)NR$^{X15a}$R$^{X15a'}$; and each R$^{X15a}$ and R$^{X15a'}$ is independently selected from C$_{1-12}$ alkyl, C$_{2-12}$ alkenyl, C$_{2-12}$ alkynyl, C$_{5-20}$ aryl, C$_{5-20}$ heteroaryl, C$_{3-6}$ cycloalkyl, 3 to 7-membered heterocyclyl, 3 to 7-membered heterocycloalkyl, and 5 to 7-membered heteroaryl; or wherein two R$^{X13a}$ taken together with the atoms to which they are attached optionally combine to form a 3 to 7-membered heterocyclyl, 3 to 7-membered heterocycloalkyl, or 3 to 7-membered heteroaryl; and R$^{X13a'}$ and R$^{X14a'}$ taken together with the atoms to which they are attached optionally combine to form a 3 to 7-membered heterocyclyl, 3 to 7-membered heterocycloalkyl, or 3 to 7-membered heteroaryl; and wherein each R'', R''', R°, R°', R$^p$, and R$^{p'}$ is independently selected from H, C$_{1-7}$ alkyl, C$_{2-7}$ alkenyl, C$_{2-7}$ alkynyl, C$_{3-13}$ cycloalkyl, 3 to 7-membered heterocycloalkyl, C$_{5-10}$ aryl, and 5 to 7-membered heteroaryl.

38. The antibody conjugate of claim 10, wherein the compound of Formula II comprises

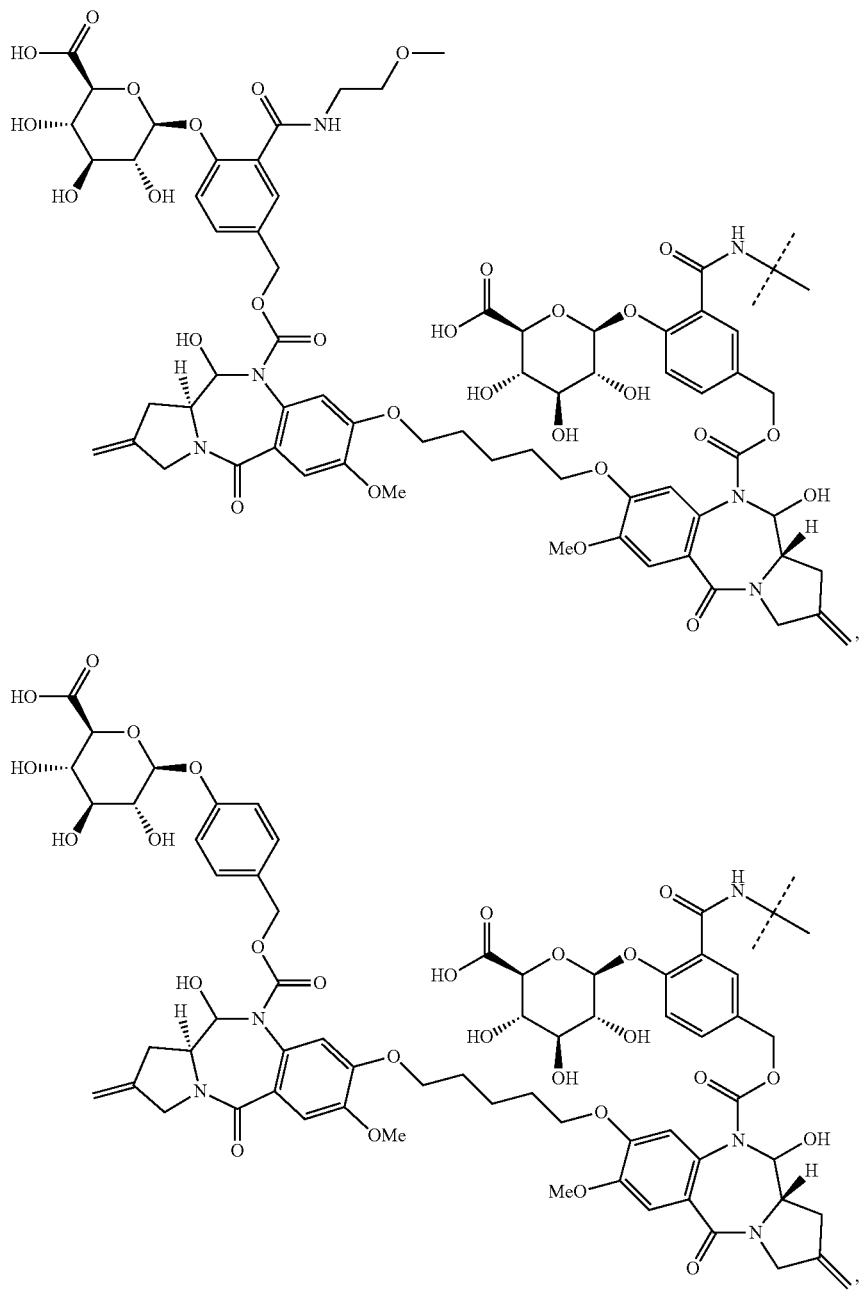

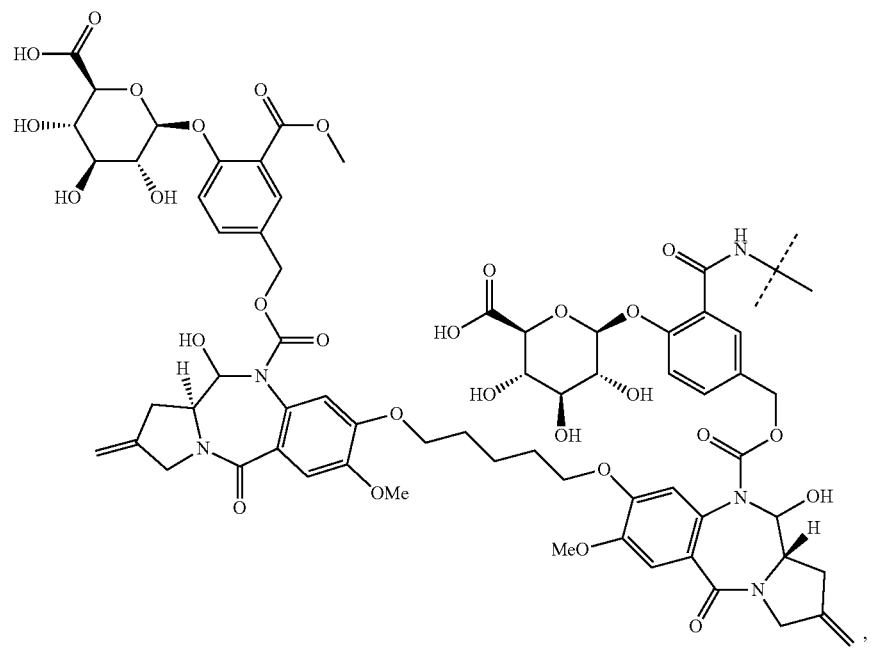
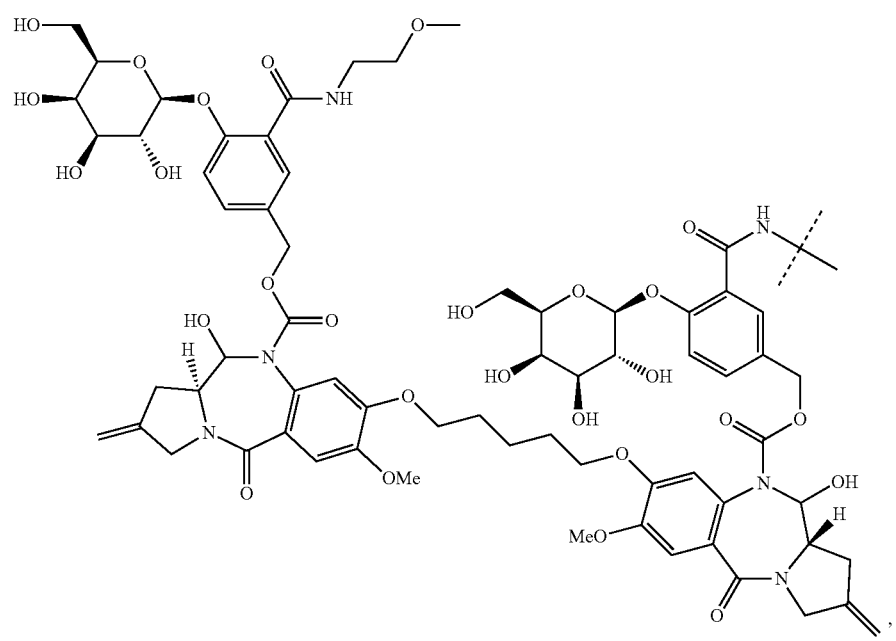

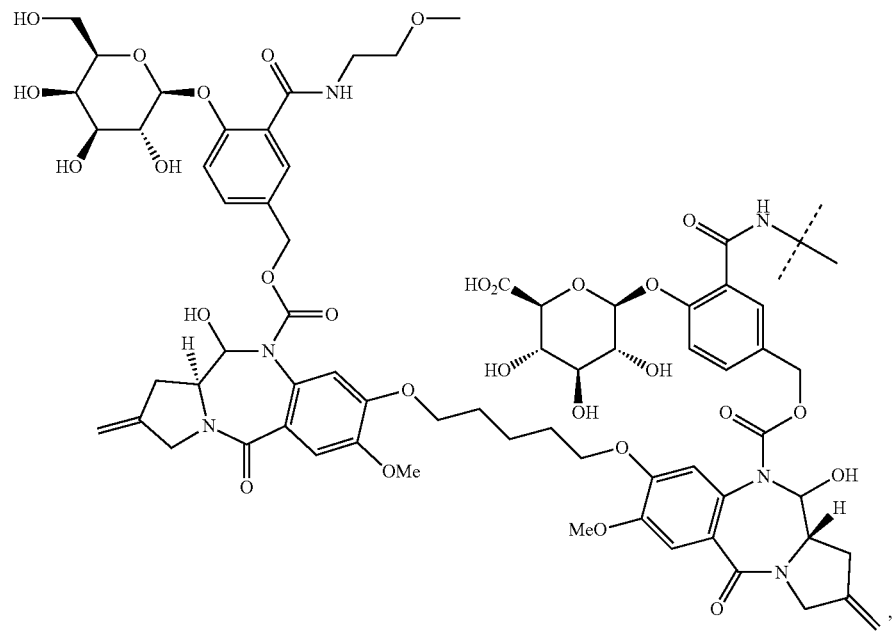
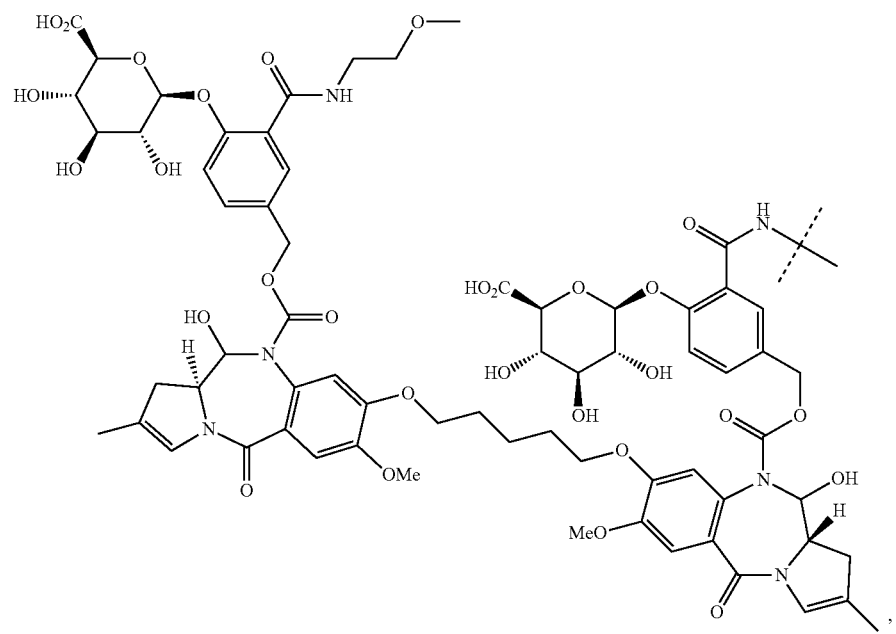

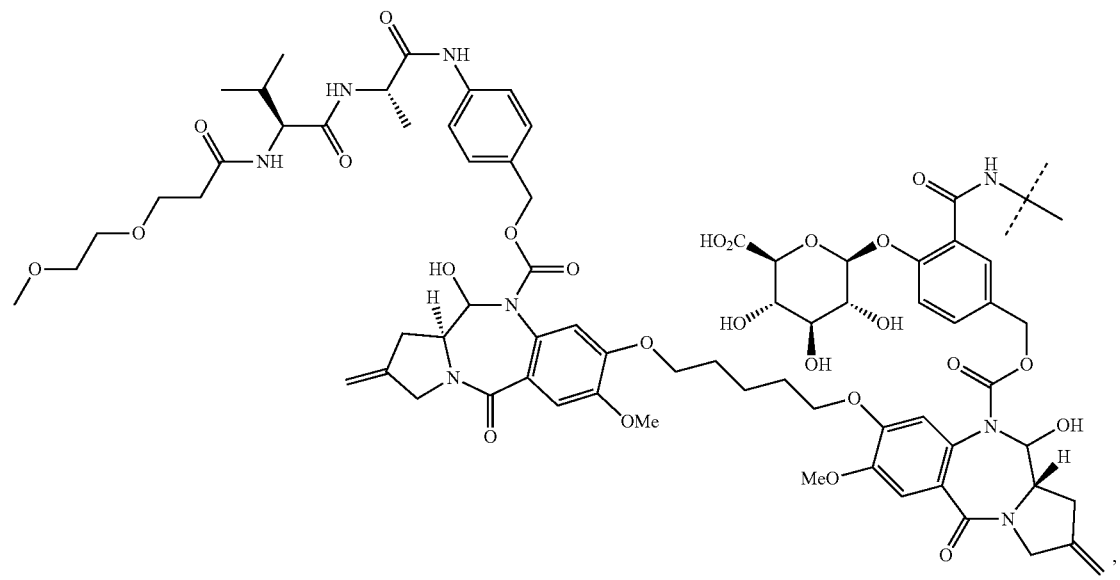
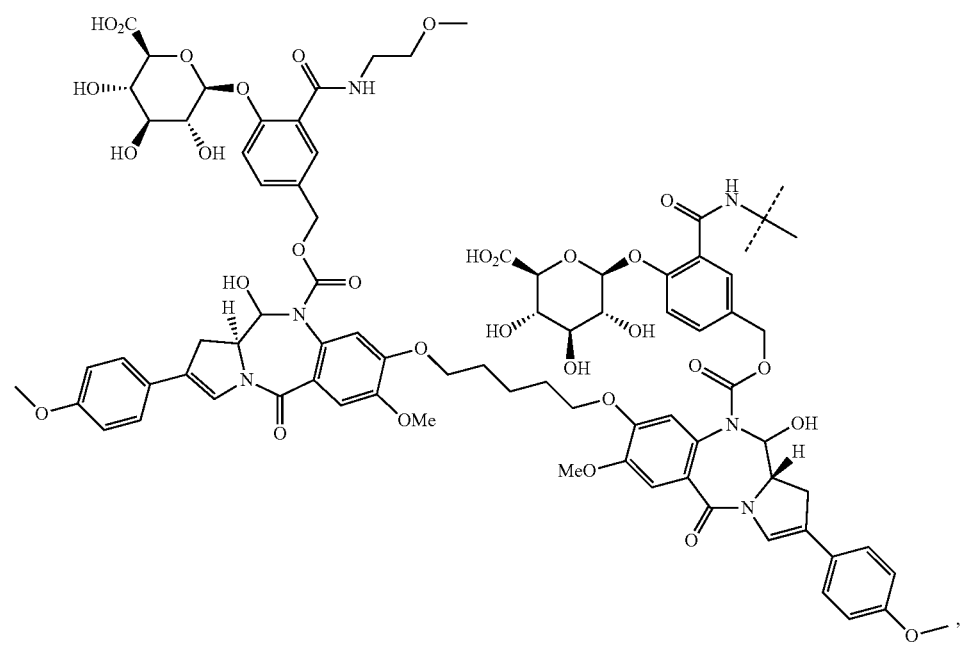

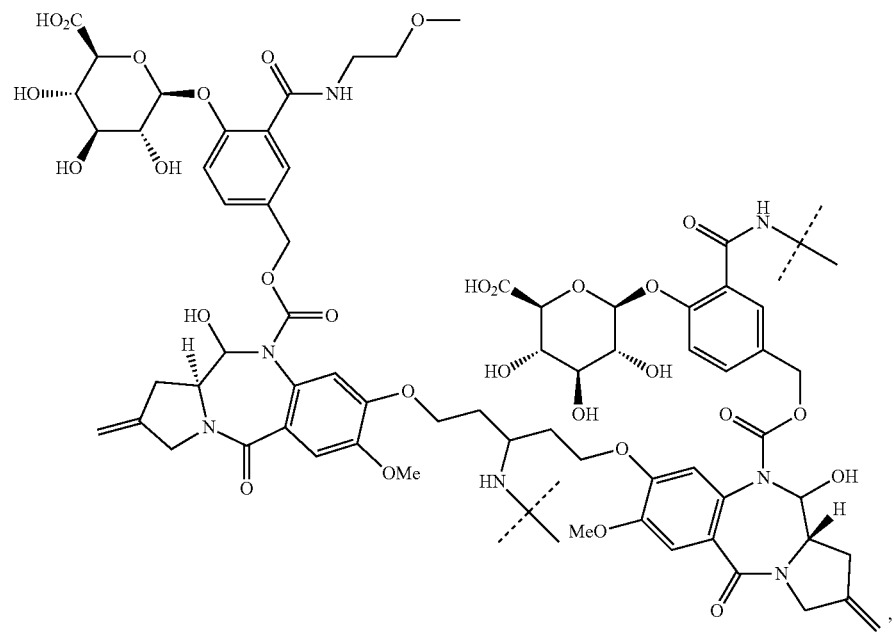
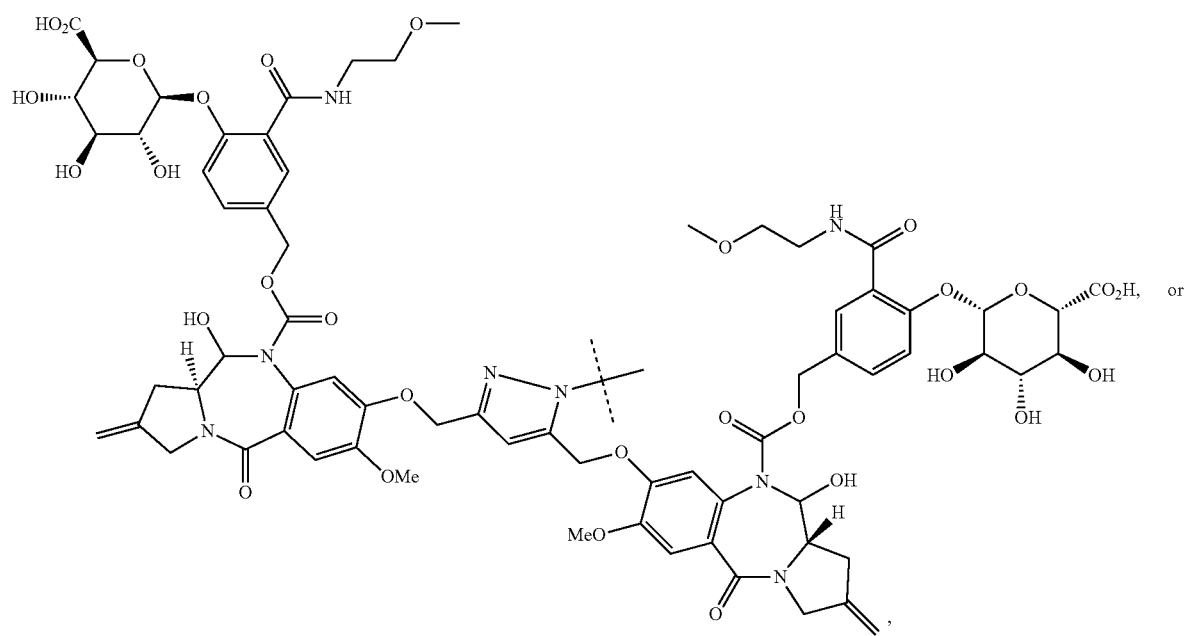

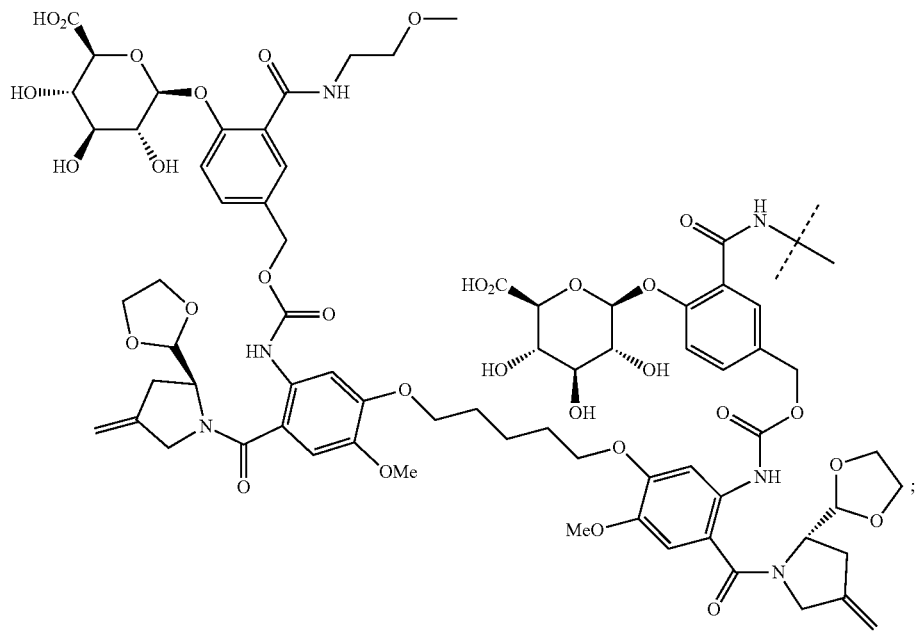

30 and the bond overlaid with a dashed line is a connection point to L.

39. A pharmaceutical composition comprising the antibody conjugate of claim 1.

40. A method of treating a CD19-expressing cancer in a subject, comprising administering the antibody conjugate of claim 1 to the subject, wherein the active agent is an anti-cancer agent.

41. The antibody conjugate of claim 26, comprising the structure:

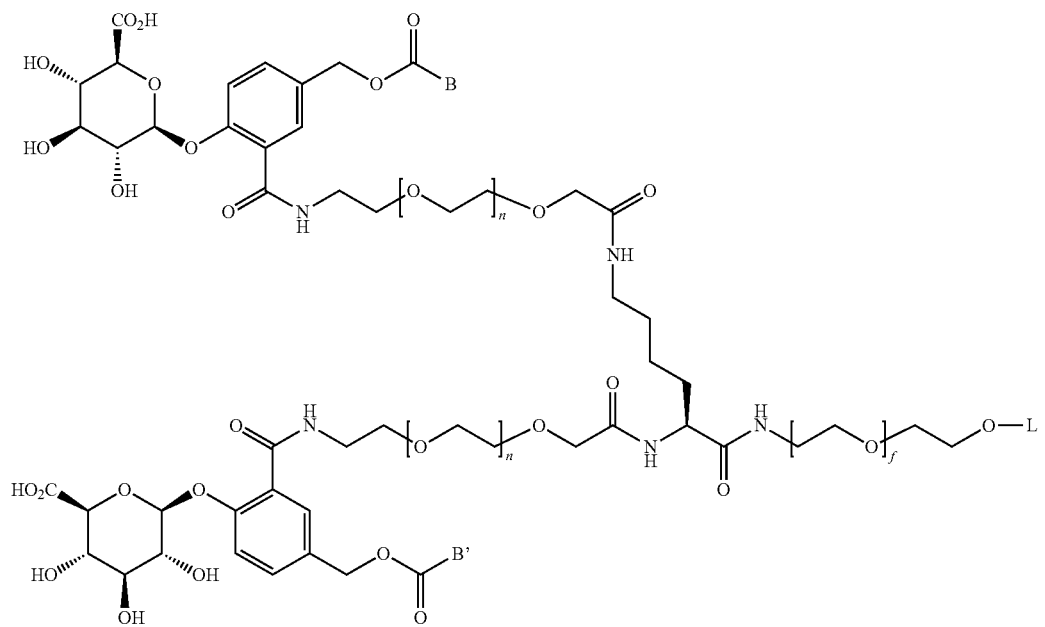

or

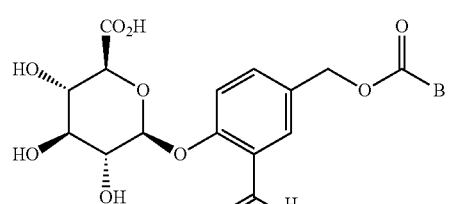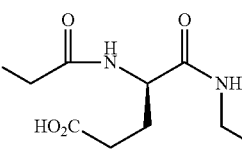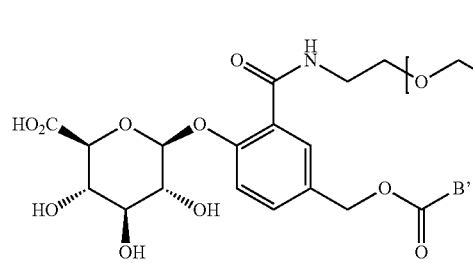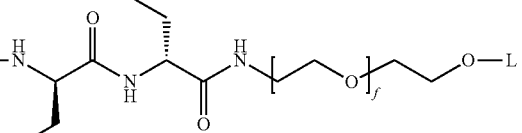
wherein:
B and B' are active agents, which may be the same or different;
n, independently for each occurrence, is an integer from 0 to 30;
f, independently for each occurrence, is an integer from 0 to 30; and
L is a linkage to the Ab.
* * * * *

UNITED STATES PATENT AND TRADEMARK OFFICE
CERTIFICATE OF CORRECTION

PATENT NO. : 11,827,703 B2  
APPLICATION NO. : 16/408002  
DATED : November 28, 2023  
INVENTOR(S) : Song et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 405 days.

Signed and Sealed this  
Eighth Day of July, 2025

Coke Morgan Stewart  
*Acting Director of the United States Patent and Trademark Office*

SEQUENCE LISTING

<160> NUMBER OF SEQ ID NOS: 51

<210> SEQ ID NO 1
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 1

```
gaggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatggggatc atctatcctg gtgactctga taccagatac   180
agcccgtcct tccaaggcca ggtcaccatc tcagccgaca agtccatcag caccgcctac   240
cttcagtgga gcagcctgaa ggcctcggac accgccatgt attactgtgc gagaggtata   300
agtgggatct acaatttaca cggttttgat atctggggcc agggaaccct ggtcacagtc   360
tcgagc                                                              366
```

<210> SEQ ID NO 2
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 2

```
Glu Val Gln Leu Val Gln Ser Gly Ala Glu Val Lys Lys Pro Gly Glu
  1               5                  10                  15
Ser Leu Lys Ile Ser Cys Lys Gly Ser Gly Tyr Ser Phe Thr Ser Tyr
                 20                  25                  30
Trp Ile Gly Trp Val Arg Gln Met Pro Gly Lys Gly Leu Glu Trp Met
             35                  40                  45
Gly Ile Ile Tyr Pro Gly Asp Ser Asp Thr Arg Tyr Ser Pro Ser Phe
         50                  55                  60
Gln Gly Gln Val Thr Ile Ser Ala Asp Lys Ser Ile Ser Thr Ala Tyr
 65                  70                  75                  80
Leu Gln Trp Ser Ser Leu Lys Ala Ser Asp Thr Ala Met Tyr Tyr Cys
                 85                  90                  95
Ala Arg Gly Ile Ser Gly Ile Tyr Asn Leu His Gly Phe Asp Ile Trp
                100                 105                 110
Gly Gln Gly Thr Leu Val Thr Val Ser Ser
            115                 120
```

<210> SEQ ID NO 3
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccatca   180
aggttcagtg gcagtggatc tgggacagat ttcactctca ccatcagcag tctgcaacct   240
gaagattttg caacttacta ctgtcagcag gcgagcttgg acagcccgtt gaccttcggc   300
caagggacca aggtggaaat caaa                                          324
```

<210> SEQ ID NO 4
<211> LENGTH: 108
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ser Leu Asp Ser Pro
                85                  90                  95

Leu Thr Phe Gly Gln Gly Thr Lys Val Glu Ile Lys
            100                 105

<210> SEQ ID NO 5
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
gaggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatgggggatc atctatcctg gtgactctga taccagatac   180
agcccgtcct tccaaggcca ggtcaccatc tcagccgaca gtccatcag caccgcctac   240 cttcagtgga gcagcctgaa ggcctcggac accgccatgt attactgtgc gagaggtgta   300
agtgggatct acaatttaca cggttttgat atctggggcc agggaaccct ggtcacagtc   360
tcgagc                                                              366

<210> SEQ ID NO 6
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

```
Leu Gln Trp Ser Ser Leu Lys Ala Ser Asp Thr Ala Met Tyr Tyr Cys
                85                  90                  95

Ala Arg Gly Val Ser Gly Ile Tyr Asn Leu His Gly Phe Asp Ile Trp
            100                 105                 110

Gly Gln Gly Thr Leu Val Thr Val Ser Ser
        115                 120

<210> SEQ ID NO 7
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgct gcatccagtt tgcaaagtgg ggtcccatca     180
aggttcagtg gcagtggatc tgggacagat ttcactctca ccatcagcag tctgcaacct     240
gaagattttg caacttacta ctgtcagcag ggcatgtggg acaacccgtt caccttcggc     300
caagggacca aggtggaaat caaa                                             324

<210> SEQ ID NO 8
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Met Trp Asp Asn Pro
                85                  90                  95

Phe Thr Phe Gly Gln Gly Thr Lys Val Glu Ile Lys
            100                 105

<210> SEQ ID NO 9
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gacatccaga tgacccagtc tccatcctcc ctgtctgcat ctgtaggaga cagagtcacc      60
atcacttgcc gggcaagtca gagcattagc agctatttaa attggtatca gcagaaacca    120
```

```
gggaaagccc ctaagctcct gatctatgct gcatccagtt tgcaaagtgg ggtcccatca      180
aggttcagtg gcagtggatc tgggacagat ttcactctca ccatcagcag tctgcaacct      240
gaagattttg caacttacta ctgtcagcag ggcaggttcg ggtccccgtt caccttcggc      300
caagggacca aggtggaaat caaa                                              324
```

<210> SEQ ID NO 10
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Arg Phe Gly Ser Pro
                85                  90                  95

Phe Thr Phe Gly Gln Gly Thr Lys Val Glu Ile Lys
            100                 105
```

<210> SEQ ID NO 11
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

```
gaggtgcagc tggtgcagtc tggagcagag gtgaaaaagc ccggggagtc tctgaagatc      60
tcctgtaagg gttctggata cagctttacc agctactgga tcggctgggt gcgccagatg      120
cccgggaaag gcctggagtg gatggggatc atctatcctg gtgactctga taccagatac      180
agcccgtcct tccaaggcca ggtcaccatc tcagccgaca gtccatcagc accgcctac       240 cttcagtgga gcagcctgaa ggcctcggac accgccatgt attactgtgc gagagtctgg      300
tattacgatt tttggagtgg ggccgatgct tttgatatct ggggccaggg aaccctggtc      360
acagtctcga gc                                                           372
```

<210> SEQ ID NO 12
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

```
Glu Val Gln Leu Val Gln Ser Gly Ala Glu Val Lys Lys Pro Gly Glu
1               5                   10                  15
```

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Trp Tyr Tyr Asp Phe Trp Ser Gly Ala Asp Ala Phe Asp
            100                 105                 110

Ile Trp Gly Gln Gly Thr Leu Val Thr Val Ser Ser
        115                 120

<210> SEQ ID NO 13
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13
gaaatagtga tgacgcagtc tccagccacc ctgtctgtgt ctccagggga agagccacc      60 ctctcctgca gggccagtca gagtgttagc agcaacttag cctggtacca gcagaaacct    120
ggccaggctc ccaggctcct catctatggt gcatccacca gggccactgg tatcccagcc    180
aggttcagtg gcagtgggtc tgggacagag ttcactctca ccatcagcag cctgcagtct    240
gaagattttg cagtttatta ctgtcagcag ggcagcttgg aggcgccgca gaccttcggc    300
caagggacca aggtggaaat caaa                                           324

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Gly Ser Leu Glu Ala Pro
                85                  90                  95

Gln Thr Phe Gly Gln Gly Thr Lys Val Glu Ile Lys
            100                 105

<210> SEQ ID NO 15
<211> LENGTH: 354

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
gaggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatggggatc atctatcctg gtgactctga taccagatac   180
agcccgtcct tccaaggcca ggtcaccatc tcagccgaca gtccatcag caccgcctac    240 ctgcagtgga gcagcctgaa ggcctcggac accgccatgt attactgtgc gagaggtgat   300
tattggactg gttttgctta ttggggccag ggaaccctgg tcacagtctc gagc         354
```

<210> SEQ ID NO 16
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Asp Tyr Trp Thr Gly Phe Ala Tyr Trp Gly Gln Gly Thr
            100                 105                 110

Leu Val Thr Val Ser Ser
        115
```

<210> SEQ ID NO 17
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
cagtctgtgt tgacgcagcc gccctcagtg tctgcggccc caggacagaa ggtcaccatc    60
tcctgctctg gaagcagctc aacattggg aataattatg tatcctggta ccagcagctc    120
ccaggaacag cccccaaact cctcatttat gacaataata agcgaccctc agggattcct    180
gaccgattct ctggctccaa gtctggcacg tcagccaccc tgggcatcac cggactccag    240
actggggacg aggccgatta ttactgcgga acatgggatc tgggctggaa ctcggtgttc    300
ggcggaggga ccaagctgac cgtccta                                        327
```

<210> SEQ ID NO 18
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Ser Val Leu Thr Gln Pro Pro Ser Val Ala Ala Pro Gly Gln
1               5                   10                  15

Lys Val Thr Ile Ser Cys Ser Gly Ser Ser Asn Ile Gly Asn Asn
                20                  25                  30

Tyr Val Ser Trp Tyr Gln Leu Pro Gly Thr Ala Pro Lys Leu Leu
                35                  40                  45

Ile Tyr Asp Asn Asn Lys Arg Pro Ser Gly Ile Pro Asp Arg Phe Ser
50                  55                  60

Gly Ser Lys Ser Gly Thr Ser Ala Thr Leu Gly Ile Thr Gly Leu Gln
65                  70                  75                  80

Thr Gly Asp Glu Ala Asp Tyr Tyr Cys Gly Thr Trp Asp Leu Gly Trp
                85                  90                  95

Asn Ser Val Phe Gly Gly Gly Thr Lys Leu Thr Val Leu
            100                 105

<210> SEQ ID NO 19
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag ggcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagagatcgg    300
gggtatgatt acgtttgggg gagttatcgt tatggtgcct ttgatatctg ggccaggga     360 accctggtca cagtctcgag c                                               381

<210> SEQ ID NO 20
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
                35                  40                  45

Gly Gly Ile Ile Pro Ile Phe Gly Thr Ala Asn Tyr Ala Gln Lys Phe
50                  55                  60

```
Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asp Arg Gly Tyr Asp Tyr Val Trp Gly Ser Tyr Arg Tyr Gly
            100                 105                 110

Ala Phe Asp Ile Trp Gly Gln Gly Thr Leu Val Thr Val Ser Ser
        115                 120                 125

<210> SEQ ID NO 21
<211> LENGTH: 333
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
cagtctgccc tgactcagcc tgcctccgtg tctgggtctc ctggacagtc gatcaccatc        60
tcctgcactg gaaccagcag tgacgttggt ggttataact atgtctcctg gtaccaacag       120
cacccaggca agcccccaa actcatgatt tatgaggtca gtaatcggcc ctcagggggtt       180 tctaatcgct tctctggctc caagtctggc aacacggcct ccctgaccat ctctgggctc       240
caggctgagg acgaggctga ttattactgc agctcatatg atgtctgggt cccgcacatg       300
gtgttcggcg gagggaccaa gctgaccgtc cta                                    333

<210> SEQ ID NO 22
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Tyr Asp Val Trp
                 85                  90                  95

Val Pro His Met Val Phe Gly Gly Gly Thr Lys Leu Thr Val Leu
            100                 105                 110

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Tyr Ser Phe Thr Ser Tyr Trp
```

```
<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ile Tyr Pro Gly Asp Ser Asp Thr
1               5

<210> SEQ ID NO 25
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Arg Gly Ile Ser Gly Ile Tyr Asn Leu His Gly Phe Asp Ile
1               5                   10                  15

<210> SEQ ID NO 26
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Arg Gly Val Ser Gly Ile Tyr Asn Leu His Gly Phe Asp Ile
1               5                   10                  15

<210> SEQ ID NO 27
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Arg Val Trp Tyr Tyr Asp Phe Trp Ser Gly Ala Asp Ala Phe Asp
1               5                   10                  15

Ile

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Arg Gly Asp Tyr Trp Thr Gly Phe Ala Tyr
1               5                   10

<210> SEQ ID NO 29
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 29

Gly Gly Thr Phe Ser Ser Tyr Ala
1               5

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ile Ile Pro Ile Phe Gly Thr Ala
1               5

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Ala Arg Asp Arg Gly Tyr Asp Tyr Val Trp Gly Ser Tyr Arg Tyr Gly
1               5                   10                  15

Ala Phe Asp Ile
            20

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Ser Ile Ser Ser Tyr
1               5

<210> SEQ ID NO 33
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Ala Ser
1

<210> SEQ ID NO 34
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34
```

Gln Gln Ala Ser Leu Asp Ser Pro Leu Thr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Gln Gly Met Trp Asp Asn Pro Phe Thr
1               5                   10

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Gln Gly Arg Phe Gly Ser Pro Phe Thr
1               5                   10

<210> SEQ ID NO 37
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gln Ser Val Ser Ser Asn
1               5

<210> SEQ ID NO 38
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ala Ser
1

<210> SEQ ID NO 39
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gaggtgcagc tggtgcagtc tggagcagag gtgaaaaagc ccggggagtc tctgaagatc        60
tcctgtaagg gttctggata cagctttacc agctactgga tcggctgggt gcgccagatg       120
cccgggaaag gcctggagtg gatggggatc atctatcctg gtgactctga taccagatac       180
agcccgtcct tccaaggcca ggtcaccatc tcagccgaca gtccatcag caccgcctac        240 cttcagtgga gcagcctgaa ggcctcggac accgccatgt attactgtgc gagaggtgta       300

```
agtgggatct acaatttaca cggtttcgat atctggggcc agggaaccct ggtcacagtc    360
tcgagc                                                                366
```

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Gly Ser Leu Glu Ala Pro Gln Thr
1               5                   10

<210> SEQ ID NO 41
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Ser Ser Asn Ile Gly Asn Asn Tyr
1               5

<210> SEQ ID NO 42
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asp Asn Asn
1

<210> SEQ ID NO 43
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Thr Trp Asp Leu Gly Trp Asn Ser Val
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Ser Ser Asp Val Gly Gly Tyr Asn Tyr
1               5

<210> SEQ ID NO 45
<211> LENGTH: 3
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 45

Glu Val Ser
1

<210> SEQ ID NO 46
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ser Ser Tyr Asp Val Trp Val Pro His Met Val
1               5                   10

<210> SEQ ID NO 47
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Cys Val Ile Met
1

<210> SEQ ID NO 48
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Cys Val Leu Leu
1

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Gly Gly Gly Gly Gly Gly Cys Val Ile Met
1               5                   10

<210> SEQ ID NO 50
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This region may encompass 0-20 residues
```

```
<400> SEQUENCE: 50

Gly Gly Gly Gly Gly Gly Gly Gly Gly Gly Gly Gly Gly Gly Gly
1               5                   10                  15

Gly Gly Gly Gly Cys Val Ile Met
            20

<210> SEQ ID NO 51
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(20)
<223> OTHER INFORMATION: This region may encompass 0-20 residues

<400> SEQUENCE: 51

Gly Gly Gly Gly Gly Gly Gly Gly Gly Gly Gly Gly Gly Gly Gly
1               5                   10                  15

Gly Gly Gly Gly Cys Val Leu Leu
            20
```